(12) United States Patent
Deutsch et al.

(10) Patent No.: US 11,879,126 B2
(45) Date of Patent: Jan. 23, 2024

(54) MRNA TREATMENT NANOPARTICLES

(71) Applicant: Nutcracker Therapeutics, Inc., Emeryville, CA (US)

(72) Inventors: Samuel Deutsch, Walnut Creek, CA (US); Daniel Frimannsson, Alameda, CA (US); Nicole Fay, Alameda, CA (US); Colin McKinlay, Fremont, CA (US); Ole Haabeth, Emeryville, CA (US)

(73) Assignee: Nutcracker Therapeutics, Inc., Emeryville, CA (US)

( * ) Notice: Subject to any disclaimer, the term of this patent is extended or adjusted under 35 U.S.C. 154(b) by 0 days.

(21) Appl. No.: 18/048,390

(22) Filed: Oct. 20, 2022

(65) Prior Publication Data

US 2023/0193288 A1    Jun. 22, 2023

Related U.S. Application Data

(63) Continuation of application No. PCT/US2021/028312, filed on Apr. 21, 2021.

(60) Provisional application No. 63/014,074, filed on Apr. 22, 2020.

(51) Int. Cl.
| | |
|---|---|
| *C12N 15/117* | (2010.01) |
| *A61P 35/00* | (2006.01) |
| *A61K 9/14* | (2006.01) |
| *A61K 45/06* | (2006.01) |
| *C07K 16/28* | (2006.01) |

(52) U.S. Cl.
CPC ............ *C12N 15/117* (2013.01); *A61K 9/145* (2013.01); *A61K 45/06* (2013.01); *A61P 35/00* (2018.01); *C07K 16/2818* (2013.01)

(58) Field of Classification Search
CPC .... C12N 15/113; C12N 15/117; A61K 45/06; A61K 9/145; A61P 35/00

USPC ............. 435/6.1, 91.1, 91.31, 455, 458; 514/44 R, 44 A; 536/23.1, 24.5
See application file for complete search history.

(56) References Cited

U.S. PATENT DOCUMENTS

| | | | |
|---|---|---|---|
| 11,598,780 B2 * | 3/2023 | Nakamura | ......... G01N 33/5005 |
| 2004/0096835 A1 | 5/2004 | Dobie | |
| 2016/0016140 A1 | 1/2016 | Jovanovich et al. | |
| 2018/0311343 A1 | 11/2018 | Huang et al. | |
| 2019/0142971 A1 | 5/2019 | Hoge et al. | |
| 2019/0202920 A1 | 7/2019 | Tuna et al. | |

FOREIGN PATENT DOCUMENTS

WO    2017193084    11/2017

OTHER PUBLICATIONS

PCT, International Preliminary Report of Patentability regarding PCT Application No. PCT/US2021/028312, 14 pages, dated Nov. 3, 2022.
PCT, International Search Report regarding PCT Application No. PCT/US2021/028312, dated Sep. 10, 2021, 4 pages.
Baiersdorfer, Markus, et al., Molecular Therapy, A Facile Method for the Removal of dsRNA Contaminant from In Vitro-Transcribed mRNA, Molecular Therapy: Nucleic Acids vol. Apr. 15, 2019, 10 pages.

* cited by examiner

*Primary Examiner* — Jane J Zara
(74) *Attorney, Agent, or Firm* — McAndrews, Held & Malloy, Ltd.

(57) ABSTRACT

Provided herein are examples of mRNA treatment nanoparticles and methods of using them to treat a patient. An mRNA treatment nanoparticle may include one or more mRNAs encoding a tumor-specific antigen and an immunomodulatory agent; and a delivery vehicle molecule encapsulating the one or more mRNAs.

16 Claims, 29 Drawing Sheets

Specification includes a Sequence Listing.

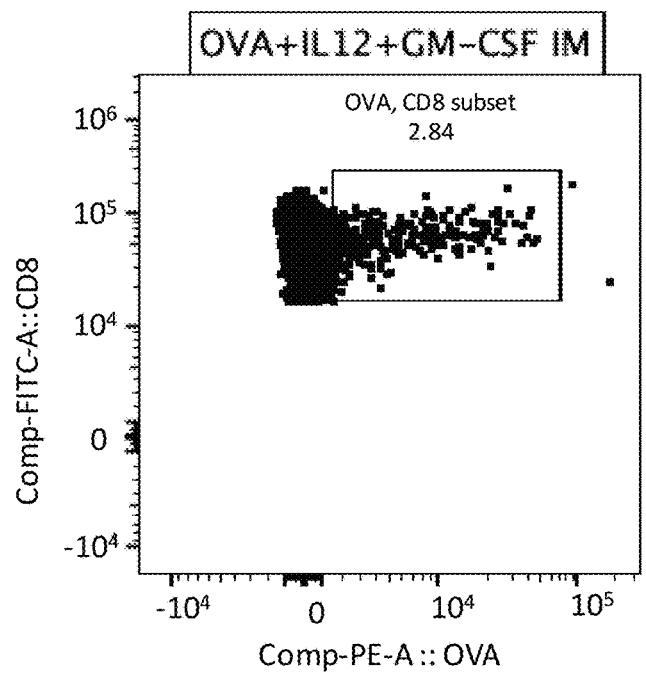
FIG. 10E
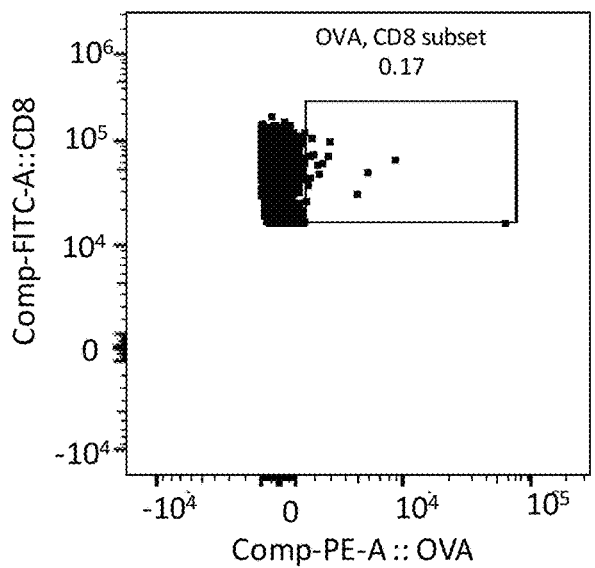 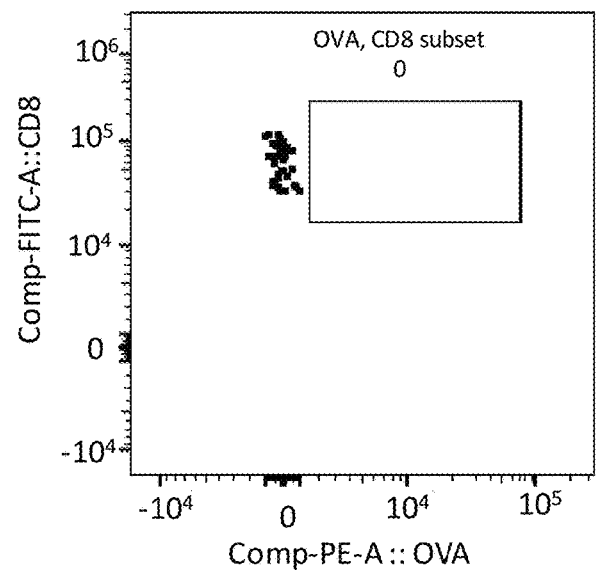
FIG. 10F        FIG. 10G

|  | OVA+CpG | CpG | OVA+IL12 | IL12 |
|---|---|---|---|---|
| Response rate Proximal Tumor | 50% | 30% | 70% | 0% |
| Response Rate Distal Tumor | 50% | 20% | 50% | 30% |
| Overall response Both Tumors | 20% | 20% | 40% | 0% |

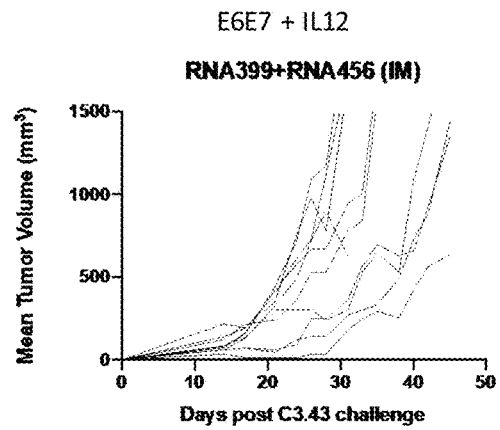
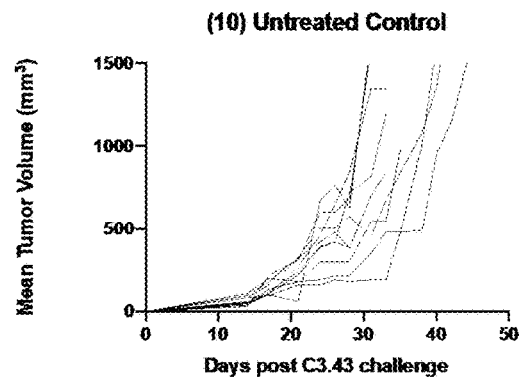
FIG. 31A        FIG. 31B
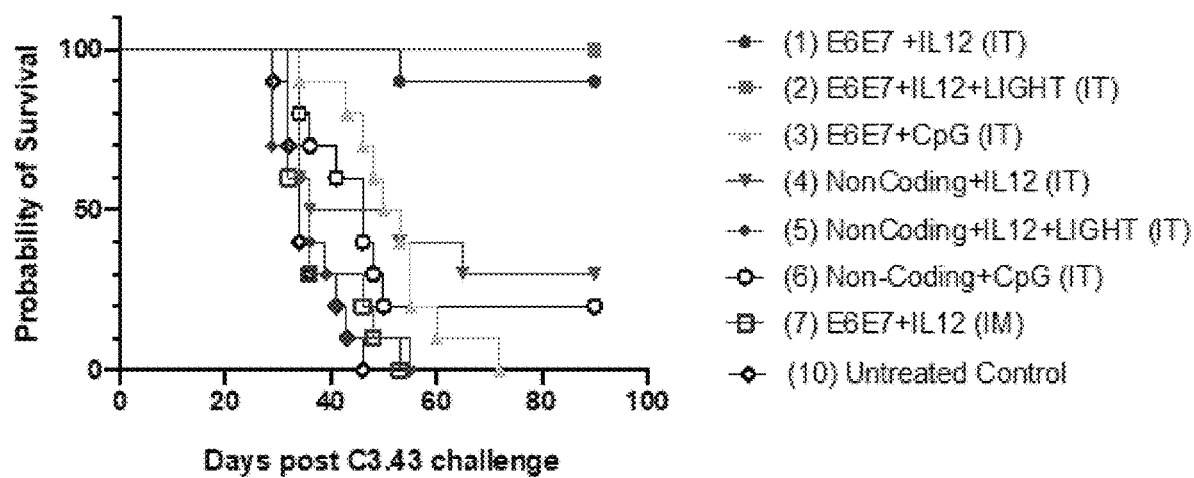
FIG. 32

MRNA TREATMENT NANOPARTICLES

CROSS REFERENCE TO RELATED APPLICATIONS

The present patent application is a continuation of PCT/US2021/028312, filed Apr. 21, 2021, and is related to and claims priority to U.S. provisional patent application No. 63/014,074, titled "MRNA THERAPIES" and filed on Apr. 22, 2020, the content of each of the aforementioned applications which is hereby incorporated by reference in its/their entirety into this disclosure.

INCORPORATION BY REFERENCE

All publications and patent applications mentioned in this specification are herein incorporated by reference in their entirety to the same extent as if each individual publication or patent application was specifically and individually indicated to be incorporated by reference.

REFERENCE TO AN ELECTRONIC SEQUENCE LISTING

The contents of the electronic sequence listing (66656US02sequence.xml; Size: 26,862 bytes; and Date of Creation: Oct. 18, 2022) is herein incorporated by reference in its entirety.

BACKGROUND mRNA-based vaccines have the benefit of triggering robust anti-cancer immunity without the potential danger of genome integration from DNA vaccines or the limitation of antigen selection from peptide vaccines. Unfortunately, conventional mRNA vaccines are not effectively internalized by antigen-presenting cells and may not offer sufficient protection for mRNA molecules from degradation by plasma and tissue enzymes. Although mRNA is an emerging platform for antibody gene transfer, the further development of mRNA based mAb is limited by the need for safe and effective delivery systems.

In addition, mRNA can only lead to Ab with natural posttranslational modifications, meaning that conjugates and modifications to increase serum half-life (for example by PEGylation) are not typically possible for Ab encoded by mRNA. For passive immunization a very high safety profile is required. Over the past decades, different optimizations have been described for IVT mRNA in order to avoid unwanted immune activation and cytokine induction induced by cellular RNA sensors. Despite the above described adaptations to the IVT mRNA, emergence of ADA (anti-drug antibody) responses and transient cytokines have hampered the clinical applicability of mRNA-drugs, especially when the mRNA has to be administered multiple times, in some instances leading to induction of complement activation-related pseudoallergy (CARPA).

SUMMARY OF THE DISCLOSURE

Described herein are methods and compositions (including kits) that may address these problems. Provided herein are examples methods for treating cancer and, in particular, to methods for making mRNA (treatment) nanoparticles, method of treating a patient using these mRNA nanoparticles (e.g., including mRNA vaccines). In particular, described herein are mRNA therapies being administered to a patient in need thereof. The patient can be a mammal, for example, a human. The patient may have any of the tumors (or in some instances cancers) described herein, and thus in some instances in need of the therapies, or treatments, described herein. The mRNA therapies involve administering (to a patient or a site of a patient) mRNA (treatment) nanoparticles, including mRNA encoding one or more patient-specific antigens and mRNA encoding one or more immunomodulatory agents, as well as apparatuses and methods for making patient-specific mRNA therapies.

In particular, described herein are mRNA treatments, including mRNA vaccines, methods for treating cancer, which herein refers to tumors that are not benign, or tumor, which can be benign or cancerous, using these mRNA treatments, and methods of forming these mRNA treatments. For example, described herein are methods of that include the intratumoral injection of an mRNA treatment nanoparticle encoding a tumor-specific antigen, and an mRNA encoding an immunomodulatory agent, wherein the mRNA encoding the tumor-specific antigen and the immunomodulatory agent are encapsulated together by a delivery vehicle molecule, for example, an amino-lipidated peptoid. While the injection may be intratumoral, as provided in some examples herein, other routes of administrations are also possible.

Any of the methods described herein may be methods of treatment, including methods of treating a cancer (e.g., to reduce, or in some instances eliminate, a tumor).

The methods described herein may include: injecting an mRNA treatment nanoparticle comprising: one or more mRNAs encoding a tumor-specific antigen and an immunomodulatory agent; and a delivery vehicle molecule encapsulating the one or more mRNAs. For example, a method may include: one or more mRNAs encoding a tumor-specific antigen and one or more immunomodulatory agent; and a delivery vehicle molecule encapsulating the one or more mRNAs. In some examples, a method may include intratumorally injecting an mRNA treatment nanoparticle comprising one or more mRNAs encoding a tumor-specific antigen and one or more immunomodulatory agents, wherein the at least one or more immunomodulatory agents are a checkpoint inhibitor; and a delivery vehicle molecule encapsulating the one or more mRNAs. In some examples, the method may include: intratumorally injecting an mRNA treatment nanoparticle comprising: one or more mRNAs encoding a tumor-specific antigen, two or more immunomodulatory agents; and a delivery vehicle molecule encapsulating the one or more mRNAs, wherein the delivery vehicle molecule comprises an amino-lipidated peptoid delivery vehicle.

For example, described herein are methods comprising: injecting an mRNA treatment nanoparticle comprising an mRNA encoding a tumor-specific antigen (e.g., an mRNA vaccine) and an mRNA encoding an immunomodulatory agent, wherein the mRNA encoding the tumor-specific antigen and the immunomodulatory agent are encapsulated with the same delivery vehicle molecule. For example, the method may include: intratumorally injecting an mRNA treatment nanoparticle comprising an mRNA encoding a tumor-specific antigen and an mRNA encoding one or more immunomodulatory agents, wherein the mRNA vaccine and the immunomodulatory agent are encapsulated with the same nanoparticle delivery.

A method may include: intratumorally injecting an mRNA treatment nanoparticle comprising an mRNA encoding a tumor-specific antigen (e.g., mRNA vaccine) and mRNAs encoding two or more immunomodulatory agents, wherein at least one of the two or more immunomodulatory agents is a checkpoint inhibitor, further wherein the mRNA encoding the tumor-specific antigen and the mRNAs encoding the immunomodulatory agents are encapsulated with the same delivery vehicle molecule.

In some variations a method includes: intratumorally injecting an mRNA treatment nanoparticle comprising an mRNA encoding a tumor-specific antigen (e.g., mRNA vaccine) and mRNA encoding two or more immunomodulatory agents, wherein the mRNA encoding the tumor-specific antigen and the mRNA encoding the two or more immunomodulatory agents is encapsulated with a delivery vehicle molecule comprising an amino-lipidated peptoid delivery vehicle.

Any of these methods or compositions (e.g., mRNA therapies) may include one or more siRNAs, including one or more immunomodulator siRNAs. For example, a method may include: intratumorally injecting an mRNA treatment nanoparticle comprising an mRNA encoding a tumor-specific antigen, mRNAs encoding one or more immunomodulatory agents, and one or more immunomodulatory siRNAs wherein the mRNA encoding the tumor-specific antigen, the mRNA encoding the one or more immunomodulatory agents and the one or more siRNAs are encapsulated with the same delivery vehicle molecule.

Any appropriate delivery vehicle may be used. For example, the delivery vehicle molecule may be a lipid based vehicle (such as a lipid nanoparticle) or a polymer-based nanoparticle. In particular the delivery vehicle (DV) molecule may be an amino-lipidated peptoid delivery vehicle. In any of these methods the delivery vehicle molecule may comprise an amino-lipidated peptoid. In one example, the delivery vehicle molecule comprises at least one peptoid, which can be any type of peptoid described herein. In another example, the delivery vehicle molecule comprises more than one peptoid, which can be any type of peptoid described herein.

The mRNA encoding the tumor-specific antigen may comprise an mRNA encoding a patient-specific antigen (or multiple patient-specific antigens). For example, the mRNA treatment (e.g., mRNA vaccine) may comprise an mRNA encoding a plurality of patient-specific antigens. The mRNA encoding the tumor-specific antigen may include an mRNA encoding a shared tumor antigen.

The mRNA encoding an immunomodulatory agent encodes: a checkpoint inhibitor, an immunosuppression antagonist, a pro-inflammatory agent, or combinations thereof. For example, the mRNA encoding an immunomodulatory agent encodes anti-CTLA-4. The mRNA encoding an immunomodulatory agent may encode a TGF-beta antagonist. The mRNA encoding an immunomodulatory agent may encode a single chain interleukin-12 (IL-12).

Any of the mRNA therapies and methods of making or using them may include the addition of one or more adjuvant, which may be included with the mRNA treatment. In some variations the delivery vehicle molecules may be mixed with, include and/or encapsulate the additional adjuvant. In some variations the additional adjuvant may be combined with the solution including the nanoparticles encapsulating the therapeutic mRNAs (e.g., the tumor-specific mRNA and the one or more immunomodulator mRNA). For example, any of these mRNA therapies may further include an immunostimulator. For example the immunostimulator may comprise a CpG oligodeoxynucleotides.

In use, any of these methods may include repeating the injection treatment one or more times with a 1-7 day wait between treatments. As mentioned, the injection may be (but is not limited to) intratumoral. In some variations, the injection may be both intratumoral and/or by other means (subcutaneous, etc.).

The mRNA encoding the tumor-specific antigen and the mRNA encoding the immunomodulatory agent(s) may be on a single mRNA strand, or on separate mRNA strands.

In general, these methods may be methods of treating a tumor, e.g., to reduce the tumor size. The tumor may be reduced between about 10% and about 100%, between about 10% and about 90%, between about 10% and about 80%, between about 10% and about 70%, between about 10% and about 60%, between about 10% and about 50%, between about 10% and about 40%, greater than about 10%, greater than about 15%, greater than about 20%, greater than about 25%, greater than about 30%, greater than about 40%, greater than about 50%, greater than about 60%, greater than about 70%, greater than about 75%, etc.

Any appropriate cancer or tumor may be treated, as described herein. For example, and of these methods may be methods of treating Lymphoma. The method described herein may be methods of treating cervical cancer.

Also described herein are mRNA therapies including mRNA treatment nanoparticles as (e.g., an mRNA vaccine nanoparticle). In general, an mRNA treatment nanoparticle may include: one or more mRNAs encoding a tumor-specific antigen and an immunomodulatory agent; and a delivery vehicle molecule, wherein the one or more mRNAs are encapsulated together by the delivery vehicle molecule. An mRNA treatment nanoparticle may include: a first mRNA encoding a tumor-specific antigen (e.g., mRNA vaccine); a second mRNA encoding an immunomodulatory agent; and a delivery vehicle molecule encapsulating the first mRNA and the second mRNA. For example, an mRNA vaccine nanoparticle may include: a first mRNA encoding a tumor-specific antigen; a second mRNA encoding an immunomodulatory agent comprising a checkpoint inhibitor; a third mRNA encoding a second immunomodulatory agent; and a delivery vehicle molecule encapsulating the first mRNA, the second mRNA and the third mRNA.

An mRNA treatment nanoparticle may include: a first mRNA encoding a tumor-specific antigen; a second mRNA encoding an immunomodulatory agent comprising a checkpoint inhibitor; a third mRNA encoding a second immunomodulatory agent; and a delivery vehicle molecule comprising an amino-lipidated peptoid delivery vehicle encapsulating the first mRNA, the second mRNA and the third mRNA.

Any of these mRNA treatment vaccines may include one or more siRNAs, including immunomodulatory siRNAs.

As mentioned above, any appropriate delivery vehicle molecule may be used. For example, the delivery vehicle molecule may comprise an amino-lipidated peptoid delivery vehicle.

The first mRNA may encode a patient-specific antigen. For example, the first mRNA may encode a plurality of patient-specific antigens. The first mRNA may encode a shared tumor antigen. The second mRNA may encode: a checkpoint inhibitor, an immunosuppression antagonist, a pro-inflammatory agent, or combinations thereof. The second mRNA may encode an anti-CTLA-4. For example, the second mRNA may encode an anti-CTLA-4 and may have a polynucleotide sequence that is at least about 50% (e.g., about 60%, about 65%, about 70%, about 75%, about 80%, about 85%, about 90%, or more) identical to the polynucleotide sequence of SEQ ID No: 1 or SEQ ID NO: 3. In some examples, the second mRNA may encode an anti-CTLA-4 that is at least about 50% (e.g., about 60%, about 65%, about 70%, about 75%, about 80%, about 85%, about 90%, or more) identical to the polypeptide sequence of SEQ ID No: 2 or SEQ ID NO: 4. The second mRNA may encode a TNFSF14 (tumor necrosis factor receptor superfamily member 14 isoform1 precursor, or LIGHT). For example, the second mRNA may encode TNFSF14 and may have a polynucleotide sequence that is at least about 50% (e.g., about 60%, about 65%, about 70%, about 75%, about 80%, about 85%, about 90%, or more) identical to the polynucleotide sequence of SEQ ID No: 11. In some examples, the second mRNA may encode TNFSF14 that is at least about 50% (e.g., about 60%, about 65%, about 70%, about 75%, about 80%, about 85%, about 90%, or more) identical to the polypeptide sequence of SEQ ID No: 12. The third mRNA may encode a TGF-beta antagonist. The third mRNA may encode a TGF-beta antagonist and may have a polynucleotide sequence that is at least about 50% (e.g., at least about 60%, about 65%, about 70%, about 75%, about 80%, about 85%, about 90%, or more) identical to the polynucleotide sequence of SEQ ID NO: 7 or SEQ ID NO: 9. The third mRNA may encode a TGF-beta antagonist that is at least about 50% (e.g., at least about 60%, about 65%, about 70%, about 75%, about 80%, about 85%, about 90%, or more) identical to the polypeptide sequence of SEQ ID NO: 8 or SEQ ID NO: 10. The third mRNA may encode a single chain interleukin-12. For example, the third mRNA may encode a single chain interleukin-12 and may have a polynucleotide sequence that is at least about 50% (e.g., at least about 60%, about 65%, about 70%, about 75%, about 80%, about 85%, about 90%, or more) identical to the polynucleotide sequence of SEQ ID NO: 5. The third mRNA may encode a single chain interleukin-12 that is at least about 50% (e.g., at least about 60%, about 65%, about 70%, about 75%, about 80%, about 85%, about 90%, or more) identical to the polypeptide sequence of SEQ ID NO: 6

The mRNA treatment nanoparticle may include an additional mRNA encoding another immunomodulatory agent that is different from the other immunomodulatory agents already in the mRNA treatment nanoparticle. As described herein three or more distinct immunomodulatory mRNAs may be included with the tumor-specific mRNA in any of these mRNA therapies.

The mRNA treatment nanoparticles described herein may include and/or be combined with one or more immunomodulator, as described above. For example, the mRNA treatment nanoparticles described herein may include and/or be combined with an immunostimulator, such as a CpG oligodeoxynucleotide.

The mRNA encoding the tumor-specific antigen and all or some of the one or more mRNAs encoding the immunomodulatory agent may be part of a single mRNA strand. Specifically, these mRNAs (or some of them) may be combined so that, for example, the mRNA encoding the tumor-specific antigen and the mRNA(s) encoding the immunomodulatory agent(s) may be a single mRNA combining the two or more open reading frames of the tumor-specific antigen and the mRNA(s) encoding the immunomodulatory agent(s) within a single continuous mRNA. For example, the first mRNA encoding the tumor-specific antigen and the second mRNA encoding an immunomodulatory agent may be a single mRNA strand including the ORFs for the first mRNA (the mRNA encoding the tumor-specific antigen) and the second mRNA (encoding the immunomodulatory agent). Alternatively, the first mRNA and the second mRNA may be part of different mRNA strands.

Also described herein are methods of making (e.g., method of fabricating, method of manufacturing, methods of synthesizing, etc.) the mRNA therapies (e.g., the mRNA treatment nanoparticles) described herein. For example, a method (e.g., of making an mRNA treatment nanoparticle) may include: performing in vitro transcription of a first mRNA encoding a tumor-specific antigen in a microfluidic path device; performing in vitro transcription of a second mRNA encoding a first immunomodulatory agent in the microfluidic path device; purifying the first and second mRNAs in the microfluidic path device; and combining the first mRNA and the second mRNA with a delivery vehicle molecule in the microfluidic path device to form an mRNA treatment nanoparticle.

In some examples, the method may include: performing in vitro transcription of a first mRNA encoding a tumor-specific antigen in a closed-path microfluidic path device; performing in vitro transcription of a second mRNA encoding a first immunomodulatory agent in the microfluidic path device; purifying the first and second mRNAs in the microfluidic path device; and combining the first mRNA and the second mRNA with a delivery vehicle molecule in the microfluidic path device.

A method of making an mRNA treatment nanoparticle may include: performing in vitro transcription of a first mRNA encoding a tumor-specific antigen from the template in a closed-path microfluidic path device; purifying the first mRNA; performing in vitro transcription of a second mRNA encoding a first immunomodulatory agent in the microfluidic path device; purifying the second mRNAs in the microfluidic path device; and encapsulating both the first mRNA and the second mRNA together with a delivery vehicle molecule in the microfluidic path device to form an mRNA treatment nanoparticle.

A method (e.g., of making an mRNA treatment nanoparticle), the method comprising: performing in vitro transcription of a first mRNA encoding a tumor-specific antigen from the template in a first chamber of a (e.g., closed-path) microfluidic path device; purifying the first mRNA; performing in vitro transcription of a second mRNA encoding a first immunomodulatory agent in a second chamber of the microfluidic path device; purifying the second mRNAs in the microfluidic path device; performing in vitro transcription of a third mRNA encoding a second immunomodulatory agent in a third chamber of the microfluidic path device; purifying the third mRNAs in the microfluidic path device; and encapsulating the first mRNA, second mRNA and the third mRNA together with a delivery vehicle molecule in the microfluidic path device to form an mRNA treatment nanoparticle.

Purifying the first, second and third mRNA may comprise purifying the first, second or third mRNAs in one or more reactors on the microfluidic path device. The one or more reactors for purifying the mRNA may include a double-stranded mRNA binding material such as cellulose within the one or more reactors to remove double stranded mRNA.

The microfluidic path device may comprise a closed-path system configured to automatically and continuously perform the processes of performing in vitro transcription of first and second mRNA from one or more template, purifying the first and second mRNA (and third, fourth, etc.), and combining the mRNAs with the delivery vehicle molecule. The closed-path system may pneumatically control performing in vitro transcription of mRNAs, purifying the mRNAs, and combining the mRNAs with the delivery vehicle molecule.

The closed-path system may pneumatically control performing in vitro transcription of first and second mRNA from template, purifying the first and second mRNA, and combining the first and second mRNA with the delivery vehicle molecule by deflecting one or more membranes within the microfluidic path device. The closed-path system may automatically and continuously perform the processes of performing in vitro transcription of therapeutic mRNA from the template, purifying the therapeutic mRNA, and combining the mRNA with a delivery vehicle, in less than 5 days. The method may be performed at a site of care. Combining the mRNA with the delivery vehicle may further comprise dialyzing the mRNA treatment nanoparticle composition in the microfluidic path device.

Any of these methods and systems for performing them may include concentrating the mRNA treatment nanoparticle on the microfluidic path device.

As mentioned, the delivery vehicle molecule may be any appropriate delivery vehicle, including an amphipathic nanoparticle (e.g., an amino-lipidated peptoid). The first mRNA encoding the tumor-specific antigen may comprise an mRNA encoding a patient-specific antigen. The first mRNA may encode a plurality of patient-specific antigens. The first mRNA encoding the tumor-specific antigen may comprise an mRNA encoding a shared tumor antigen. The second mRNA encoding the immunomodulatory agent may encode: a checkpoint inhibitor, an immunosuppression antagonist, a pro-inflammatory agent, or combinations thereof. The second mRNA encoding an immunomodulatory agent may encode anti-CTLA-4. The second mRNA encoding an immunomodulatory agent may encode a TGF-beta antagonist. The second mRNA encoding an immunomodulatory agent may encode a single chain interleukin-12 (IL-12). Combining the mRNAs (e.g., the first and the second mRNAs, third mRNAs, etc.) may include adding an immunostimulator to the mRNA treatment nanoparticle while the mRNA treatment nanoparticle is in the microfluidic path device, such as a CpG oligodeoxynucleotides.

Described herein are methods comprising intratumorally injecting an mRNA treatment nanoparticle encoding a tumor-specific antigen and mRNAs encoding two or more immunomodulatory agents, wherein at least one of the two or more immunomodulatory agents is a checkpoint inhibitor, further wherein the mRNA vaccine and the immunomodulatory agent are encapsulated together by a single delivery vehicle molecule, such as an amino-lipidated peptoid delivery vehicle.

For example, described herein are methods of treatment. These methods may have improved efficacy for the mRNA vaccine, particularly for the treatment of cancer. Encapsulating both the mRNA encoding the tumor-specific mRNA and the mRNA(s) encoding immunomodulatory agent(s) together with a delivery vehicle may enhance the efficacy of the vaccination. It may be beneficial to inject the mRNA vaccine intratumorally. Any of these methods may include intratumorally injecting an mRNA vaccine encoding a tumor-specific antigen and mRNA encoding one or more immunomodulatory agents; the mRNA encoding the tumor-specific antigen and the mRNA encoding one or more immunomodulatory agents may be encapsulated together with an amino-lipidated peptoid delivery vehicle.

A method of treatment (e.g., treatment of cancer) may include intratumorally injecting an mRNA vaccine encoding a tumor-specific antigen and mRNA encoding one or more immunomodulatory agents, wherein the mRNA treatment nanoparticle is encapsulated together with single delivery vehicle for both the tumor-specific mRNA antigen and the mRNA encoding one or more immunomodulatory agents.

These methods and compositions may include, as part of the mRNA treatment nanoparticle, mRNA directed including a tumor-specific antigen in which the tumor-specific antigen is expressed by the tumor into which the mRNA treatment nanoparticle is being injected. In some variations the tumor-specific antigen is specific to the tumor into which the mRNA treatment nanoparticle is being injected.

In any of these methods and compositions, the tumor-specific antigen may be an mRNA encoding one or more patient-specific antigens. The patient-specific antigen may be identified by identifying an aberrant protein (e.g., one which is modified as compared to corresponding somatic proteins, and/or is aberrantly expressed as compared to non-cancerous patient cells). In some variations the mRNA treatment nanoparticle comprises an mRNA encoding a plurality of patient-specific antigens. The mRNA treatment nanoparticle may include an mRNA encoding a shared tumor antigen. For example, in some variations, the mRNA may encode an antigen (e.g. peptide) that is identified from similar tumors that are not isolated from the patient.

The polynucleotide sequence of the tumor-specific antigen maybe modified as compared to the sequence as present in the patient (e.g., in the tumor). The polynucleotide sequence may be modified to enhance mRNA expression and/or prevent mRNA degradation. In some variations, the mRNA including the tumor-specific antigen may be modified to enhance presentation of the tumor-specific antigen(s) to provoke an immune response. For example, the tumor-specific antigen may be part of an mRNA scaffold that enhances presentation.

In general, the mRNA therapies described herein may advantageously include mRNA encoding two or more additional immunomodulatory agents; these immunomodulatory agents may be different from each other. As used herein, an immunomodulatory agent may include: a checkpoint inhibitor (e.g., a checkpoint inhibitor protein, such as an anti-PD-1 antibody, anti-PDL-1 antibody, anti-CTLA4, etc.), an immunosuppression antagonist, a pro-inflammatory agent, or combinations thereof.

Examples of checkpoint inhibitors include proteins that target and inhibit one or more immune system checkpoint proteins, for example, proteins that inhibit one more of CTLA4, PD-1, and PD-L1. In some variations the checkpoint inhibitor refers to a protein that inhibits CTLA-4. For example, a checkpoint inhibitor protein may include a protein that binds to CTLA-4, such as an antibody or antibody fragment, e.g., antigen-binding fragments (Fab), single chain variable fragments (scFv), aptamer, etc. Examples of anti-CTLA-4 proteins (e.g. antibodies, scFv, etc.) are described herein. An mRNA encoding an immunomodulatory agent encodes: anti-PD-L1 antibody (such as atezolizumab, avelumab, or durvalumab); an anti-CTLA-4 antibody (such as tremelimumab or ipilimumab); an anti-PD1 antibody (such as nivolumab or pembrolizumab), or combinations thereof. For example, in some variations, the mRNA encoding an immunomodulatory agent encodes an anti-CTLA-4 binding agent.

An immunosuppression antagonist may include a protein that prevents or limits immunosuppression, blocking a pathway for suppression of the immune system. For example, antagonists against Transforming Growth Factor Beta (TGF-β-RII) is a cytokine that may act as an immunosuppression antagonist. A pro-inflammatory agent typically induces an inflammatory response itself and may cause a local inflammation. For example, IL-12 is a pro-inflammatory molecule.

Thus, as used herein, an immunomodulatory agent (immunomodulator) may include interleukins (e.g., IL-2, IL-7, IL-12) and other cytokines (interferons, GM-CSF), chemokines (CCL3, CCL26, CXCL-7), or the like.

In particular, described herein are methods and compositions including mRNA encoding a TGF-β antagonist (e.g., TGF-β RII). In some variations the mRNA encoding an immunomodulatory agent encodes a single chain interleukin-12 (IL-12).

In any of these methods and compositions described herein the mRNA treatment nanoparticle may include an immunostimulator, such as a CpG oligodeoxynucleotides. Immunostimulators may be distinct from immunomodulators as described herein. An immunostimulator may refer to non-protein immunostimulators, whereas the immunomodulators referred to herein are protein (e.g., peptide-based) immunomodulators that may be encoded as mRNA as part of the mRNA vaccine.

The use of mRNAs for both the tumor-specific antigen(s) and the immunomodulator when injected intratumorally, may provide numerous benefits. For example, although mRNAs when directly injected into the body (including into tumors) as described herein may have a half-life of about 3 days, providing a significant amount of transcription, sufficient to evoke a substantial and specific immune response as described in greater detail herein.

The methods described herein may be performed as part of an intratumoral injection treatment that may include one or more than one injection over a treatment period. For example, the methods described herein may include repeating the intratumoral injection treatment one or more times (e.g., about 1×, about 2×, about 3×, about 4×, about 5×, about 6×, about 7×, or more) with an about 1 to about 30 day wait between treatments (e.g., waiting between about 1 day and about 3 days, between about 1 day and 5 days, between about 1 day and 7 days, between about 1 day and 8 days, between about 1 day 10 days, between about 1 day and 15 days, between about 1 day and 20 days, between about 1 day and 30 days, etc.). In one example, the wait time may be about 1 day, about 2 days, about 3 days, about 4 days, about 5 days, about 6 days, about 7 days, about 8 days, about 9 days, about 10 days, about 11 days, about 12 days, about 13 days, or about 14 days; other suitable values within any of the aforementioned ranges are possible. A single treatment may include one or more injections, including injection into one or more sites in a single tumor or one or more sites in multiple tumors. For example, the methods described herein may include injection into a principal tumor. Injection may be into the body of the tumor, and/or the tissue surrounding a tumor. In some variations injection may be through a vessel feeding the tumor (e.g., blood vessel, etc.).

The methods described herein may include injection into any appropriate tumor type, including tumors or pre-tumoral lesions associated with one or more of: Acute Lymphoblastic Leukemia (ALL); Acute Myeloid Leukemia (AML); Adrenocortical Carcinoma; Anal Cancer; Appendix Cancer; Astrocytomas; Atypical Teratoid/Rhabdoid Tumor; Atypical Teratoid/Rhabdoid Tumor; Basal Cell Carcinoma of the Skin; Bile Duct Cancer; Bladder Cancer; Bone Cancer (includes Ewing Sarcoma and Osteosarcoma and Malignant Fibrous Histiocytoma); Brain Tumors; Breast Cancer; Bronchial Tumors (Lung Cancer); Burkitt Lymphoma; Carcinoid Tumor (Gastrointestinal); Cardiac (Heart) Tumors; Cervical Cancer; Childhood Extracranial Germ Cell Tumors; Childhood Rhabdomyosarcoma (Soft Tissue Sarcoma); Childhood Vascular Tumors (Soft Tissue Sarcoma); Cholangiocarcinoma; Chordoma; Chronic Lymphocytic Leukemia (CLL); Chronic Myelogenous Leukemia (CML); Chronic Myeloproliferative Neoplasms; Colorectal Cancer; Craniopharyngioma; Cutaneous T-Cell Lymphoma; Ductal Carcinoma In Situ (DCIS); Embryonal Tumors, Medulloblastoma; Endometrial Cancer (Uterine Cancer); Ependymoma; Esophageal Cancer; Esthesioneuroblastoma (Head and Neck Cancer); Ewing Sarcoma (Bone Cancer); Ewing Sarcoma (Bone Cancer); Extracranial Germ Cell Tumor; Extragonadal Germ Cell Tumor; Extragonadal Germ Cell Tumors; Eye Cancer; Fallopian Tube Cancer; Fibrous Histiocytoma of Bone, Malignant, and Osteosarcoma; Gallbladder Cancer; Gastric (Stomach) Cancer; Gastrointestinal Carcinoid Tumor; Gastrointestinal Stromal Tumors (GIST) (Soft Tissue Sarcoma); Germ Cell Tumor; Germ Cell Tumors; Gestational Trophoblastic Disease; Hairy Cell Leukemia; Head and Neck Cancer; Hepatocellular (Liver) Cancer; Histiocytosis, Langerhans Cell; Hodgkin Lymphoma; Hypopharyngeal Cancer; Hypopharyngeal Cancer (Head and Neck Cancer); Intraocular Melanoma; Intraocular Melanoma; Islet Cell Tumors, Pancreatic Neuroendocrine Tumors; Kaposi Sarcoma (Soft Tissue Sarcoma); Kaposi Sarcoma (Soft Tissue Sarcoma); Kidney (Renal Cell) Cancer; Langerhans Cell Histiocytosis; Laryngeal Cancer (Head and Neck Cancer); Leukemia; Lip and Oral Cavity Cancer (Head and Neck Cancer); Liver Cancer; Lung Cancer (Non-Small Cell, Small Cell, Pleuropulmonary Blastoma, and Tracheobronchial Tumor); Lymphoma; Malignant Fibrous Histiocytoma of Bone and Osteosarcoma; Medulloblastoma and Other CNS Embryonal Tumors; Melanoma; Merkel Cell Carcinoma (Skin Cancer); Mesothelioma, Malignant; Metastatic Cancer; Metastatic Squamous Neck Cancer with Occult Primary (Head and Neck Cancer); Mouth Cancer (Head and Neck Cancer); Multiple Endocrine Neoplasia Syndromes; Multiple Myeloma/Plasma Cell Neoplasms; Mycosis Fungoides (Lymphoma); Myelodysplastic Syndromes, Myelodysplastic/Myeloproliferative Neoplasms; Myelogenous Leukemia, Chronic (CML); Myeloid Leukemia, Acute (AML); Myeloproliferative Neoplasms, Chronic; Nasal Cavity and Paranasal Sinus Cancer (Head and Neck Cancer); Nasopharyngeal Cancer; Nasopharyngeal Cancer (Head and Neck Cancer); Neuroblastoma; Non-Hodgkin Lymphoma; Non-Small Cell Lung Cancer; Oral Cancer, Lip and Oral Cavity Cancer and Oropharyngeal Cancer (Head and Neck Cancer); Oropharyngeal Cancer; Osteosarcoma (Bone Cancer); Osteosarcoma and Malignant Fibrous Histiocytoma of Bone; Ovarian Cancer; Ovarian Germ Cell Tumors; Pancreatic Cancer; Pancreatic Neuroendocrine Tumors (Islet Cell Tumors); Papillomatosis (Childhood Laryngeal); Paraganglioma; Paranasal Sinus and Nasal Cavity Cancer (Head and Neck Cancer); Parathyroid Cancer; Penile Cancer; Pharyngeal Cancer (Head and Neck Cancer); Pheochromocytoma; Pituitary Tumor; Plasma Cell Neoplasm/Multiple Myeloma; Pleuropulmonary Blastoma (Lung Cancer); Primary CNS Lymphoma; Primary Peritoneal Cancer; Prostate Cancer; Rectal Cancer; Renal Cell (Kidney) Cancer; Retinoblastoma; Retinoblastoma; Rhabdomyosarcoma, Childhood (Soft Tissue Sarcoma); Salivary Gland Cancer (Head and Neck Cancer); Sarcoma; Sézary Syndrome (Lymphoma); Skin Cancer; Small Cell Lung Cancer; Small Intestine Cancer; Soft Tissue Sarcoma; Soft Tissue Sarcoma; Squamous Cell Carcinoma of the Skin—see Skin Cancer; Squamous Neck Cancer with Occult Primary, Metastatic (Head and Neck Cancer); Stomach (Gastric) Cancer; Testicular Cancer; Throat Cancer (Head and Neck Cancer); Thymoma and Thymic Carcinoma; Thyroid Cancer; Tracheobronchial Tumors (Lung Cancer); Transitional Cell Cancer of the Renal Pelvis and Ureter (Kidney (Renal Cell) Cancer); Urethral Cancer; Uterine Cancer, Endometrial; Uterine Sarcoma; Uterine Sarcoma; Vaginal Cancer; and Vulvar Cancer.

For example, the methods described herein may be methods for treating Lymphoma. In some variations, the methods described herein may be used to treat cervical cancer, including pre-cancerous indications (e.g., cervical dysplasia).

In any of the methods described herein, the method may include injecting an mRNA treatment nanoparticle encoding both one or more immunomodulatory agent encapsulated together with an mRNA encoding a tumor-specific antigen by a single delivery vehicle molecule (e.g., an amino-lipidated peptoid delivery vehicle). In one example, the mRNA treatment nanoparticle may be injected intratumorally; alternatively or additionally, the mRNA treatment nanoparticles may be injected systemically or locally near the tumor or into a tumor-feeding vessel. Systemic injection may include intravenous injection, subcutaneous injection, intraperitoneal injection, intramuscular injection, etc.

In general, the delivery vehicles described herein may be any appropriate delivery vehicle, including, e.g., an amphipathic nanoparticle. In particular, the amphipathic nanoparticle may comprise an amino-lipidated peptoid delivery vehicle. For example, these delivery vehicles may be a lipid-containing amphipathic delivery vehicle that provides packaging and protection of mRNA cargos during circulation, avoid immune recognition, and may facilitate cellular uptake and release. Examples of these delivery vehicles may be found in international patent application, PCT/US19/53661, titled "LIPID NANOPARTICLE FORMULATIONS COMPRISING LIPIDATED CATIONIC PEPTIDE COMPOUNDS FOR NUCLEIC ACID DELIVERY", and filed on Sep. 27, 2019, and in international patent application PCT/US19/53655, titled "TERTIARY AMINO LIPIDATED CATIONIC PEPTIDES FOR NUCLEIC ACID DELIVERY" and filed on Sep. 27, 2019, each of which is herein incorporated by reference in its entirety. Multiple types of delivery vehicle molecules may be used, and each type may be loaded with (e.g., may encapsulate, etc.) both the mRNA encoding one or more tumor-specific antigen and mRNA encoding one or more immunomodulatory agents as described herein.

A peptoid-based lipid formulation may incorporate both cationic groups and lipid moieties onto an N-substituted peptide (i.e. peptoid) backbone. The delivery vehicle components may be commercially available monodispersed, fully-characterizable chemical entities. Delivery vehicle (DV) components are relatively rapidly mixed with the mRNA in a controlled ratio. Exposure of DV components to aqueous solution and interaction between cationic (+) lipids and anionic (−) mRNA may trigger particle formation. This process can be carried out (to control particle size and uniformity) by using a microfluidic device. For example, the mRNA may be dissolved in an acidic buffer (pH about 3-5) which may help ensure full protonation of basic functional groups (such as amines) on the delivery vehicle which are responsible for its cationic charge. The delivery vehicle may be dissolved in an aqueous-miscible organic solvent (e.g., ethanol), which facilitates the formation of nano-sized particles upon exposure to the aqueous cargo solution. Immediately after mixing, the solution pH may be stabilized by a neutral buffer. The resulting formulation can be stored at about 4° C. to about 8° C. for weeks or longer with no apparent loss of function. Alternatively, the formulation process can be performed just-in-time and at the point-of-care.

The present disclosure provides mRNA therapies for the treatment of cancer. The mRNA therapies of the disclosure are particularly well-suited for the treatment of cancer as the technology provides for the delivery of both tumor-specific antigen mRNA and one or more mRNA encoding immunomodulatory agent polypeptides (for example, oncology-related polypeptides, including checkpoint inhibitors, pro-inflammatory agents and antagonists of immunosuppression, and the like, useful in immuno-oncology ("IO")), allowing de novo synthesis of functional proteins within target cells, e.g., within target cells in tumors. These therapeutic mRNAs may have modified nucleotides to minimize unwanted immune activation (e.g., the innate immune response associated with in vivo introduction of foreign nucleic acids) and optimize the translation efficiency of mRNA to protein. Exemplary aspects of the disclosure feature therapeutic mRNAs having a combination of nucleotide modifications to reduce the innate immune response and sequence optimization, in particular, within the open reading frame (ORF) of therapeutic mRNAs encoding immune modulating polypeptides to enhance protein expression.

The mRNA treatment nanoparticle compositions described herein features delivery of mRNA(s) encoding both tumor-specific antigen mRNA and one or more mRNAs encoding immunomodulatory agent polypeptides via a lipid nanoparticle (LNP) delivery system, and in particular, encapsulated within a single delivery vehicle molecule (e.g., an amino-lipidated peptoid delivery vehicle). For example, the mRNA therapy technology described herein features delivery of tumor-specific antigen mRNA and one or more mRNA encoding immunomodulatory agent polypeptides into tumors an amino-lipidated peptoid delivery vehicle. The formulations described herein may have reduced immunogenicity associated with the in vivo administration.

The present disclosure features methods and compositions for treating cancer, in particular, immunotherapeutic methods and compositions. In some aspects, the disclosure features methods and compositions for treating cancer using both tumor-specific antigen mRNA and one or more mRNA encoding immunomodulatory agent polypeptides.

In some aspects, the present disclosure provides methods of reducing or decreasing the size of a tumor or inhibiting tumor growth in a subject in need thereof by intratumoral administering of tumor-specific antigen mRNA and one or more mRNA encoding immunomodulatory agent polypeptides, e.g., encapsulated together with a delivery vehicle molecule (e.g., an amino-lipidated peptoid delivery vehicle).

The tumor-specific antigen mRNA and one or more mRNA encoding immunomodulatory agent polypeptides may comprise at least one chemically modified nucleoside. In some examples, the at least one chemically modified nucleoside is selected from the group consisting of pseudouridine, N1-methylpseudouridine, 5-methylcytosine, 5-methoxyuridine, and a combination thereof.

In some aspects, the composition is administered to subjects in need thereof in combination with another cancer therapy. The tumor-specific antigen mRNA and one or more mRNA encoding immunomodulatory agent polypeptides may act, at least in part, to have one or more activities selected from the group consisting of: (a) priming dendritic cells; (b) promoting dendritic cell maturation; (c) promoting antigen presenting cell cytokine and/or chemokine production; (d) expanding or maintaining Th17 cells; (e) enhancing Th1 and/or Th9 differentiation; and (f) any combination of (a)-(f).

In general, the therapeutic use of any of the mRNA nanoparticles described herein may include administering the mRNA treatment nanoparticle, involving using at least the mRNA nanoparticles, to a subject in need thereof.

This disclosure may provide use of any of the foregoing or preceding compositions (e.g., tumor-specific antigen mRNA and one or more mRNA encoding immunomodulatory agent polypeptides) encapsulated in the same nanoparticle (e.g., lipid nanoparticles, such as an amino-lipidated peptoid delivery vehicle) as described herein in the manufacture of a medicament for treating or delaying progression of cancer in an individual, wherein the medicament comprises the composition or lipid nanoparticle and an optional pharmaceutically acceptable carrier, and wherein the treatment comprises administration of the medicament, and an optional pharmaceutically acceptable carrier.

In some aspects, the disclosure provides a kit comprising a container comprising a polynucleotide (e.g., an mRNA) composition of a tumor-specific antigen mRNA and one or more mRNA encoding immunomodulatory agent polypeptides both encapsulated by a delivery vehicle molecule (e.g., an amino-lipidated peptoid delivery vehicle) as described herein, and an optional pharmaceutically acceptable carrier, and a package insert comprising instructions for intratumoral administration (e.g., injection) of the composition for treating or delaying progression of cancer in an individual. In some aspects, the package insert further comprises instructions for administration of the composition by intratumoral injection in combination with injection in another site (e.g., systemic injection) for treating or delaying progression of cancer in an individual.

In yet other aspects, the disclosure provides a kit comprising a medicament comprising any of the foregoing or preceding compositions as described herein and an optional pharmaceutically acceptable carrier, and a package insert comprising instructions for intratumoral administration of the medicament alone or in combination with injection at a second (e.g., systemic) location, and an optional pharmaceutically acceptable carrier for treating or delaying progression of cancer in an individual. In some aspects, the kit further comprises a package insert comprising instructions for administration of the medicament for treating or delaying progression of cancer in an individual.

Other aspects of the disclosure relate to a composition comprising any of the foregoing or preceding tumor-specific antigen mRNA and one or more mRNA encoding immunomodulatory agent polypeptides encapsulated together in a single lipid nanoparticle (e.g., an amino-lipidated peptoid delivery vehicle) as described herein and an optional pharmaceutically acceptable carrier for use in treating or delaying progression of cancer in an individual, wherein the treatment comprises intratumoral administration of the tumor-specific antigen mRNA and one or more mRNA encoding immunomodulatory agent polypeptides in the same lipid nanoparticle in combination with a second composition, wherein the second composition comprises one or more mRNA encoding immunomodulatory agent polypeptides and a delivery vehicle molecule (e.g., one or more amino-lipidated peptoid delivery vehicles). The one or more mRNA encoding immunomodulatory agent polypeptides may be a checkpoint inhibitor polypeptide (e.g., an anti-PD-1 antibody, an anti-PDL-1 antibody, an anti-CTLA4 antibody, or a combination thereof), and an optional pharmaceutically acceptable carrier. In some aspects, the checkpoint inhibitor polypeptide inhibits PD1, PD-L1, CTLA4, or a combination thereof. In one example, the checkpoint inhibitor polypeptide is an antibody or a polynucleotide encoding the antibody. In one example, the antibody is an anti-CTLA4 antibody or antigen-binding fragment thereof that specifically binds CTLA4, an anti-PD 1 antibody or antigen-binding fragment thereof that specifically binds PD1, an anti-PD-L1 antibody or antigen-binding fragment thereof that specifically binds PD-L1, and a combination thereof. In one example, the anti-PD-L1 antibody is atezolizumab, avelumab, or durvalumab. In one example, the anti-CTLA-4 antibody is tremelimumab or ipilimumab. In one example, the anti-PD1 antibody is nivolumab or pembrolizumab.

The mRNA (e.g., the tumor-specific antigen mRNA and one or more mRNA encoding immunomodulatory agent polypeptides) includes at least one chemical modification. In one example, the chemical modification is selected from the group consisting of pseudouridine, N1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methyluridine, 5-methoxyuridine, and 2'-O-methyl uridine. In some aspects, the mRNA comprises at least one chemically modified nucleoside, wherein the at least one chemically modified nucleoside is selected from the group consisting of pseudouridine, N1-methylpseudouridine, 5-methylcytosine, 5-methoxyuridine, and a combination thereof. In some aspects, the at least one chemically modified nucleoside is N1-methylpseudouridine. In some aspects, the polynucleotide is a fully modified N1-methylpseudouridine mRNA. Additional chemical modifications are disclosed herein.

The composition may be formulated in a lipid nanoparticle carrier, and in particular in an amino-lipidated peptoid delivery vehicles. For example, a composition comprising a tumor-specific antigen mRNA and one or more mRNA encoding immunomodulatory agent polypeptides, as described herein, may be formulated such that all polynucleotides within the composition are carried by the same lipid nanoparticle carrier. The ratio of the tumor-specific antigen mRNA and one or more mRNA encoding immunomodulatory agent polypeptides may be selected to be, for example, about 1:1 (e.g., approximately equimolar), or may include an excess of tumor-specific antigen mRNA relative to mRNA encoding the immunomodulatory agent polypeptide (e.g., between >about 1:1 and about 1.5:1, 2:1, 2.5:1, 3:1, 3.5:1, 4:1, 5:1, 6:1, 7:1, 8:1, 9:1, 10:1, etc. or tumor-specific antigen mRNA: mRNA encoding the immunomodulatory agent polypeptide). Alternatively, the composition may include an excess of mRNA encoding the immunomodulatory agent polypeptide relative to tumor-specific antigen mRNA (e.g., mRNA encoding the immunomodulatory agent polypeptide: tumor-specific antigen mRNA of between >about 1:1 and about 1.5:1, 2:1, 2.5:1, 3:1, 3.5:1, 4:1, 5:1, 6:1, 7:1, 8:1, 9:1, 10:1, etc.). In variations in which multiple immunomodulatory agent polypeptides (e.g., more than one mRNA encoding the immunomodulatory agent polypeptide) is used, all components may be approximately equimolar (e.g., about 1:1:1, or about 1:1:1:1, etc., relative to the tumor-specific antigen mRNA) or one or more components may be in excess (e.g., the tumor-specific antigen mRNA may be in excess, alternatively the mRNA encoding the one or more immunomodulatory agent polypeptides may be in excess).

In another aspect, the methods described herein include methods of reducing or decreasing a size of a tumor or inhibiting a tumor growth in a subject in need thereof comprising administering to the subject any of the mRNA treatment nanoparticle compositions described herein. In general, the composition is administered intratumorally. In another example, the composition (or a second composition comprising mRNA encoding one or more immunomodulatory agent polypeptides and an amino-lipidated peptoid delivery vehicle) may be administered regionally (e.g., into the region in which the tumor is growing, for example the composition can be administered intraperitoneally for tumors in the peritoneal cavity), and/or systemically. In one example, the tumor is a Lymphoma. In some other examples, the tumor is a hepatocellular carcinoma. In another example, the tumor is an ovarian tumor, a colon tumor or a disseminated gastric tumor. Other suitable tumors and cancers for treatment are disclosed herein.

For example, described herein are methods, the method comprising: intratumorally injecting an mRNA nanoparticle comprising: (i) a first mRNA encoding a tumor-specific antigen; (ii) a second mRNA encoding an immunomodulatory agent; and (iii) a delivery vehicle molecule, wherein the first mRNA and the second mRNA are encapsulated together by the delivery vehicle molecule.

The tumor-specific antigen may comprise a viral antigen. The viral antigen may be associated with Human papillomavirus (HPV), Kaposi's sarcoma-associated herpesvirus (KSHV), Epstein-Barr virus (EBV), Merkel cell polyomavirus, Human cytomegalovirus (CMV), or any combination thereof. The tumor-specific antigen may comprise a neo-epitope. The tumor-specific antigen may comprise a patient-specific antigen. The tumor-specific antigen may comprise a plurality of patient-specific antigens. The tumor-specific antigen may comprise a shared tumor antigen.

The delivery vehicle molecule may comprise an amino-lipidated peptoid. The mRNA nanoparticle may further comprise a third mRNA encoding a second immunomodulatory agent. The mRNA nanoparticle may further comprise an immunomodulatory siRNA.

The second mRNA encoding the immunomodulatory agent may encode: a checkpoint inhibitor, an immunosuppression antagonist, a pro-inflammatory agent, or any combination thereof. The second mRNA encoding the immunomodulatory agent may encode a pro-inflammatory cytokine. The pro-inflammatory cytokine may be one of: (IL), IL-1, IL-2, IL-12, IL-17, IL-18, IFN-$\gamma$, and TNF-$\alpha$. The pro-inflammatory cytokine may be interleukin-12 (IL-12).

The second mRNA encoding the immunomodulatory agent may encode a tumor necrosis factor superfamily member 14 (TNFSF14). The second mRNA encoding the immunomodulatory agent may encode anti-CTLA-4. The second mRNA encoding the immunomodulatory agent may encode a TGF-beta antagonist.

The mRNA nanoparticle may further include an immunostimulator. The mRNA nanoparticle may further include an immunostimulator that comprises a CpG oligodeoxynucleotides. Any of these methods may further comprise repeating the intratumoral injection one or more times with a wait between injections, wherein the wait is between about 1 and about 14 days.

The first mRNA encoding the tumor-specific antigen and the second mRNA encoding the immunomodulatory agent may be on a single mRNA strand. The method may be a method of treating a patient having Lymphoma. The method may be a method of treating a patient having cervical cancer.

Also described herein are methods, the methods comprising: intratumorally injecting an mRNA nanoparticle into a patient in need thereof, the mRNA nanoparticle comprising: (i) a first mRNA encoding an antigen specific to cervical cancer; (ii) a second mRNA encoding an immunomodulatory agent comprising: a pro-inflammatory cytokine; and (iii) a delivery vehicle molecule, wherein the first mRNA and the second mRNA are encapsulated together by the delivery vehicle molecule.

Also described herein are mRNA treatment nanoparticles, the nanoparticles comprising: (i) a first mRNA encoding a tumor-specific antigen; (ii) a second mRNA encoding an immunomodulatory agent; and (iii) a delivery vehicle molecule, wherein the first mRNA and the second mRNA are encapsulated together by the delivery vehicle molecule.

An mRNA treatment nanoparticle, the nanoparticle may comprise: (i) a first mRNA encoding a tumor-specific antigen; (ii) a second mRNA encoding an immunomodulatory agent that is at least about 80% identical to the nucleotide sequence of SEQ ID NO: 5; and (iii) a delivery vehicle molecule comprising an amino-lipidated peptoid delivery vehicle, wherein the first mRNA and the second mRNA are encapsulated together by the delivery vehicle molecule.

In some examples, an mRNA treatment nanoparticle, the nanoparticle may comprise: (i) a first mRNA encoding an antigen specific to cervical cancer; (ii) a second mRNA encoding an immunomodulatory agent comprising: a pro-inflammatory cytokine; and (iii) a delivery vehicle molecule, wherein the first mRNA and the second mRNA are encapsulated together by the delivery vehicle molecule.

The delivery vehicle molecule may comprise an amino-lipidated peptoid. The first mRNA may encode a patient-specific antigen. The first mRNA may encode a plurality of patient-specific antigens. The first mRNA may encode a shared tumor antigen. The second mRNA may encode: a checkpoint inhibitor, an immunosuppression antagonist, a pro-inflammatory agent, or any combination thereof. The second mRNA may encodes an anti-CTLA-4. The second mRNA may encode an anti-CTLA-4 that is at least about 80% identical to the nucleotide sequence of SEQ ID No: 1 or SEQ ID NO: 3.

Any of these mRNA treatment nanoparticle may further comprise a third mRNA that encodes a tumor necrosis factor superfamily member 14 (TNFSF14).

The mRNA treatment nanoparticle may further include a third mRNA that encodes a TGF-beta antagonist that is at least about 80% identical to the nucleotide sequence of SEQ ID NO: 7 or SEQ ID NO: 9. The second mRNA may encode an interleukin-12 that is at least about 80% identical to the nucleotide sequence of SEQ ID NO: 5. The mRNA treatment nanoparticle may further include an immunostimulator. The immunostimulator may comprise a CpG oligodeoxynucleotide.

In any of the mRNA treatment nanoparticles, respective open reading frames (ORFs) of the tumor-specific antigen and the immunomodulatory agent may be part of a single mRNA strand. Respective open reading frames (ORFs) of the tumor-specific antigen and the immunomodulatory agent may be part of different mRNA strands.

Also described herein are methods, the methods comprising: performing in vitro transcription of a first mRNA encoding a tumor-specific antigen from a template in a microfluidic path device; purifying the first mRNA; performing in vitro transcription of a second mRNA encoding a first immunomodulatory agent in the microfluidic path device; purifying the second mRNAs in the microfluidic path device; and encapsulating together the first mRNA and the second mRNA with a delivery vehicle molecule in the microfluidic path device to form an mRNA treatment nanoparticle.

For example, described herein are methods, the methods including: performing in vitro transcription of a first mRNA encoding a tumor-specific antigen from a template in a first chamber of a microfluidic path device; purifying the first mRNA; performing in vitro transcription of a second mRNA encoding a first immunomodulatory agent in a second chamber of the microfluidic path device; purifying the second mRNAs in the microfluidic path device; performing in vitro transcription of a third mRNA encoding a second immunomodulatory agent in a third chamber of the microfluidic path device; purifying the third mRNAs in the microfluidic path device; and encapsulating together the first mRNA, the second mRNA and the third mRNA with a delivery vehicle molecule in the microfluidic path device to form an mRNA treatment nanoparticle.

Each of: purifying the first mRNA, purifying the second mRNA and purifying the third mRNA may further comprise purifying in one or more reactors on the microfluidic path device.

Purifying in the one or more reactors may comprise removing double stranded mRNA using cellulose within the one or more reactors. The microfluidic path device may comprise a closed-path system to automatically and continuously perform in vitro transcription of each of the first mRNA and the second mRNA, purify the first mRNA and the second mRNA, and combine the first mRNA and the second mRNA with the delivery vehicle molecule. The closed-path system may pneumatically control performing in vitro transcription of first and second mRNA, purifying the first and second mRNA, and combining the first and second mRNA with the delivery vehicle molecule.

The closed-path system may pneumatically control: performing in vitro transcription of first mRNA and the second mRNA, purifying the first mRNA and the second mRNA, and combining the first mRNA and the second mRNA with the delivery vehicle molecule, by deflecting one or more membranes within the microfluidic path device.

The closed-path system may automatically and continuously: perform in vitro transcription of the therapeutic mRNA, purify the therapeutic mRNA, and combine the mRNA with a delivery vehicle, collectively in less than about 5 days. The method may be performed at a site of care. Combining the mRNA with the delivery vehicle may further comprise dialyzing the mRNA treatment nanoparticle in the microfluidic path device. Any of these methods may include concentrating the mRNA treatment nanoparticle on the microfluidic path device.

The delivery vehicle molecule may comprise an amphipathic molecule. The amphipathic molecule may comprise an amino-lipidated peptoid. The first mRNA may encode the tumor-specific antigen comprising an mRNA encoding a patient-specific antigen. The mRNA may encode a plurality of patient-specific antigens. The second mRNA may encode the immunomodulatory agent encodes: a checkpoint inhibitor, an immunosuppression antagonist, a pro-inflammatory agent, or any combination thereof. The second mRNA may encode an immunomodulatory agent encodes anti-CTLA-4. The second mRNA may encode an immunomodulatory agent encodes a TGF-beta antagonist. The second mRNA may encode an immunomodulatory agent encodes a single chain interleukin-12 (IL-12).

Any of these methods may include combining the first mRNA and the second mRNA comprises adding an immunostimulator in the microfluidic path device. The immunostimulator may comprise a CpG oligodeoxynucleotides.

Also described herein are microfluidic path devices comprising: an elastic layer sandwiched between a first surface and a second surface; a template in vitro transcription (IVT) chamber formed between the first surface and the second surface, wherein a portion of the elastic layer divides the template IVT chamber into a fluid-contacting side in the second surface and a pressure-receiving side in the first surface, wherein the fluid-contacting side of the template IVT chamber is in fluid communication with a source of an mRNA template encoding a tumor-specific antigen; a first reactor in fluid communication with the fluid-contacting side of the template IVT chamber, the first reactor including a double-stranded mRNA binding material within the first reactor to remove double stranded mRNA; a mixing assembly in fluid communication with the first reactor, with a source of a first immunomodulator mRNA, and with a delivery vehicle port to couple to a source of a delivery vehicle molecule to encapsulate together the first mRNA and the second mRNA with the delivery vehicle molecule to form an mRNA treatment nanoparticle; and a plurality of pressure channels each extending from a one or more pressure ports, through the first surface and the elastic layer, into the second surface and back through the elastic layer into the first surface, wherein each pressure channel of the plurality of pressure channels fluidly connects with the pressure-receiving side of the template IVT chamber, further wherein the volume of the fluid-contacting side of the template IVT chamber may be adjusted by applying pressure from the one or more of the pressure ports to drive fluid through the microfluidic path device to form the mRNA treatment nanoparticle.

Also described herein are microfluidic path devices comprising: an elastic layer sandwiched between a first surface and a second surface; a template in vitro transcription (IVT) chamber formed between the first surface and the second surface, wherein a portion of the elastic layer divides the template IVT chamber into a fluid-contacting side in the second surface and a pressure-receiving side in the first surface, wherein the fluid-contacting side of the template IVT chamber is in fluid communication with a source of a first mRNA template encoding a tumor-specific antigen; a first reactor in fluid communication with the fluid-contacting side of the template IVT chamber, the first reactor including a double-stranded mRNA binding material within the first reactor to remove double stranded mRNA; a first immunomodulator IVT chamber formed between the first surface and the second surface, wherein a portion of the elastic layer divides the first immunomodulator IVT chamber into a fluid-contacting side in the second surface and a pressure-receiving side in the first surface, wherein the fluid-contacting side of the first immunomodulator IVT chamber is in fluid communication with a source of a first immunomodulator template encoding a first immunomodulator; a second reactor in fluid communication with the fluid-contacting side of the first immunomodulator IVT chamber, the second reactor including a double-stranded mRNA binding material within the first reactor to remove double stranded mRNA; a first mixing chamber in fluid communication with the first reactor and the second reactor; a second mixing camber in fluid communication with an output of the first mixing chamber and a delivery vehicle port to couple to a source of a delivery vehicle molecule to encapsulate together the first mRNA and the second mRNA with the delivery vehicle molecule to form an mRNA treatment nanoparticle; and a plurality of pressure channels each extending from a one or more pressure ports, through the first surface and the elastic layer, into the second surface and back through the elastic layer into the first surface, wherein each pressure channel of the plurality of pressure channels fluidly connects with the pressure-receiving side of the template IVT chamber and the first immunomodulator IVT chamber, further wherein the volumes of the fluid-contacting side of the template IVT chamber and the fluid-contacting side of the first immunomodulator IVT chamber may be adjusted by applying pressure from the one or more of the pressure ports.

Also described herein are methods, the methods comprising: injecting an mRNA nanoparticle comprising: (ii) a first mRNA encoding a tumor-specific antigen; (ii) a second mRNA encoding an immunomodulatory agent; and (iii) a delivery vehicle molecule, wherein the first mRNA and the second mRNA are encapsulated together by the delivery vehicle molecule.

For example, a method may include: injecting an mRNA nanoparticle into a patient in need thereof, the mRNA nanoparticle comprising: (i) a first mRNA encoding an antigen specific to cervical cancer; (ii) a second mRNA encoding an immunomodulatory agent comprising: a proinflammatory cytokine; and (iii) a delivery vehicle molecule, wherein the first mRNA and the second mRNA are encapsulated together by the delivery vehicle molecule. Injecting is not limited to intratumoral injection, and may include, for example, intramuscular injection.

It should be appreciated that all combinations of the foregoing concepts and additional concepts discussed in greater detail below (provided such concepts are not mutually inconsistent) are contemplated as being part of the inventive subject matter disclosed herein and may be employed to achieve the benefits described herein.

BRIEF DESCRIPTION OF THE DRAWINGS

A better understanding of the features and advantages of the methods and apparatuses described herein will be obtained by reference to the following detailed description that sets forth illustrative examples, and the accompanying drawings of which:

FIG. 2 shows Kaplan Meier Survival curves for negative control (G1), subcutaneous injection of an mRNA of a tumor-specific antigen in an amino-lipidated peptoid delivery vehicle concurrent with intratumoral injection of a mRNA encoding an immunomodulatory agent (anti-CTLA-4) (G5), intratumoral injection of an mRNA vaccine including an mRNA of the tumor-specific antigen and mRNA encoding an immunomodulatory agent (anti-CTLA-4) in an amino-lipidated peptoid delivery vehicle (G6), and an mRNA vaccine including mRNA of the tumor-specific antigen and mRNA encoding two immunomodulatory agents (anti-CTLA-4 and TGF-β) in an amino-lipidated peptoid delivery vehicle (G7).

FIG. 3 shows Kaplan Meier Survival curves for a mouse tumor model, comparing negative control (G2), subcutaneous injection of an mRNA of a tumor-specific antigen (m4) in an amino-lipidated peptoid delivery (G7), intratumoral injection of an mRNA vaccine including mRNA of the tumor specific antigen (m4) and an mRNA encoding an immunomodulatory agent (anti-CTLA-4) in an amino-lipidated peptoid delivery vehicle (G9), and intratumoral injection of an mRNA vaccine including an mRNA of the tumor-specific antigen (m4) and mRNA encoding three immunomodulatory agents (anti-CTLA-4 and TGF-β and single chain IL-12, G10) in an amino-lipidated peptoid delivery vehicle.

FIG. 8A shows examples of EliSpot assays run with $3\times10^5$ splenocytes/well and tumor cells (EG. 7, $1\times10^6$) used as a stimulant. PMA/Ionomycin was used as a non-specific stimulant. Cells were incubated for 18 hours before analysis. FIG. 8B is a graph showing the quantification of this assay, counting CD8+ effector T-cells specific for tumor antigens. OTI (positive control) is compared to a negative control (#596) and two surviving mice (mouse #662 and mouse #670).

FIGS. 10A-10G illustrate the results of different nanoparticle compositions (as described in FIG. 9) intramuscularly injected in a mouse lymphoma tumor model at day 11.

FIG. 30A shows the effect of a nanoparticle composition of a tumor-specific antigen (HPV16 E6E7) mRNA with an immunomodulator (pro-inflammatory cytokine IL-12) mRNA.

FIG. 30B shows the effect of a nanoparticle composition of a tumor-specific antigen (HPV16) mRNA, a first immunomodulator (TNFSF14) mRNA and a second immunomodulator (pro-inflammatory cytokine IL-12) mRNA. FIG. 30C shows the effect of a nanoparticle composition of a tumor-specific antigen (HPV16) mRNA and an immunostimulator (CpG). FIG. 30D shows the effect of a nanoparticle composition of an immunomodulator (pro-inflammatory cytokine IL-12) mRNA alone (without tumor antigen). FIG. 30E shows the effect of a nanoparticle composition of a first immunomodulator (TNFSF14) mRNA and a second immunomodulator (pro-inflammatory cytokine IL-12) mRNA (without a tumor antigen). FIG. 30F shows the effect of an immunostimulator (CpG) alone (without tumor antigen).

FIGS. 31A-31B shows the time course of tumor growth following intramuscular injection with one of the nanoparticle compositions described herein on C3.43 tumors. FIG. 31A shows the effect of a nanoparticle composition of a tumor-specific antigen (HPV16 E6E7) mRNA with an immunomodulator (pro-inflammatory cytokine IL-12) mRNA. FIG. 31B shows the control (untreated) effect.

FIG. 32 is a graph of the probability of survival of mice having C3.43 tumors following treatment (e.g., intratumoral or intramuscular injection) with a nanoparticle composition as described herein.

DETAILED DESCRIPTION

Figure 1A:
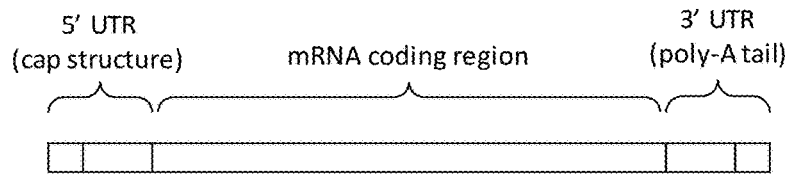
FIG. 1A is a schematic illustration on one example of an mRNA that may be used as part of an mRNA treatment nanoparticle as described herein.

The methods and compositions describe herein provide improved therapies for the treatment of diseases or disorders, including cancer. The therapies described herein may comprise one or more polynucleotides encoding a tumor-specific antigen and one or polynucleotides encoding an immunomodulator. The polynucleotide may be an RNA, such as an mRNA. For example, described herein are mRNA therapies that may be used for treatment, methods of forming them, and methods of using them. Any of the mRNA therapies described herein may be mRNA vaccines. These methods may include intratumorally injecting an mRNA treatment nanoparticle comprising mRNA treatment nanoparticles each including an mRNA encoding a tumor-specific antigen together with an mRNA encoding one or more immunomodulatory agents, wherein the mRNA for the tumor-specific antigen and the mRNA for the one or more immunomodulatory agent(s) are encapsulated together with a single delivery vehicle molecule, such as (but not limited to) an amino-lipidated peptoid delivery vehicle. The tumor-specific antigens may be directed against patient-specific antigens and/or shared tumor antigens. In one example, these improved vaccinations may result in durable tumor regression and long term CD8+ T-cell mediated cancer immunity. Although the mRNA vaccines with one or more amino-lipidated peptoid delivery vehicles alone can have a therapeutic effect, the addition of immunomodulating molecules enhance therapeutic efficacy.

As described in greater detail herein, whereas vaccination against tumor specific antigens can result in tumor regression, a single intratumoral injection of an mRNA treatment nanoparticle including an mRNA of a tumor-specific antigen, plus one or more mRNAs encoded immunomodulating molecules (such as, e.g., a checkpoint inhibitor antibody) encapsulated within an amino-lipidated peptoid delivery vehicle, may improves survival. Examples of immunomodulating molecules may include, but are not limited to, checkpoint inhibitor antibodies such as anti-CTLA-4 reagent encoded as mRNA.

Inclusion of additional mRNA encoded immunomodulators may improve the long-term survival. This is described in detail below (see, e.g., FIGS. 2-7) for a Syngeneic mouse cancer model. mRNA-encoded immunomodulators used in these experiments included a TGF-beta antagonist and a single chain interleukin-12, in some cases in addition to a checkpoint inhibitor (e.g., anti-CTLA-4). In these experiments, mice that are long-term survivors develop strong and persistent CD8+ effector T-cell cancer immunity and are resistant to further tumor challenges.

In general, mRNA-based tumor vaccination in combination with mRNA-based effector molecules can be performed against patient-specific tumor antigens, such as using one or more neo-epitopes. Neo-epitopes may be identified, for example, by sequencing a tumor (e.g., in one example, an MC38 tumor), and thus the neo-epitopes are tumor-specific antigens. Any patient-specific cancer neo-epitopes may be used.

mRNA based tumor vaccination in combination with mRNA-based effector molecules (e.g., immunomodulators) can be performed against shared antigens, such as antigens that are overexpressed and HLA-presented in tumors from different patients. mRNA vaccines as described herein may be formulated into nanoparticles using one or more amino-lipidated peptoids. "Nanoparticle" herein may refer to a particle having a size, referring to its largest dimension, in the nanometer range. The nanoparticle may have any suitable geometry, including spheres, ovals, cubes, or a regular or irregular geometrical shape. Depending on the geometry, the dimension may refer to length, width, diameter, etc. The nanoparticle may have a size less than about 1000 nm—e.g., less than about 500 nm, about 300 nm, about 200 nm, about 100 nm, about 80 nm, about 50 nm, about 40 nm, about 30 nm, about 20 nm, or smaller. In one example, the nanoparticle has a size between about 1 nm and about 1000 nm—e.g., between about 5 nm and about 800 nm, between about 10 nm and about 500 nm, between about 15 nm and about 300 nm, between about 20 nm and about 200 nm, between about 30 nm and about 100 nm, between about 40 nm and about 80 nm, between about 50 nm and about 70 nm, etc. In one example, the nanoparticle has a size between about 40 nm and about 70 nm. Other suitable particle sizes are also possible. The amino-lipidated peptoid may act as delivery vehicles and in combination with the mRNA vaccine may provide a high-expression in the tumor microenvironment. Thus, the mRNA vaccines described herein including mRNA encoding one or more tumor-specific antigen and mRNA encoding one or more immunomodulators can be co-formulated into single nanoparticle resulting in surprisingly high expression levels and high vaccination efficacy. Any of these treatments may include mRNA vaccines formulated into nanoparticles with a delivery vehicle optimized for high vaccination efficacy (e.g., the amino-lipidated peptoids). As mentioned, the therapeutic mRNAs described herein may include a tumor-specific antigen mRNA and one or more immunomodulatory agent mRNAs; the particular immunomodulatory agent mRNAs may be encapsulating together with the tumor-specific antigen mRNA in the same delivery vehicle.

In general, the mRNA included in the mRNA vaccine may be encoded in a construct or scaffold that assists in presenting the antigen. For example, FIG. 1A schematically illustrates one example of a generic mRNA scaffold. In FIG. 1A, the mRNA consists of different in cis-acting elements from 5' to 3': cap structure, 5'UTR, coding region (which may potentially include modified nucleotides), 3' UTR and a poly-A tail. In this example, the template for in vitro transcription of mRNA consists of cis-acting structural elements, namely from 5' to 3' end: (i) a cap structure, (ii) a 5' untranslated region (UTR), (iii) a coding (e.g., optimized codons) sequence, (iv) a 3' UTR and (v) a stretch of repeated adenine nucleotides (polyA tail). The cap structure and the poly-A tail length may be optimized. These cis-acting structural elements may be optimized for antigen presentation. The poly-A-tail and the cap structure are important for the efficient translation of the mRNA and to stabilize the mRNA against decay, while the UTR's in some instances control the translation and half-life of the mRNA. General production specifics such as purity and incorporation of modified nucleosides (e.g., 5' methoxy Uridine, 5 moU), may alter the immunogenicity of the mRNA itself and may significantly increase the translation efficiency. FIG. 1C shows an example in which the mRNA strand includes both the tumor-specific antigen mRNA (e.g., one or more copies, and/or one or more tumor-specific antigens) and one or more immunomodulator mRNA ORFs.

Figure 1B:
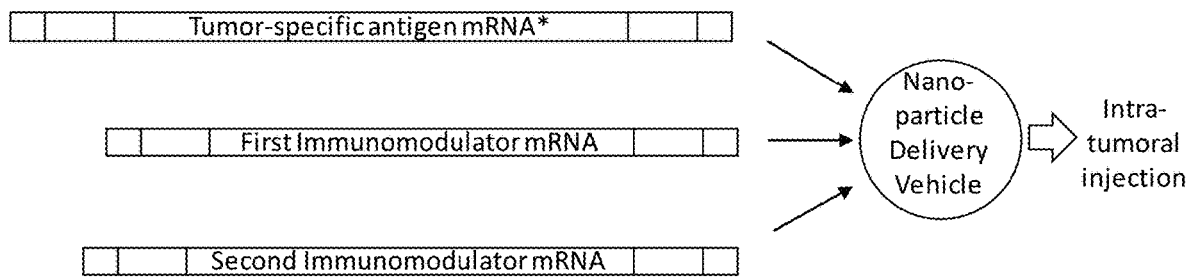
FIG. 1B schematically illustrates one example of a method for forming an mRNA treatment nanoparticle as described herein.
Figure 1C:
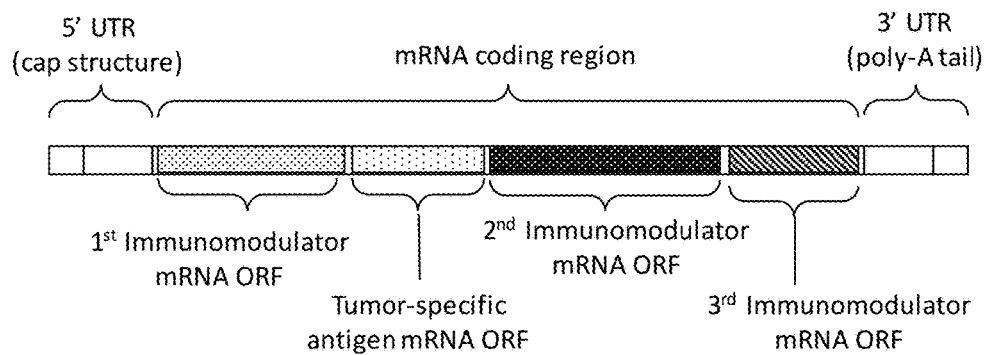
FIG. 1C schematically illustrates one example of an mRNA including multiple mRNA open reading frames enclosing a tumor-specific antigen and multiple immunomodulator mRNAs.

FIG. 1B schematically illustrates one example of a method for improving the efficacy of an mRNA vaccine in the treatment of cancer. In FIG. 1B, the method includes intratumorally injecting an mRNA vaccine encoding a tumor-specific antigen (e.g., in a scaffold that enhances antigen presentation) and mRNAs encoding two or more immunomodulatory agents (e.g., first immunomodulator mRNA and second immunomodulator mRNA), encapsulated together by a single delivery vehicle molecule. For example, the at least one of the two (or more) immunomodulatory agents may be a checkpoint inhibitor (e.g., an anti-CTLA-4 mRNA). The mRNA vaccine and the immunomodulatory agent are encapsulated together with the delivery vehicle, which may be, for example, an amino-lipidated peptoid delivery vehicle.

FIG. 1C shows an alternative example in which a single mRNA strand includes a tumor-specific mRNA and mRNA encoding one or more immunomodulators (e.g., a first immunomodulator, a second immunomodulator, a third immunomodulator), so that the mRNA open reading frames (ORFs) encode the tumor-specific mRNA and the mRNAs for the immunomodulators. This single mRNA strand may be encapsulated within a delivery vehicle molecule.

The prevention or treatment of disease with substances that stimulate the immune response is generally referred to as immunotherapy. Immunotherapy, sometimes also referred to as immuno-oncology, introduces therapies that target not the tumor, but the host immune system. These therapies may possess unique pharmacological response profiles, and thus represent therapies that might cure many distinct types of cancer. In one example, cancers of the lungs, kidney, bladder and skin are among those that derive substantial efficacy from treatment with immuno-oncology in terms of survival or tumor response, as does, in particular, melanoma. Immunotherapy often features checkpoint inhibitor treatment with biologic drugs known as checkpoint inhibitor antibodies.

The present disclosure features methods and compositions for treating cancer, in particular, methods and compositions for improving or enhancing immunotherapeutic methods and compositions. In some aspects, the disclosure features methods and compositions for treating or preventing cancer using two or more polynucleotides (e.g., mRNAs) encoding (1) a tumor-specific antigen, including in particular a patient-specific tumor antigen (or antigens) and (2) one or more mRNAs encoding one or more immunomodulators (e.g., in some variations including a polypeptide comprising a checkpoint inhibitor polypeptide) encapsulated with a single delivery vehicle molecule. In some aspects, the disclosure provides an enhancement of an immunomodulatory composition comprising a polynucleotide encoding a patient-specific tumor antigen, and two or more immunomodulators encapsulated together with a single delivery vehicle molecule. In other aspects, the disclosure provides an immunomodulatory composition comprising a polynucleotide encoding a patient-specific tumor antigen, and two or more immunomodulators (e.g., anti-CTLA-4 and one or both: TGF-beta antagonist and single chain interleukin-12), encapsulated together with a single delivery vehicle molecule. The mRNA vaccine may include a mixture of these components in any appropriate and effective ratio.

In some aspects, the disclosure relates to methods of treating cancer using an mRNA of a patient-specific tumor antigen, and mRNA encoding two or more immunomodulators encapsulated together with a single delivery vehicle molecule. Without being bound in theory, administering, and specifically intratumorally administering, these mRNA vaccines may stimulate, for example, T-cells, natural killer cells, macrophages, and or dendritic cells. In some aspects, the immune therapeutic methods disclosed herein can (1) transform the tumor microenvironment (TME) to optimize immunogenicity, and/or (2) enhance T cell responses to elicit abscopal control and anti-cancer memory.

Other aspects of the disclosure feature compositions and methods of reducing or decreasing the size of a tumor, or inhibiting the growth of a tumor, in a subject in need thereof by administering to the subject an effective amount of a combination comprising mRNAs encoding a patient-specific tumor antigen, and mRNA encoding two or more immunomodulators encapsulated together with a single delivery vehicle molecule. The delivery vehicle molecule may be, for example, an amino lipidated peptide that may include tertiary amino lipidated cationic peptides, such as any of those described in PCT application, PCT/US19/53661, titled "LIPID NANOPARTICLE FORMULATIONS COMPRISING LIPIDATED CATIONIC PEPTIDE COMPOUNDS FOR NUCLEIC ACID DELIVERY", filed on Sep. 27, 2019, and in PCT/US19/53655, titled "TERTIARY AMINO LIPIDATED CATIONIC PEPTIDES FOR NUCLEIC ACID DELIVERY" filed on Sep. 27, 2019; both of these applications hereby incorporated by reference in its entirety.

These delivery vehicle molecules may comprise additional lipids/components. For example, the amino lipidated peptides can include one or more phospholipids, e.g., 1-Myristoyl-2-stearoyl-sn-glycero-3-phosphocholine (MSPC) or distearoylphosphatidylcholine (DSPC). The lipid composition can also comprise a quaternary amine compound such as N-[1-(2,3-Dioleoyloxy)propyl]-N,N,N-trimethylammonium methyl-sulfate (DOTAP).

The headings provided herein are not limitations of the various aspects or aspects of the disclosure, which can be defined by reference to the specification as a whole. Accordingly, the terms defined immediately below are more fully defined by reference to the specification in its entirety. Before describing the present disclosure in detail, it is to be understood that this disclosure is not limited to specific compositions or process steps, as such can vary.

I. Definitions

In order that the present disclosure can be more readily understood, certain terms are first defined. As used in this application, except as otherwise expressly provided herein, each of the following terms shall have the meaning set forth below. Additional definitions are set forth throughout the application.

The disclosure includes examples in which exactly one member of the group is present in, employed in, or otherwise relevant to a given product or process. The disclosure includes examples in which more than one, or all of the group members are present in, employed in, or otherwise relevant to a given product or process.

In this specification and the appended claims, the singular forms "a", "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Wherever aspects are described herein with the language "comprising," otherwise analogous aspects described in terms of "consisting of" and/or "consisting essentially of" are also provided.

Units, prefixes, and symbols are denoted in their Systeme International de Unites (SI) accepted form. Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the disclosure. Where a value is explicitly recited, it is to be understood that values which are about the same quantity or amount as the recited value are also within the scope of the disclosure. Where a combination is disclosed, each subcombination of the elements of that combination is also specifically disclosed and is within the scope of the disclosure. Conversely, where different elements or groups of elements are individually disclosed, combinations thereof are also disclosed. Where any element of a disclosure is disclosed as having a plurality of alternatives, examples of that disclosure in which each alternative is excluded singly or in any combination with the other alternatives are also hereby disclosed; more than one element of a disclosure can have such exclusions, and all combinations of elements having such exclusions are hereby disclosed.

Nucleotides are referred to by their commonly accepted single-letter codes. Unless otherwise indicated, nucleic acids are written left to right in 5' to 3' orientation. Nucleotides are referred to herein by their commonly known one-letter symbols recommended by the IUPAC-IUB Biochemical Nomenclature Commission. Accordingly, A represents adenine, C represents cytosine, G represents guanine, T represents thymine, and U represents uracil.

Amino acids are referred to herein by either their commonly known three letter symbols or by the one-letter symbols recommended by the IUPAC-IUB Biochemical Nomenclature Commission. Unless otherwise indicated, amino acid sequences are written left to right in amino to carboxy orientation.

The terms "substantially", "about", and "approximately" as used in connection with a numerical value throughout the specification and the claims denotes an interval of accuracy, accounting for small fluctuations. In general, such interval of accuracy is +10%. For example, they can refer to less than or equal to ±10%, such as less than or equal to ±5%, such as less than or equal to ±1%, such as less than or equal to ±0.5%, such as less than or equal to ±0.2%, such as less than or equal to ±0.1%, such as less than or equal to ±0.05%. In one example, these terms encompass no fluctuation, ±0.

Where ranges are given, endpoints are included. Furthermore, unless otherwise indicated or otherwise evident from the context and understanding of one of ordinary skill in the art, values that are expressed as ranges can assume any specific value or subrange within the stated ranges in different examples of the disclosure, to the tenth of the unit of the lower limit of the range, unless the context clearly dictates otherwise.

Administered in combination: As used herein, the term "administered in combination," "concurrent administration," combined administration," or "combination therapy" means that two or more agents are administered to a subject at the same time or within an interval such that there can be an overlap of an effect of each agent on the patient. In some examples, they are administered within less than or equal to about 60 minutes—e.g., less than or equal to about, 30, about 15, about 10, about 5, or about 1 minute, or less, of one another. In some examples, the administrations of the agents are spaced sufficiently closely together such that a combinatorial (e.g., a synergistic) effect is achieved.

The term "amino acid substitution" refers to replacing an amino acid residue present in a parent or reference sequence (e.g., a wild type sequence) with another amino acid residue. An amino acid can be substituted in a parent or reference sequence (e.g., a wild type polypeptide sequence), for example, via chemical peptide synthesis or through recombinant methods known in the art. Accordingly, a reference to a "substitution at position X" refers to the substitution of an amino acid present at position X with an alternative amino acid residue. In some aspects, substitution patterns can be described according to the schema AnY, wherein A is the single letter code corresponding to the amino acid naturally or originally present at position n, and Y is the substituting amino acid residue. In other aspects, substitution patterns can be described according to the schema An(YZ), wherein A is the single letter code corresponding to the amino acid residue substituting the amino acid naturally or originally present at position X, and Y and Z are alternative substituting amino acid residue.

In the context of the present disclosure, substitutions (even when they referred to as amino acid substitution) are conducted at the nucleic acid level, i.e., substituting an amino acid residue with an alternative amino acid residue is conducted by substituting the codon encoding the first amino acid with a codon encoding the second amino acid.

Animal: As used herein, the term "animal" refers to any member of the animal kingdom. In some examples, "animal" refers to humans at any stage of development. In some examples, "animal" refers to non-human animals at any stage of development. In certain examples, the non-human animal is a mammal (e.g., a rodent, a mouse, a rat, a rabbit, a monkey, a dog, a cat, a sheep, cattle, a primate, or a pig). In some examples, animals include, but are not limited to, mammals, birds, reptiles, amphibians, fish, and worms. In some examples, the animal is a transgenic animal, genetically-engineered animal, or a clone.

Associated with: As used herein with respect to a disease, the term "associated with" means that the symptom, measurement, characteristic, or status in question is linked to the diagnosis, development, presence, or progression of that disease. As association may, but need not, be causatively linked to the disease.

When used with respect to two or more moieties, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Sequence Optimization: The term "sequence optimization" refers to a process or series of processes by which nucleobases in a reference nucleic acid sequence are replaced with alternative nucleobases, resulting in a nucleic acid sequence with improved properties, e.g., improved protein expression or immunogenicity.

In general, the goal in sequence optimization is to produce a synonymous nucleotide sequence than encodes the same polypeptide sequence encoded by the reference nucleotide sequence. Thus, there are no amino acid substitutions (as a result of codon optimization) in the polypeptide encoded by the codon optimized nucleotide sequence with respect to the polypeptide encoded by the reference nucleotide sequence.

Codon substitution: The terms "codon substitution" or "codon replacement" in the context of sequence optimization refer to replacing a codon present in a reference nucleic acid sequence with another codon. A codon can be substituted in a reference nucleic acid sequence, for example, via chemical peptide synthesis or through recombinant methods known in the art. Accordingly, references to a "substitution" or "replacement" at a certain location in a nucleic acid sequence (e.g., an mRNA) or within a certain region or subsequence of a nucleic acid sequence (e.g., an mRNA) refer to the substitution of a codon at such location or region with an alternative codon.

As used herein, the terms "coding region" and "region encoding" and grammatical variants thereof, refer to an Open Reading Frame (ORF) in a polynucleotide that upon expression yields a polypeptide or protein.

A "conservative amino acid substitution" is one in which the amino acid residue is replaced with an amino acid residue having a similar side chain. Families of amino acid residues having similar side chains have been defined in the art, including basic side chains (e.g., lysine, arginine, or histidine), acidic side chains (e.g., aspartic acid or glutamic acid), uncharged polar side chains (e.g., glycine, asparagine, glutamine, serine, threonine, tyrosine, or cysteine), nonpolar side chains (e.g., alanine, valine, leucine, isoleucine, proline, phenylalanine, methionine, or tryptophan), beta-branched side chains (e.g., threonine, valine, isoleucine) and aromatic side chains (e.g., tyrosine, phenylalanine, tryptophan, or histidine). Thus, if an amino acid in a polypeptide is replaced with another amino acid from the same side chain family, the amino acid substitution is considered to be conservative. In another aspect, a string of amino acids can be conservatively replaced with a structurally similar string that differs in order and/or composition of side chain family members.

Non-conservative amino acid substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, His, Ile or Trp) is substituted for, or by, one having a smaller side chain (e.g., Ala or Ser) or no side chain (e.g., Gly).

Other suitable amino acid substitutions are also possible. For example, for the amino acid alanine, a substitution can be taken from any one of D-alanine, glycine, beta-alanine, L-cysteine and D-cysteine. For lysine, a replacement can be any one of D-lysine, arginine, D-arginine, homo-arginine, methionine, D-methionine, ornithine, or D-ornithine. Generally, substitutions in functionally important regions that can be expected to induce changes in the properties of isolated polypeptides are those in which (i) a polar residue, e.g., serine or threonine, is substituted for (or by) a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine. The likelihood that one of the foregoing non-conservative substitutions can alter functional properties of the protein is also correlated to the position of the substitution with respect to functionally important regions of the protein: some non-conservative substitutions can accordingly have little or no effect on biological properties.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some examples, two or more sequences are said to be "completely conserved" if they are 100% identical to one another. In some examples, two or more sequences are said to be "highly conserved" if they are at least about 70% identical—e.g., at least about 80% identical, at least about 90% identical, at least about 95% identical, or more, to one another. In some examples, two or more sequences are said to be "highly conserved" if they are about 70% identical, about 80% identical, about 90% identical, about 95%, about 98%, or about 99%, or more, identical to one another. In some examples, two or more sequences are said to be "conserved" if they are at least about 30% identical, at least about 40% identical, at least about 50% identical, at least about 60% identical, at least about 70% identical, at least about 80% identical, at least about 90% identical, or at least about 95% identical to one another. In some examples, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence may apply to the entire length of a polynucleotide or polypeptide or may apply to a portion, region or feature thereof.

Contacting: As used herein, the term "contacting" means establishing a physical connection between two or more entities. For example, contacting a mammalian cell with a nanoparticle composition means that the mammalian cell and a nanoparticle are made to share a physical connection. Methods of contacting cells with external entities both in vivo and ex vivo are well known in the biological arts. For example, contacting a nanoparticle composition and a mammalian cell disposed within a mammal may be performed by varied routes of administration (e.g., intravenous, intramuscular, intradermal, and subcutaneous) and may involve varied amounts of nanoparticle compositions. Moreover, more than one mammalian cell may be contacted by a nanoparticle composition.

Controlled Release: As used herein, the term "controlled release" refers to a pharmaceutical composition or compound release profile that conforms to a particular pattern of release to effect a therapeutic outcome.

Covalent Derivative: The term "covalent derivative" when referring to polypeptides include modifications of a native or starting protein with an organic proteinaceous or non-proteinaceous derivatizing agent, and/or post-translational modifications. Covalent modifications are traditionally introduced by reacting targeted amino acid residues of the protein with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays, or for the preparation of anti-protein antibodies for immunoaffinity purification of the recombinant glycoprotein. Such modifications are within the ordinary skill in the art and are performed without undue experimentation.

Cyclic or Cyclized: As used herein, the term "cyclic" refers to the presence of a continuous loop. Cyclic molecules need not be circular, only joined to form an unbroken chain of subunits. Cyclic molecules such as the engineered RNA or mRNA can be single units or multimers or comprise one or more components of a complex or higher order structure.

Cytotoxic: As used herein, "cytotoxic" refers to killing or causing injurious, toxic, or deadly effect on a cell (e.g., a mammalian cell (e.g., a human cell)), bacterium, virus, fungus, protozoan, parasite, prion, or a combination thereof.

Delivering: As used herein, the term "delivering" means providing an entity to a destination. For example, delivering a polynucleotide to a subject may involve administering a nanoparticle composition including the polynucleotide to the subject (e.g., by an intravenous, intramuscular, intradermal, or subcutaneous route). Administration of a nanoparticle composition to a mammal or mammalian cell may involve contacting one or more cells with the nanoparticle composition.

Delivery Vehicle: As used herein, "delivery vehicle" refers to any substance that facilitates, at least in part, the in vivo, in vitro, or ex vivo delivery of a polynucleotide to targeted cells or tissues (e.g., tumors, etc.). Referring to something as a delivery vehicle does not mean that it may not also have therapeutic effects.

Destabilized: As used herein, the term "destable," "destabilize," or "destabilizing region" means a region or molecule that is less stable than a starting, wild-type or native form of the same region or molecule.

Detectable label: As used herein, "detectable label" refers to one or more markers, signals, or moieties that are attached, incorporated or associated with another entity that is readily detected by methods known in the art including radiography, fluorescence, chemiluminescence, enzymatic activity, absorbance and the like. Detectable labels include radioisotopes, fluorophores, chromophores, enzymes, dyes, metal ions, ligands such as biotin, avidin, streptavidin and haptens, quantum dots, and the like. Detectable labels can be located at any position in the peptides or proteins disclosed herein. They can be within the amino acids, the peptides, or proteins, or located at the N- or C-termini.

Diastereomer: As used herein, the term "diastereomer," means stereoisomers that are not mirror images of one another and are non-superimposable on one another.

Digest: As used herein, the term "digest" means to break apart into smaller pieces or components. When referring to polypeptides or proteins, digestion results in the production of peptides.

Distal: As used herein, the term "distal" means situated away from the center or away from a point or region of interest.

Domain: As used herein, when referring to polypeptides, the term "domain" refers to a motif of a polypeptide having one or more identifiable structural or functional characteristics or properties (e.g., binding capacity, serving as a site for protein-protein interactions).

Dosing regimen: As used herein, a "dosing regimen" or a "dosing regimen" is a schedule of administration or physician determined regimen of treatment, prophylaxis, or palliative care.

Effective Amount: As used herein, the term "effective amount" of an agent is that amount sufficient to effect beneficial or desired results, for example, clinical results, and, as such, an "effective amount" depends upon the context in which it is being applied. For example, in the context of administering an agent that treats a tumor, an effective amount of an agent is, for example, an amount sufficient to reduce or decrease a size of a tumor or to inhibit a tumor growth, as compared to the response obtained without administration of the agent. The term "effective amount" can be used interchangeably with "effective dose," "therapeutically effective amount," or "therapeutically effective dose."

Enantiomer: As used herein, the term "enantiomer" means each individual optically active form of a compound of the disclosure, having an optical purity or enantiomeric excess (as determined by methods standard in the art) of at least about 80% (i.e., at least about 90% of one enantiomer and at most about 10% of the other enantiomer), at least about 90%, or at least about 98%, or higher.

Encapsulate: as used herein, the term "encapsulate," in reference to delivery vehicles interacting with mRNA, means to completely or partially enclose or encase; this may protect the mRNA from degradation and promote cellular uptake. This may include the mRNA by the encapsulating delivery vehicle. As used herein "encapsulated together" refers to two or more molecules, such as a first mRNA and the second mRNA that are encapsulated by the same delivery vehicle molecule. The first mRNA and the second mRNA may be encoded on different polynucleotide strands, or they may be part of the same strand. In some examples, multiple mRNAs of the same type may be encapsulated together in the same delivery vehicle molecule in a determined stoichiometry (e.g., 1:1, 1:2, 2:1, etc.).

Encapsulation Efficiency: As used herein, "encapsulation efficiency" refers to the amount of a polynucleotide that becomes part of a nanoparticle composition, relative to the initial total amount of polynucleotide used in the preparation of a nanoparticle composition. For example, if 97 mg of polynucleotide is encapsulated in a nanoparticle composition out of a total 100 mg of polynucleotide initially provided to the composition, the encapsulation efficiency may be given as 97%. As used herein, "encapsulation" may refer to complete, substantial, or partial enclosure, confinement, surrounding, or encasement. For example, encapsulation may refer about 80% or more encapsulated, about 85% or more encapsulated, about 90% or more encapsulated, about 95% or more encapsulated, or completely encapsulated.

Encoded protein cleavage signal: As used herein, "encoded protein cleavage signal" refers to the nucleotide sequence that encodes a protein cleavage signal.

Engineered: As used herein, examples of the disclosure are "engineered" when they are designed to have a feature or property, whether structural or chemical, that varies from a starting point, wild type or native molecule.

Enhanced Delivery: As used herein, the term "enhanced delivery" means delivery of more (e.g., at least about 1.5 fold more—e.g., at least about 2-fold more, at least 3-fold more, at least 4-fold more, at least 5-fold more, at least 6-fold more, at least 7-fold more, at least 8-fold more, at least 9-fold more, at least 10-fold more, or higher) of a polynucleotide by a nanoparticle to a target tissue of interest (e.g., mammalian liver tissue), compared to the level of delivery of a polynucleotide by a control nanoparticle to a target tissue of interest. The level of delivery of a nanoparticle to a particular tissue may be measured by comparing the amount of protein produced in a tissue to the weight of said tissue, comparing the amount of polynucleotide in a tissue to the weight of said tissue, comparing the amount of protein produced in a tissue to the amount of total protein in said tissue, or comparing the amount of polynucleotide in a tissue to the amount of total polynucleotide in said tissue. It will be understood that the enhanced delivery of a nanoparticle to a target tissue need not be determined in a subject being treated, it may be determined in a surrogate such as an animal model (e.g., a rat model).

Exosome: As used herein, "exosome" is a vesicle secreted by mammalian cells or a complex involved in RNA degradation.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Ex Vivo: As used herein, the term "ex vivo" refers to events that occur outside of an organism (e.g., animal, plant, or microbe or cell or tissue thereof). Ex vivo events may take place in an environment minimally altered from a natural (e.g., in vivo) environment.

Feature: As used herein, a "feature" refers to a characteristic, a property, or a distinctive element. When referring to polypeptides, "features" are defined as distinct amino acid sequence-based components of a molecule. Features of the polypeptides encoded by the polynucleotides of the present disclosure include surface manifestations, local conformational shape, folds, loops, half-loops, domains, half-domains, sites, termini or any combination thereof.

Formulation: As used herein, a "formulation" includes at least a polynucleotide and one or more of a carrier, an excipient, and a delivery agent.

Fragment: A "fragment," as used herein, refers to a portion. For example, fragments of proteins can comprise polypeptides obtained by digesting full-length protein isolated from cultured cells. In some examples, a fragment is a subsequence of a full-length protein (e.g., one of the subunits of IL-23) wherein N-terminal, and/or C-terminal, and/or internal subsequences have been deleted. In some aspects of the present disclosure, the fragments of a protein of the present disclosure are functional fragments.

Functional: As used herein, a "functional" biological molecule is a biological molecule in a form in which it exhibits a property and/or activity by which it is characterized. Thus, a functional fragment of a polynucleotide of the present disclosure is a polynucleotide capable of expressing a functional interleukin fragment. As used herein, a functional fragment of an interleukin refers to a fragment of a wild type interleukin (i.e., a fragment of a naturally occurring form of the interleukin), or a mutant or variant thereof, wherein the fragment retains a least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the biological activity of the corresponding full-length protein.

Homology: As used herein, the term "homology" refers to the overall relatedness between polymeric molecules, e.g. between nucleic acid molecules (e.g. DNA molecules and/or RNA molecules) and/or between polypeptide molecules. Generally, the term "homology" implies an evolutionary relationship between two molecules. Thus, two molecules that are homologous will have a common evolutionary ancestor. In the context of the present disclosure, the term homology encompasses both to identity and similarity.

In some examples, polymeric molecules are considered to be "homologous" to one another if at least about 25%, 30%, 35%, 40%, 45%, 50%, 55%, 60%, 65%, 70%, 75%, 80%, 85%, 90%, 95%, or 99% of the monomers in the molecule are identical (exactly the same monomer) or are similar (conservative substitutions). The term "homologous" necessarily refers to a comparison between at least two sequences (polynucleotide or polypeptide sequences).

Identity: As used herein, the term "identity" refers to the overall monomer conservation between polymeric molecules, e.g., between polynucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain examples, the length of a sequence aligned for comparison purposes is at least about 30%, at least about 40%, at least about 50%, at least about 60%, at least about 70%, at least about 80%, at least about 90%, at least about 95%, or about 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. When comparing DNA and RNA, thymine (T) and uracil (U) can be considered equivalent.

Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI).

Sequence alignments can be conducted using methods known in the art such as MAFFT, Clustal (ClustalW, Clustal X or Clustal Omega), MUSCLE, etc.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain aspects, the percentage identity "% ID" of a first amino acid sequence (or nucleic acid sequence) to a second amino acid sequence (or nucleic acid sequence) is calculated as % ID=100×(Y/Z), where Y is the number of amino acid residues (or nucleobases) scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

The generation of a sequence alignment for the calculation of a percent sequence identity is not limited to binary sequence-sequence comparisons exclusively driven by primary sequence data. It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity can be curated either automatically or manually.

Immune checkpoint inhibitor: An "immune checkpoint inhibitor" or simply "checkpoint inhibitor" refers to a molecule that prevents immune cells from being turned off by cancer cells. As used herein, the term checkpoint inhibitor refers to polypeptides (e.g., antibodies) or polynucleotides encoding such polypeptides (e.g., mRNAs) that neutralize or inhibit inhibitory checkpoint molecules such as cytotoxic T-lymphocyte-associated protein 4 (CTLA-4), programmed death 1 receptor (PD-1), or PD-1 ligand 1 (PD-L1).

Immune response: The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

Inflammatory response: "Inflammatory response" refers to immune responses involving specific and non-specific defense systems. A specific defense system reaction is a specific immune system reaction to an antigen. Examples of specific defense system reactions include antibody responses. A non-specific defense system reaction is an inflammatory response mediated by leukocytes generally incapable of immunological memory, e.g., macrophages, eosinophils and neutrophils. In some aspects, an immune response includes the secretion of inflammatory cytokines, resulting in elevated inflammatory cytokine levels.

Inflammatory cytokines: The term "inflammatory cytokine" refers to cytokines that are elevated in an inflammatory response. Examples of inflammatory cytokines include interleukin-6 (IL-6), CXCL1 (chemokine (C-X-C motif) ligand 1; also known as GROc, interferon-γ (IFNγ), tumor necrosis factor α (TNFα), interferon γ-induced protein 10 (IP-10), or granulocyte-colony stimulating factor (G-CSF). The term inflammatory cytokines includes also other cytokines associated with inflammatory responses known in the art, e.g., interleukin-1 (IL-1), interleukin-8 (IL-8), interleukin-12 (L-12), interleukin-13 (IL-13), interferon α (IFN-α), etc.

In Vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In Vivo: As used herein, the term "in vivo" refers to events that occur within an organism (e.g., animal, plant, or microbe or cell or tissue thereof).

Insertional and deletional variants: "Insertional variants" when referring to polypeptides are those with one or more amino acids inserted immediately adjacent to an amino acid at a particular position in a native or starting sequence. "Immediately adjacent" to an amino acid means connected to either the alpha-carboxy or alpha-amino functional group of the amino acid. "Deletional variants" when referring to polypeptides are those with one or more amino acids in the native or starting amino acid sequence removed. Ordinarily, deletional variants will have one or more amino acids deleted in a particular region of the molecule.

Intact: As used herein, in the context of a polypeptide, the term "intact" means retaining an amino acid corresponding to the wild type protein, e.g., not mutating or substituting the wild type amino acid. Conversely, in the context of a nucleic acid, the term "intact" means retaining a nucleobase corresponding to the wild type nucleic acid, e.g., not mutating or substituting the wild type nucleobase.

Isolated: As used herein, the term "isolated" refers to a substance or entity that has been separated from at least some of the components with which it was associated (whether in nature or in an experimental setting). Isolated substances (e.g., nucleotide sequence or protein sequence) can have varying levels of purity in reference to the substances from which they have been associated. Isolated substances and/or entities can be separated from at least about 10%, about 20%, about 30%, about 40%, about 50%, about 60%, about 70%, about 80%, about 90%, or more of the other components with which they were initially associated. In some examples, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. The term "substantially isolated" means that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof.

A polynucleotide, vector, polypeptide, cell, or any composition disclosed herein which is "isolated" is a polynucleotide, vector, polypeptide, cell, or composition which is in a form not found in nature. Isolated polynucleotides, vectors, polypeptides, or compositions include those which have been purified to a degree that they are no longer in a form in which they are found in nature. In some aspects, a polynucleotide, vector, polypeptide, or composition which is isolated is substantially pure.

Isomer: As used herein, the term "isomer" means any tautomer, stereoisomer, enantiomer, or diastereomer of any compound of the disclosure. It is recognized that the compounds of the disclosure can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the disclosure, the chemical structures depicted herein, and therefore the compounds of the disclosure, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the disclosure can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

Linker: As used herein, a "linker" refers to a group of atoms, e.g., about 10-1,000 atoms, and can be comprised of the atoms or groups such as, but not limited to, carbon, amino, alkylamino, oxygen, sulfur, sulfoxide, sulfonyl, carbonyl, and imine. The linker can be attached to a modified nucleoside or nucleotide on the nucleobase or sugar moiety at a first end, and to a payload, e.g., a detectable or therapeutic agent, at a second end. The linker can be of sufficient length as to not interfere with incorporation into a nucleic acid sequence. The linker can be used for any useful purpose, such as to form polynucleotide multimers (e.g., through linkage of two or more chimeric polynucleotides molecules or IVT polynucleotides) or polynucleotides conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers and derivatives thereof. Other examples include, but are not limited to, cleavable moieties within the linker, such as, for example, a disulfide bond (—S—S—) or an azo bond (—N=N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

Methods of Administration: As used herein, "methods of administration" may include intravenous, intramuscular, intradermal, subcutaneous, or other methods of delivering a composition to a subject. A method of administration may be selected to target delivery (e.g., to specifically deliver) to a specific region or system of a body. In particular, described herein are intratumoral injection (e.g., injection into one or more tumors or into the tissue immediately adjacent to a tumor).

Modified: As used herein "modified" refers to a changed state or structure of a molecule of the disclosure. Molecules can be modified in many ways including chemically, structurally, and functionally. In some examples, the mRNA molecules of the present disclosure are modified by the introduction of non-natural nucleosides and/or nucleotides, e.g., as it relates to the natural ribonucleotides A, U, G, and C. Noncanonical nucleotides such as the cap structures are not considered "modified" although they differ from the chemical structure of the A, C, G, U ribonucleotides.

Naturally occurring: As used herein, "naturally occurring" means existing in nature without artificial aid.

Non-human vertebrate: As used herein, a "non-human vertebrate" includes all vertebrates except *Homo sapiens*, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

The terms "nucleic acid sequence," and "nucleotide sequence," (an example of a "polynucleotide sequence") are used interchangeably and refer to a contiguous nucleic acid sequence. The sequence can be either single stranded or double stranded DNA or RNA, e.g., an mRNA.

The term "nucleic acid," in its broadest sense, includes any compound and/or substance that comprises a polymer of nucleotides. These polymers are often referred to as polynucleotides. Examples of nucleic acids or polynucleotides of the disclosure include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or hybrids or combinations thereof.

The phrase "nucleotide sequence encoding" refers to the nucleic acid (e.g., an mRNA or DNA molecule) coding sequence which encodes a polypeptide. The coding sequence can further include initiation and termination signals operably linked to regulatory elements including a promoter and polyadenylation signal capable of directing expression in the cells of an individual or mammal to which the nucleic acid is administered. The coding sequence can further include sequences that encode signal peptides.

Off-target: As used herein, "off target" refers to any unintended effect on any one or more target, gene, or cellular transcript.

Open reading frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like.

Optionally substituted: Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g., alkyl) per se is optional.

Part: As used herein, a "part" or "region" of a polynucleotide is defined as any portion of the polynucleotide that is less than the entire length of the polynucleotide.

Patient: As used herein, "patient" refers to a subject who may seek or be in need of treatment, requires treatment, is receiving treatment, will receive treatment, or a subject who is under care by a trained professional for a particular disease or condition.

Pharmaceutically acceptable: The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients can include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are used. Lists of suitable salts are found in *Remington's Pharmaceutical Sciences*, 17th ed., Mack Publishing Company, Easton, Pa., 1985, p. 1418, *Pharmaceutical Salts: Properties, Selection, and Use*, P. H. Stahl and C. G. Wermuth (eds.), Wiley-VCH, 2008, and Berge et al., *Journal of Pharmaceutical Science*, 66, 1-19 (1977), each of which is incorporated herein by reference in its entirety.

Pharmaceutically acceptable solvate: The term "pharmaceutically acceptable solvate," as used herein, means a compound of the disclosure wherein molecules of a suitable solvent are incorporated in the crystal lattice. A suitable solvent is physiologically tolerable at the dosage administered. For example, solvates can be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Physicochemical. As used herein, "physicochemical" means of or relating to a physical and/or chemical property.

Polynucleotide: The term "polynucleotide" as used herein refers to polymers of nucleotides of any length, including ribonucleotides, deoxyribonucleotides, analogs thereof, or mixtures thereof. This term refers to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the term "polynucleotide" includes polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids "PNAs") and polymorpholino polymers, and other synthetic sequence-specific nucleic acid polymers providing that the polymers contain nucleobases in a configuration which allows for base pairing and base stacking, such as is found in DNA and RNA. In particular aspects, the polynucleotide comprises an mRNA. In other aspect, the mRNA is a synthetic mRNA. In some aspects, the synthetic mRNA comprises at least one unnatural nucleobase. In some aspects, all nucleobases of a certain class have been replaced with unnatural nucleobases (e.g., all uridines in a polynucleotide disclosed herein can be replaced with an unnatural nucleobase, e.g., 5-methoxyuridine). In some aspects, the polynucleotide (e.g., a synthetic RNA or a synthetic DNA) comprises only natural nucleobases, i.e., A, C, T and U in the case of a synthetic DNA, or A, C, T, and U in the case of a synthetic RNA.

The skilled artisan will appreciate that the T bases in the codon maps disclosed herein are present in DNA, whereas the T bases would be replaced by U bases in corresponding RNAs. For example, a codon-nucleotide sequence disclosed herein in DNA form, e.g., a vector or an in-vitro translation (IVT) template, would have its T bases transcribed as U based in its corresponding transcribed mRNA. In this respect, both codon-optimized DNA sequences (comprising T) and their corresponding RNA sequences (comprising U) are considered codon-optimized nucleotide sequence of the present disclosure. A skilled artisan would also understand that equivalent codon-maps can be generated by replaced one or more bases with non-natural bases. Thus, e.g., a TTC codon (DNA map) would correspond to a UUC codon (RNA map), which in turn would correspond to a 'P'C codon (RNA map in which U has been replaced with pseudouridine).

Standard A-T and G-C base pairs form under conditions which allow the formation of hydrogen bonds between the N3-H and C4-oxy of thymidine and the N1 and C6-NH$_2$, respectively, of adenosine and between the C2-oxy, N3 and C4-NH$_2$, of cytidine and the C2-NH$_2$, N'—H and C6-oxy, respectively, of guanosine. Thus, for example, guanosine (2-amino-6-oxy-9-β-D-ribofuranosyl-purine) can be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine-) results in a modified nucleotide which will not effectively base pair with guanosine but will form a base pair with isoguanosine (U.S. Pat. No. 5,681,702 to Collins et al.). Isocytosine is available from Sigma Chemical Co. (St. Louis, Mo.); isocytidine can be prepared by the method described by Switzer et al. (1993) Biochemistry 32:10489-10496 and references cited therein; 2'-deoxy-5-methyl-isocytidine can be prepared by the method of Tor et al. (1993) J. Am. Chem. Soc. 115:4461-4467, and references cited therein; and isoguanine nucleotides can be prepared using the method described by Switzer et al., 1993, supra, and Mantsch et al. (1993) Biochem. 14:5593-5601, or by the method described in U.S. Pat. No. 5,780,610 to Collins et al. Other nonnatural base pairs can be synthesized by the method described in Piccirilli et al. (1990) Nature 343:33-37, for the synthesis of 2,6-diaminopyrimidine and its complement (1-methylpyrazolo-[4,3]pyrimidine-5,7-(4H, 6H)-dione. Other such modified nucleotide units which form unique base pairs are known, such as those described in Leach et al. (1992) J. Am. Chem. Soc. 114:3675-3683 and Switzer et al., supra.

The terms "nucleic acid sequence," "nucleotide sequence," or "polynucleotide" are used interchangeably and refer to a contiguous nucleic acid sequence. The sequence can be either single stranded or double stranded DNA or RNA, e.g., an mRNA.

The phrase "nucleotide sequence encoding" and variants thereof refers to the nucleic acid (e.g., an mRNA or DNA molecule) coding sequence that comprises a nucleotide sequence which encodes a polypeptide or functional fragment thereof as set forth herein. The coding sequence can further include initiation and termination signals operably linked to regulatory elements including a promoter and polyadenylation signal capable of directing expression in the cells of an individual or mammal to which the nucleic acid is administered. The coding sequence can further include sequences that encode signal peptides.

The terms "polypeptide," "peptide," and "protein" are used interchangeably herein to refer to polymers of amino acids of any length. The polymer can comprise modified amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids such as homocysteine, ornithine, p-acetylphenylalanine, D-amino acids, and creatine), as well as other modifications known in the art.

The term, as used herein, refers to proteins, polypeptides, and peptides of any size, structure, or function. Polypeptides include gene products, naturally occurring polypeptides, synthetic polypeptides, homologs, orthologs, paralogs, fragments and other equivalents, variants, and analogs of the foregoing. A polypeptide can be a single polypeptide or can be a multi-molecular complex such as a dimer, trimer or tetramer. They can also comprise single chain or multichain polypeptides. Most commonly disulfide linkages are found in multichain polypeptides. The term polypeptide can also apply to amino acid polymers in which one or more amino acid residues are an artificial chemical analogue of a corresponding naturally occurring amino acid. In some examples, a "peptide" can be less than or equal to about 50 amino acids long, e.g., about 5, 10, 15, 20, 25, 30, 35, 40, 45, or 50 amino acids long.

As used herein, the term "polypeptide variant" refers to molecules that differ in their amino acid sequence from a native or reference sequence. The amino acid sequence variants can possess substitutions, deletions, and/or insertions at certain positions within the amino acid sequence, as compared to a native or reference sequence. Ordinarily, variants will possess at least about 50% identity, at least about 60% identity, at least about 70% identity, at least about 80% identity, at least about 90% identity, at least about 95% identity, at least about 99% identity to a native or reference sequence. In some examples, they will be at least about 80%, or at least about 90% identical to a native or reference sequence.

As used herein, a Polypeptide per unit drug (PUD) or product per unit drug, is defined as a subdivided portion of total daily dose, usually 1 mg, pg, kg, etc., of a product (such as a polypeptide) as measured in body fluid or tissue, usually defined in concentration such as pmol/mL, mmol/mL, etc. divided by the measure in the body fluid.

As used herein, the term "preventing" refers to at least partially, including completely, delaying onset of an infection, disease, disorder and/or condition; at least partially or completely delaying onset of one or more symptoms, features, or clinical manifestations of a particular infection, disease, disorder, and/or condition; at least partially or completely delaying onset of one or more symptoms, features, or manifestations of a particular infection, disease, disorder, and/or condition; at least partially or completely delaying progression from an infection, a particular disease, disorder and/or condition; and/or decreasing the risk of developing pathology associated with the infection, the disease, disorder, and/or condition.

The present disclosure also includes prodrugs of the compounds described herein. As used herein, "prodrugs" refer to any substance, molecule or entity that is in a form predicate for that substance, molecule or entity to act as a therapeutic upon chemical or physical alteration. Prodrugs may by covalently bonded or sequestered in some way and that release or are converted into the active drug moiety prior to, upon or after administered to a mammalian subject in need thereof. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Prophylactic: As used herein, "prophylactic" refers to a therapeutic or course of action used to prevent the spread of disease.

Prophylaxis: As used herein, a "prophylaxis" refers to a measure taken to maintain health and prevent the spread of disease. An "immune prophylaxis" refers to a measure to produce active or passive immunity to prevent the spread of disease.

Protein cleavage site: As used herein, "protein cleavage site" refers to a site where controlled cleavage of the amino acid chain can be accomplished by chemical, enzymatic or photochemical means.

Protein cleavage signal: As used herein "protein cleavage signal" refers to at least one amino acid that flags or marks a polypeptide for cleavage.

Protein of interest: As used herein, the terms "proteins of interest" or "desired proteins" include those provided herein and fragments, mutants, variants, and alterations thereof.

Proximal: As used herein, the term "proximal" means situated nearer to the center or to a point or region of interest.

Pseudouridine: As used herein, pseudouridine refers to the C-glycoside isomer of the nucleoside uridine. A "pseudouridine analog" is any modification, variant, isoform or derivative of pseudouridine. For example, pseudouridine analogs include but are not limited to 1-carboxymethyl-pseudouridine, 1-propynyl-pseudouridine, 1-taurinomethyl-pseudouridine, 1-taurinomethyl-4-thio-pseudouridine, 1-methylpseudouridine ($m^1\psi$), 1-methyl-4-thio-pseudouridine ($m^1s^4\psi$) 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydropseudouridine, 2-thio-dihydropseudouridine, 2-methoxyuridine, 2-methoxy-4-thiouridine, 4-methoxy-pseudouridine, 4-methoxy-2-thio-pseudouridine, N1-methyl-pseudouridine, 1-methyl-3-(3-amino-3-carboxypropyl)pseudouridine ($acp^3\psi$), and 2'-O-methyl-pseudouridine (xm).

Purified: As used herein, "purify," "purified," "purification" means to make substantially pure or clear from unwanted components, material defilement, admixture or imperfection.

Reference Nucleic Acid Sequence: The term "reference nucleic acid sequence" or "reference nucleic acid" or "reference nucleotide sequence" or "reference sequence" refers to a starting nucleic acid sequence (e.g., a RNA, e.g., an mRNA sequence) that can be sequence optimized. In some examples, the reference nucleic acid sequence is a wild type nucleic acid sequence, a fragment or a variant thereof. In some examples, the reference nucleic acid sequence is a previously sequence optimized nucleic acid sequence.

Salts: In some aspects, the pharmaceutical composition for intratumoral delivery disclosed herein and comprises salts of some of their lipid constituents. The term "salt" includes any anionic and cationic complex. Non-limiting examples of anions include inorganic and organic anions, e.g., fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfite, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof.

Sample: As used herein, the term "sample" or "biological sample" refers to a subset of its tissues, cells or component parts (e.g., body fluids, including but not limited to blood, mucus, lymphatic fluid, synovial fluid, cerebrospinal fluid, saliva, amniotic fluid, amniotic cord blood, urine, vaginal fluid and semen). A sample further can include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or nucleic acid molecule.

Signal Sequence: As used herein, the phrases "signal sequence," "signal peptide," and "transit peptide" are used interchangeably and refer to a sequence that can direct the transport or localization of a protein to a certain organelle, cell compartment, or extracellular export. The term encompasses both the signal sequence polypeptide and the nucleic acid sequence encoding the signal sequence. Thus, references to a signal sequence in the context of a nucleic acid refer in fact to the nucleic acid sequence encoding the signal sequence polypeptide.

Signal transduction pathway: A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Specific delivery: As used herein, the term "specific delivery," "specifically deliver," or "specifically delivering" means delivery of more (e.g., at least about 1.5 fold more, at least about 2-fold more, at least about 3-fold more, at least about 4-fold more, at least about 5-fold more, at least about 6-fold more, at least about 7-fold more, at least about 8-fold more, at least about 9-fold more, at least about 10-fold more) of a polynucleotide by a nanoparticle to a target tissue of interest (e.g., mammalian liver) compared to an off-target tissue (e.g., mammalian spleen). The level of delivery of a nanoparticle to a particular tissue may be measured by comparing the amount of protein produced in a tissue to the weight of said tissue, comparing the amount of polynucleotide in a tissue to the weight of said tissue, comparing the amount of protein produced in a tissue to the amount of total protein in said tissue, or comparing the amount of polynucleotide in a tissue to the amount of total polynucleotide in said tissue. For example, for renovascular targeting, a polynucleotide is specifically provided to a mammalian kidney as compared to the liver and spleen if about 1.5, 2-fold, 3-fold, 5-fold, 10-fold, 15 fold, or 20 fold more polynucleotide per 1 g of tissue is delivered to a kidney compared to that delivered to the liver or spleen following systemic administration of the polynucleotide. It will be understood that the ability of a nanoparticle to specifically deliver to a target tissue need not be determined in a subject being treated, it may be determined in a surrogate such as an animal model (e.g., a rat model).

Stable: As used herein "stable" refers to a compound that is sufficiently robust to survive isolation to a useful degree of purity from a reaction mixture, and in some cases capable of formulation into an efficacious therapeutic agent.

Stabilized: As used herein, the term "stabilize," "stabilized," "stabilized region" means to make or become stable.

Stereoisomer: As used herein, the term "stereoisomer" refers to all possible different isomeric as well as conformational forms that a compound may possess (e.g., a compound of any formula described herein), in particular all possible stereochemically and conformationally isomeric forms, all diastereomers, enantiomers and/or conformers of the basic molecular structure. Some compounds of the present disclosure may exist in different tautomeric forms, all of the latter being included within the scope of the present disclosure.

Subject: By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; bears, food animals such as cows, pigs, and sheep; ungulates such as deer and giraffes; rodents such as mice, rats, hamsters and guinea pigs; and so on. In certain examples, the mammal is a human subject. In other examples, a subject is a human patient. In a particular example, a subject is a human patient in need of a cancer treatment.

Within the context used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena. Substantially equal, as used herein as it relates to time differences between doses, means plus/minus 2%. Substantially simultaneous, as used herein and as it relates to plurality of doses, means within a few (e.g., 2) seconds.

An individual who is "suffering from" a disease, disorder, and/or condition has been diagnosed with or displays one or more symptoms of the disease, disorder, and/or condition.

An individual who is "susceptible to" a disease, disorder, and/or condition has not been diagnosed with and/or may not exhibit symptoms of the disease, disorder, and/or condition but harbors a propensity to develop a disease or its symptoms. In some examples, an individual who is susceptible to a disease, disorder, and/or condition (for example, cancer) can be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some examples, an individual who is susceptible to a disease, disorder, and/or condition will develop the disease, disorder, and/or condition. In some examples, an individual who is susceptible to a disease, disorder, and/or condition will not develop the disease, disorder, and/or condition.

As used herein, the term "sustained release" refers to a pharmaceutical composition or compound release profile that conforms to a release rate over a specific period of time.

The term "synthetic" means produced, prepared, and/or manufactured by the hand of man. Synthesis of polynucleotides or other molecules of the present disclosure can be chemical or enzymatic.

As used herein, "targeted cells" refers to any one or more cells of interest. The cells may be found in vitro, in vivo, in situ, or in the tissue or organ of an organism. The organism may be an animal, for example, a mammal, including a human.

Target tissue: As used herein "target tissue" refers to any one or more tissue types of interest in which the delivery of a polynucleotide would result in a desired biological and/or pharmacological effect. Examples of target tissues of interest include specific tissues, organs, and systems or groups thereof. In particular applications, a target tissue may be a kidney, a lung, a spleen, vascular endothelium in vessels (e.g., intra-coronary or intra-femoral), or tumor tissue (e.g., via intratumoral injection). An "off-target tissue" refers to any one or more tissue types in which the expression of the encoded protein does not result in a desired biological and/or pharmacological effect. In particular applications, off-target tissues may include the liver and the spleen.

Targeting sequence: As used herein, the phrase "targeting sequence" refers to a sequence that can direct the transport or localization of a protein or polypeptide.

Terminus: As used herein the terms "termini" or "terminus," when referring to polypeptides, refers to an extremity of a peptide or polypeptide. Such extremity is not limited only to the first or final site of the peptide or polypeptide but can include additional amino acids in the terminal regions. The polypeptide based molecules of the disclosure can be characterized as having both an N-terminus (terminated by an amino acid with a free amino group ($NH_2$)) and a C-terminus (terminated by an amino acid with a free carboxyl group (COOH)). Proteins of the disclosure are in some cases made up of multiple polypeptide chains brought together by disulfide bonds or by non-covalent forces (multimers, oligomers). These sorts of proteins will have multiple N- and C-termini. Alternatively, the termini of the polypeptides can be modified such that they begin or end, as the case can be, with a non-polypeptide based moiety such as an organic conjugate.

Therapeutic Agent: The term "therapeutic agent" refers to an agent that, when administered to a subject in need thereof, has a therapeutic, diagnostic, and/or prophylactic effect and/or elicits a desired biological and/or pharmacological effect. For example, in some examples, an mRNA encoding an IL-36-gamma polypeptide can be a therapeutic agent.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hr. period. The total daily dose can be administered as a single unit dose or a split dose.

Transcription factor: As used herein, the term "transcription factor" refers to a DNA-binding protein that regulates transcription of DNA into RNA, for example, by activation or repression of transcription. Some transcription factors affect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors may regulate transcription of a target gene alone or in a complex with other molecules.

Transcription: As used herein, the term "transcription" refers to methods to introduce exogenous nucleic acids into a cell. Methods of transfection include, but are not limited to, chemical methods, physical treatments and cationic lipids or mixtures.

Transfection: As used herein, "transfection" refers to the introduction of a polynucleotide into a cell wherein a polypeptide encoded by the polynucleotide is expressed (e.g., mRNA) or the polypeptide modulates a cellular function (e.g., siRNA, miRNA). As used herein, "expression" of a nucleic acid sequence refers to translation of a polynucleotide (e.g., an mRNA) into a polypeptide or protein and/or post-translational modification of a polypeptide or protein.

Treating, treatment, therapy: As used herein, the term "treating" or "treatment" or "therapy" refers to partially or completely alleviating, ameliorating, improving, relieving, delaying onset of, inhibiting progression of, reducing severity of, and/or reducing incidence of one or more symptoms or features of a hyper-proliferative disease, e.g., cancer. For example, "treating" cancer can refer to inhibiting survival, growth, and/or spread of a tumor. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Tumor Microenvironment": As used herein, "tumor microenvironment" refers to the cellular compositions within a tumor with respect to the presence or absence of infiltrating immune and/or inflammatory cells, as well as the type(s) of such cells within the tumor. In one aspect, a tumor microenvironment is an "inflamed tumor microenvironment", which refers to the presence of immune and/or inflammatory cells infiltrated into the tumor, with the predominant cell type being granulocytes. In another aspect, a tumor microenvironment is an "immunosuppressive tumor microenvironment", which refers to the presence of immune and/or inflammatory cells infiltrated into the tumor, with the predominant cell types being monocytic cells and macrophages. In another aspect, a tumor microenvironment is an "immunologically barren tumor microenvironment", which refers to an absence of significant infiltration into the tumor of immune and/or inflammatory cells.

Unmodified: As used herein, "unmodified" refers to any substance, compound or molecule prior to being changed in any way. Unmodified can, but does not always, refer to the wild type or native form of a biomolecule. Molecules can undergo a series of modifications whereby each modified molecule can serve as the "unmodified" starting molecule for a subsequent modification.

Uracil: Uracil is one of the four nucleobases in the nucleic acid of RNA, and it is represented by the letter U. Uracil can be attached to a ribose ring, or more specifically, a ribofuranose via a $\beta$-$N_1$-glycosidic bond to yield the nucleoside uridine. The nucleoside uridine is also commonly abbreviated according to the one letter code of its nucleobase, i.e., U. Thus, in the context of the present disclosure, when a monomer in a polynucleotide sequence is U, such U is designated interchangeably as a "uracil" or a "uridine."

Uridine Content: The terms "uridine content" or "uracil content" are interchangeable and refer to the amount of uracil or uridine present in a certain nucleic acid sequence. Uridine content or uracil content can be expressed as an absolute value (total number of uridine or uracil in the sequence) or relative (uridine or uracil percentage respect to the total number of nucleobases in the nucleic acid sequence).

Uridine-Modified Sequence: The terms "uridine-modified sequence" refers to a sequence optimized nucleic acid (e.g., a synthetic mRNA sequence) with a different overall or local uridine content (higher or lower uridine content) or with different uridine patterns (e.g., gradient distribution or clustering) with respect to the uridine content and/or uridine patterns of a candidate nucleic acid sequence. In the content of the present disclosure, the terms "uridine-modified sequence" and "uracil-modified sequence" are considered equivalent and interchangeable.

A "high uridine codon" is defined as a codon comprising two or three uridines, a "low uridine codon" is defined as a codon comprising one uridine, and a "no uridine codon" is a codon without any uridines. In some examples, a uridine-modified sequence comprises substitutions of high uridine codons with low uridine codons, substitutions of high uridine codons with no uridine codons, substitutions of low uridine codons with high uridine codons, substitutions of low uridine codons with no uridine codons, substitution of no uridine codons with low uridine codons, substitutions of no uridine codons with high uridine codons, and combinations thereof. In some examples, a high uridine codon can be replaced with another high uridine codon. In some examples, a low uridine codon can be replaced with another low uridine codon. In some examples, a no uridine codon can be replaced with another no uridine codon. A uridine-modified sequence can be uridine enriched or uridine rarefied.

Uridine Enriched: As used herein, the terms "uridine enriched" and grammatical variants refer to the increase in uridine content (expressed in absolute value or as a percentage value) in a sequence optimized nucleic acid (e.g., a synthetic mRNA sequence) with respect to the uridine content of the corresponding candidate nucleic acid sequence. Uridine enrichment can be implemented by substituting codons in the candidate nucleic acid sequence with synonymous codons containing less uridine nucleobases. Uridine enrichment can be global (i.e., relative to the entire length of a candidate nucleic acid sequence) or local (i.e., relative to a subsequence or region of a candidate nucleic acid sequence).

Uridine Rarefied: As used herein, the terms "uridine rarefied" and grammatical variants refer to a decrease in uridine content (expressed in absolute value or as a percentage value) in a sequence optimized nucleic acid (e.g., a synthetic mRNA sequence) with respect to the uridine content of the corresponding candidate nucleic acid sequence. Uridine rarefication can be implemented by substituting codons in the candidate nucleic acid sequence with synonymous codons containing less uridine nucleobases. Uridine rarefication can be global (i.e., relative to the entire length of a candidate nucleic acid sequence) or local (i.e., relative to a subsequence or region of a candidate nucleic acid sequence).

Variant: The term variant as used in present disclosure refers to both natural variants (e.g., polymorphisms, isoforms, etc.) and artificial variants in which at least one amino acid residue in a native or starting sequence (e.g., a wild type sequence) has been removed and a different amino acid inserted in its place at the same position. These variants can be described as "substitutional variants." The substitutions can be single, where only one amino acid in the molecule has been substituted, or they can be multiple, where two or more amino acids have been substituted in the same molecule. If amino acids are inserted or deleted, the resulting variant would be an "insertional variant" or a "deletional variant" respectively.

Vaccine: as used herein a vaccine may be a therapy that help the body fight cancer. Specifically, the vaccines described herein may treat cancer. The vaccines described herein are not limited to prevention of disease (e.g., cancer) but may treat an existing cancer, including a tumor or tumors.

The mRNA vaccines described herein may include any appropriate delivery vehicle molecule. For example, the delivery vehicle molecule may be a lipid based vehicle (such as a lipid nanoparticle) or a polymer-based nanoparticle. In particular the delivery vehicle (DV) molecule may be an amino-lipidated peptoid delivery vehicle.

In general the delivery vehicle molecule protects the mRNA(s) from RNase degradation, increase their cellular uptake, and facilitate endosome escape, thereby expressing functional proteins in the cytosol. These attributes make it feasible to address technical challenges for in vivo delivery of mRNA for patients.

Thus, as described herein, the mRNA vaccines described herein may include an mRNA encoding one or more tumor-specific antigen and one or more immunomodulator agent that is co-formulated with the same delivery vehicle molecule. The delivery vehicle molecule may be, for example, a lipid nanoparticle (LNP). LNP formulations may be composed of an ionizable or cationic lipid or polymeric material, bearing tertiary or quaternary amines to encapsulate the polyanionic mRNA; a zwitterionic lipid (e.g., 1,2-dioleoyl-sn-glycero-3-phosphoethanolamine) that resembles the lipids in the cell membrane; cholesterol to stabilize the lipid bilayer of the LNP; and a polyethylene glycol (PEG)-lipid to lend the nanoparticle a hydrating layer, improve colloidal stability, and reduce protein absorption.

Multicomponent LNPs may be taken up by endocytosis and can electrostatically attach and fuse with the cell membrane using inverted non-bilayer lipid phases. Once inside the cell, LNPs may be routed into early endosomes, followed by late endosomes, and finally the lysosomes where the mRNA contents are enzymatically degraded.

One class of delivery vehicle molecules includes the cationic or ionizable lipids and lipid-like materials. Cationic lipids bear alkylated quarternary ammonium groups and retain their cationic nature in a pH-independent fashion, while ionizable lipids acquire positive charges by protonation of free amines as pH is lowered. Lipid-like materials bear more hydrophobic side chains than natural lipids. Cationic lipids, such as N-[1-(2,3-dioleoyloxy)propyl]-N,N,N-trimethylammonium chloride (DOTMA) may be used. Alternatively or additionally, pH-dependent ionizable materials may be used. The ionizable lipid named Dlin-MC3-DMA (MC3) can also be used to transfect mRNA in order to express therapeutic proteins.

Polymeric materials may be used for the delivery of therapeutic mRNA. For example, low-molecular-weight polyethyleneimine (PEI) modified with fatty chains may be used for siRNA and mRNA delivery to reduce toxicity of high-molecular weight PEI. Poly(glycoamidoamine) polymers modified with fatty chains (e.g., in some variations including a tartrate backbone) have been shown to deliver mRNA. Poly(β-amino)esters (PBAEs) are biodegradable polymers that may be used for nucleic acid delivery, including PBAEs formulated with PEG-lipid to increase their serum stability. Hyperbranched PBAEs may be used for mRNA delivery.

Polymethacrylates with amine-bearing side chains, polyaspartamides with oligoaminoethylene side chains, and polyacrylic acids amidated with tetramine with alternating ethyl-propyl-ethyl spacers have been reported to transfect mRNA and may be used as a delivery vehicle molecule. Self-immolative polycarbonate-block-poly(α-amino)esters may release mRNA upon rearrangement followed by degradation at pH 7.4, to facilitate endosomal escape. Biodegradable amino polyesters (APEs), may be synthesized with low dispersity from tertiary amino alcohols as initiators in ring-opening polymerization of various lactones, and may be capable of tissue-selective mRNA delivery. Other biodegradable polymers with biocompatible degradation products and enhanced endosomal escape capabilities may be used for mRNA delivery.

In some variations the delivery vehicle molecule may include dendrimers. For example, Polyamidoamine (PAMAM) or polypropylenimine-based dendrimers have been extensively studied for gene delivery. Fatty chain-modified PAMAM dendrimers, and/or a modified PAMAM dendrimer co-formulated with poly(lactic-co-glycolic acid) (PLGA) and ceramide-PEG may be used as a delivery vehicle molecule.

Alternatively, in some variations cell-penetrating peptides (CPPs) may be used as delivery vehicle molecules. CPPs may promote clustering of the negatively charged glycosaminoglycans on the cell surface, which in turn triggers macropinocytosis and lateral diffusion or directly disrupts the lipid bilayer. A CPP with arginine-rich amphipathic RALA sequence repeats may be used. In some variations the delivery vehicle molecule may be a combination of cationic and zwitterionic lipids, reminiscent of cationic and helper lipids ("zwitterionic amino lipids" or ZALs).

In particular, the delivery vehicle molecules described herein may be amino-lipidated peptoid delivery vehicles. For example, these delivery vehicles may be a lipid-containing amphipathic delivery vehicle that provides packaging and protection of mRNA cargos during circulation, avoid immune recognition, and may facilitate cellular uptake and release. Examples of these delivery vehicles may be found in international patent application, PCT/US19/53661, titled "LIPID NANOPARTICLE FORMULATIONS COMPRISING LIPIDATED CATIONIC PEPTIDE COMPOUNDS FOR NUCLEIC ACID DELIVERY", and filed on Sep. 27, 2019, and in international patent application PCT/US19/53655, titled "TERTIARY AMINO LIPIDATED CATIONIC PEPTIDES FOR NUCLEIC ACID DELIVERY" and filed on Sep. 27, 2019, each of which is herein incorporated by reference in its entirety. Multiple types of delivery vehicle molecules may be used, and each type may be encapsulated together with both the mRNA encoding one or more tumor-specific antigen and mRNA encoding one or more immunomodulatory agents as described herein.

In general, the methods and compositions described herein may include a method of the treatment of cancer. These methods may include intratumorally injecting an mRNA vaccine encoding a tumor-specific antigen and an mRNA encoding one or more immunomodulatory agent, wherein the mRNA vaccine and the immunomodulatory agent are encapsulated together with a delivery vehicle molecule. In particular the tumor-specific antigen may be a patient-specific tumor antigen that may be identified as changes (e.g., mutations, including deletions, additions, etc.) in the sequence of one or more genes and/or proteins and/or the expression of one or more genes and/or proteins as compared to native patient tissues, and particularly native patient tissues having the same differentiation lineage; for example liver tissue as compared to liver tumor tissue, etc.

For example, patient-specific tumor antigens may include neo-epitopes (also referred to as neo-antigens). The methods and compositions described herein may improve the efficacy of mRNA vaccines using neo-epitopes.

Neo-epitopes can arise from any genomic mutation altering protein sequence, including non-synonymous mutations, retained introns, post-translational modification that alters amino acid, gene fusions and frameshift in/del variants. Next-generation sequencing (NGS) can be used to identify each of these types of variants, except for post-translational modification, which may be detected by techniques such as mass spectrometry.

Tumor-specific antigens may be somatic mutations, and may be identified in any appropriate manner.

Massively parallel NGS may be used to identify neo-epitopes without requiring individual cDNA library screening. Whole exome/genome sequencing may be used to identify tumor-specific genetic mutations altering the protein coding regions quickly in a high throughput manner, facilitating neo-epitopes prediction. Mass spectrometry can also be used to identify peptides bound to the MHC molecules on the surface of cells. A forward approach of performing NGS on germline and tumor DNA to identify protein altering mutations that are specific to the cancer cells, followed by epitope prediction via in silico algorithms, may be used.

For example, tumor samples are extracted from a patient (and/or cultured, including short-term cultures) and examined by Whole-Exome Sequencing (or other exome sequencing) to identify mutation derived neo-epitopes that are patient-specific. For example, DNA and RNA may be extracted from patient tumor cells and exome capture for DNA sequencing may be carried out (e.g., using the Agilent human whole-exome SureSelect assay). RNA-seq libraries were prepared (e.g., using Illumina mRNA-seq protocol). Libraries may be sequenced (e.g., on an Illumina HiSeq2500) to generate nucleotide reads. RNA reads may be aligned to a human reference genome and assembled into transcripts (e.g., using Bowtie-TopHat-Cufflinks, open source Tuxedo Suite software, Trapnell, C. et al., Nat. Protoc. 7, 562-578 (2012)). WES data may be mapped to reference genome (e.g., by BWA, Burrows-Wheeler Aligner, http://bio-bwa.sourceforge.net/) and then processed to detect somatic mutations (e.g., using MuTect, a highly sensitive and specific mutation-calling algorithm, Cibulskis, K. et al. Sensitive detection of somatic point mutations in impure and heterogeneous cancer samples. Nat. Biotechnol. 31, 213-219 (2013)). Patient-specific alleles may thus be determined (e.g., using Seq2HLA, Boegel, S. et al. HLA typing from RNA-Seq sequence reads. Genome Med. 4, 102 (2012)). The identified mutations may be putative candidate antigenic peptides that may be further filtered by tumor expression level, e.g., using RNA sequence data. Candidate peptides (e.g., of greater than 8-11 characters long) may be ranked based, for example, by peptide-MHC binding affinity prediction ($IC_{50}$nM) performed in silico (e.g., using NetMHCpan, e.g., http://www.cbs.dtu.dk/services/NetMHCpan/). Any of the software described above is merely exemplary, and other software may be used.

The prediction of neo-epitopes may rely on the in silico processing of genomic data and may use knowledge of the donors HLA type, tumor mRNA expression, germline DNA and tumor DNA. The tumor mRNA expression data such as whole genome microarrays or RNA-seq may be overlaid on tumor-specific cancer mutation information, to identify variants in transcribed genes. These variants may then be run through epitope prediction algorithms, to identify peptide sequences that potentially bind to individual-specific HLA-alleles. There are many epitope prediction algorithms available, including SYFPEITHI (Schuler et al. 2007), RANK- PEP (Reche et al. 2002), NetMHCpan (Jurtz et al. 2017), NetMHCcons (Karosiene et al. 2012), PickPocket (Zhang et al. 2009), MHCflurry (pre-print, 10.1101/174243), ANN (Singh and Mishra 2008) and SMM (Peters and Sette 2005). Such algorithms may employ different prediction models but have all been trained using characterized epitope/MHC combinations, resulting in the prediction of the likelihood of short peptide sequences binding to a given HLA-allele. Bioinformatic pipelines have been created that use whole genome/exome sequencing data and integrate the analysis to include HLA-allele typing, mRNA expression data, peptide processing prediction and HLA-allele binding for the wild-type and mutated peptide. These may include pVAC-seq (Hundal et al. 2016), MuPeXi (Bjerregaard et al. 2017), Cloudneo (Bais et al. 2017) and Tlminer (Tappeiner et al. 2017). Computational tools (e.g., LOHHLA, loss of heterozygosity in human leukocyte antigen) may be used to allow allele-specific copy number estimation of the HLA locus from next-generation sequencing data.

In any of the mRNA vaccines and methods described herein, one or more, and in some cases multiple (e.g., 2 or more, 3 or more, 4 or more, 5 or more, 6 or more, 7 or more, etc.) may be combined into a single mRNA (or multiple mRNAs), e.g., encoded together. These combined neo-epitopes mRNAs may be successfully used as described herein.

Alternatively or additionally, mRNA based tumor vaccination may include tumor shared antigens, i.e. antigens that are overexpressed and HLA-presented in many tumors from different patients.

NON-LIMITING WORKING EXAMPLES

In some examples, syngeneic mouse cancer models were used to show that the mRNA vaccination methods described herein may be used against tumor antigens and may result in durable tumor regression and long term CD8+ T-cell mediated cancer immunity in a fraction of mice.

Example 1: Tumor Model

Figure 2:
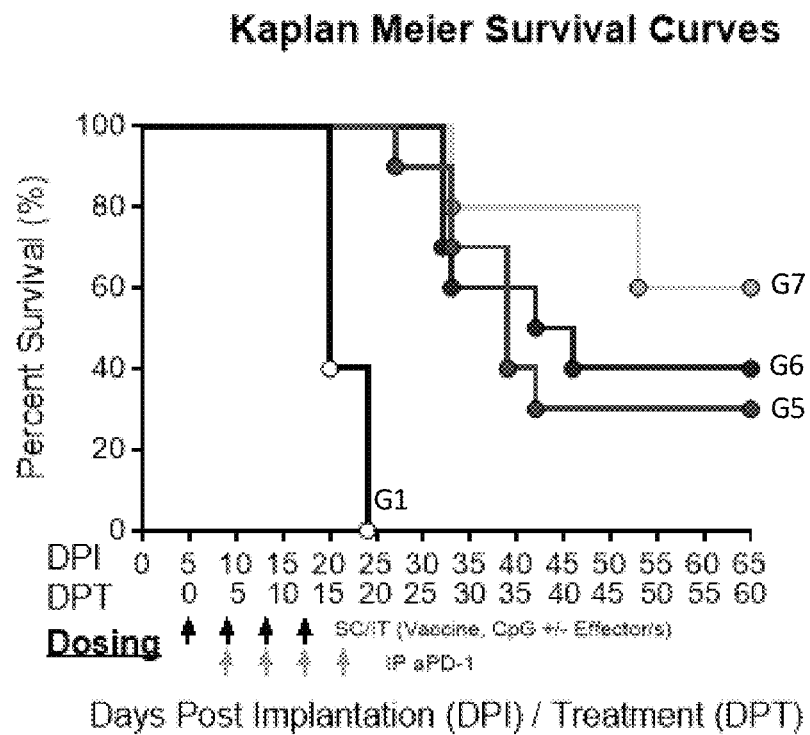
FIG. 2 is a graph showing the improved efficacy of the mRNA vaccines described herein in the treatment of cancer. Syngeneic mouse cancer models were treated as indicated herein.

FIG. 2 illustrates one example a syngeneic mouse model that was used in which the mice were implanted with a tumor cell line (EG. 7) and tumor growth was monitored. The tumor line was engineered to express a shared tumor-specific antigen, ovalbumin. Mice were sacrificed after a pre-set tumor growth volume. FIG. 2 illustrates the results of various mRNA vaccines and treatment methods as described herein. In FIG. 2, negative control mice (G1) exceeded the pre-set tumor volume limit by 25 days post implantation (DPI). In contrast, a significant slowing of tumor growth was seen in mice treated with subcutaneous injection of an mRNA of a shared tumor-specific antigen (e.g., in an amino-lipidated peptoid delivery vehicle) as well as with intratumoral injection of an mRNA encoding an immunomodulatory agent (anti-CTLA-4), also combined with an amino-lipidated peptoid delivery vehicle ("G5"). Compared with the result using G5, slightly better, though similar, improvements in slowing or reducing tumor growth were seen with intratumoral injection of an mRNA vaccine including an mRNA of the tumor-specific antigen and mRNA encoding an immunomodulatory agent (anti-CTLA-4) in an amino-lipidated peptoid delivery vehicle ("G6"). However, surprisingly, much greater survival was seen in animals treated with an mRNA vaccine including mRNA of the tumor-specific antigen and mRNA encoding two immunomodulatory agents (both anti-CTLA-4 and TGF-β) in an amino-lipidated peptoid delivery vehicle ("G7"). The DNA sequences for the anti-CTLA-4 is provided in SEQ ID NO: 1 (heavy chain) and SEQ ID NO: 3 (light chain). Examples sequence for TGF-β are shown in SEQ ID NO: 7 and SEQ ID NO: 9. In FIG. 2, full-length IgG anti-CTLA4 was encoded by the mRNA in the mRNA vaccine. In all of the treatments described above, the immunosimulator, CpG, was included with the mRNA vaccine. The same amino-lipidated peptoid was used for all of the intratumoral injections.

As shown in FIG. 2, intratumoral injection of an mRNA to a tumor-specific antigen, in combination with one or (more preferably) more immunomodulators (such as aCTLA4 and aTGF-β) resulted in a dramatic increase in efficacy of the mRNA vaccination.

Figure 3:
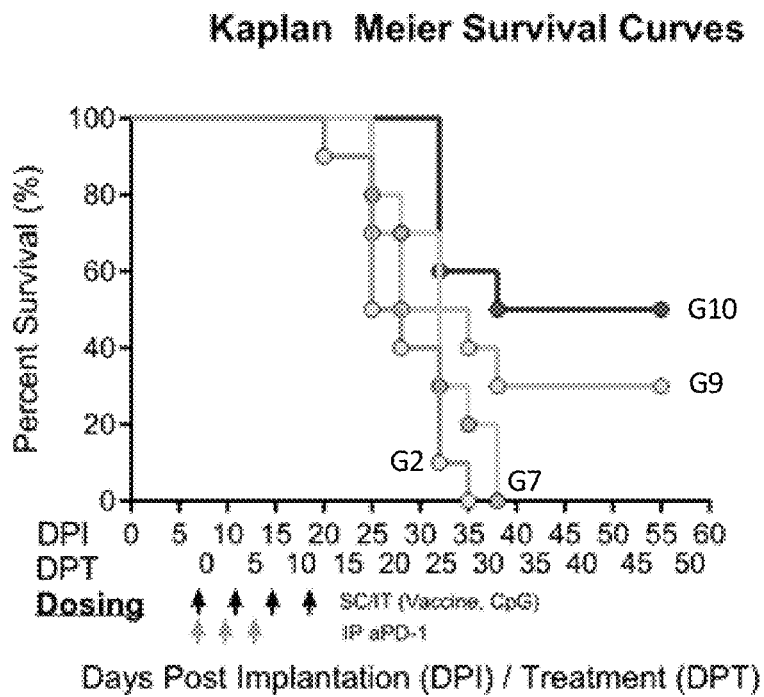
FIG. 3 is a graph showing the improved efficacy of another mRNA vaccine described herein in the treatment of cancer.

A similar experiment was performed using a syngeneic mouse model in which a different tumor cell line (MC38) was used. This is shown in FIG. 3. In this example, the mRNA vaccine including tumor-specific antigens identified by sequencing the MC38 tumor and neo-epitopes were identified. Seven epitopes were identified and chained to form a single mRNA encoding all seven tumor-specific antigens; the sequences of the epitopes were expressed in a custom scaffold to enhance presentation.

In FIG. 3 the control animals ("G2") were injected with a non-coding mRNA and CpG, along with the amino-lipidated peptoid delivery vehicle. Subcutaneous injection of the mRNA vaccine including just the tumor-specific mRNA and the amino-lipidated peptoid delivery ("G7") did not significantly impact tumor growth, as compared to control animals. In contrast animal injected intratumorally with both the tumor specific mRNA and anti-CTLA-4 mRNA combined with an amino-lipidated peptoid ("G9") showed a significant slowing or reduction in tumor growth and therefore survival. Most significantly, intratumoral injection of an mRNA vaccine including an mRNA of the tumor-specific antigen and mRNA encoding three immunomodulatory agents (anti-CTLA-4 and TGF-β and single chain IL-12) with an amino-lipidated peptoid delivery vehicle ("G10" showing a "multi-effector cocktail") resulted in a dramatic slowing or reduction in tumor growth. In this example, the mRNA vaccinations also all included CpG.

Figure 4:
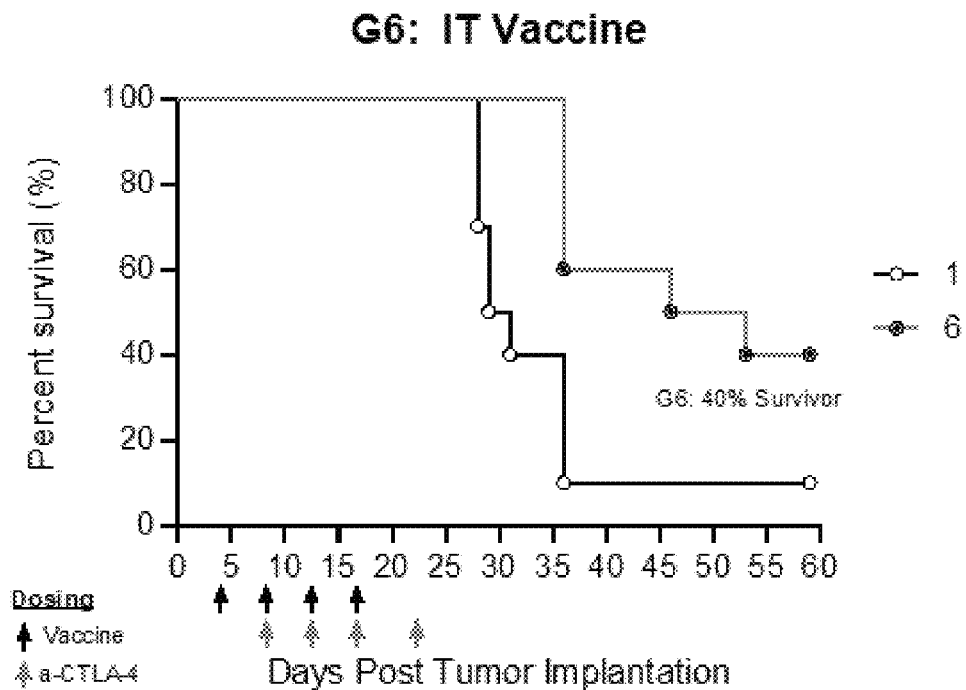
FIG. 4 is another example showing the improved efficacy of an mRNA vaccine as described herein in the treatment of a mouse cancer model, comparing control (1) with intratumoral injection of an mRNA vaccine (6) including mRNA of the tumor specific antigen and an mRNA encoding an immunomodulatory agent (anti-CTLA-4) in an amino-lipidated peptoid delivery vehicle.
Figure 7:
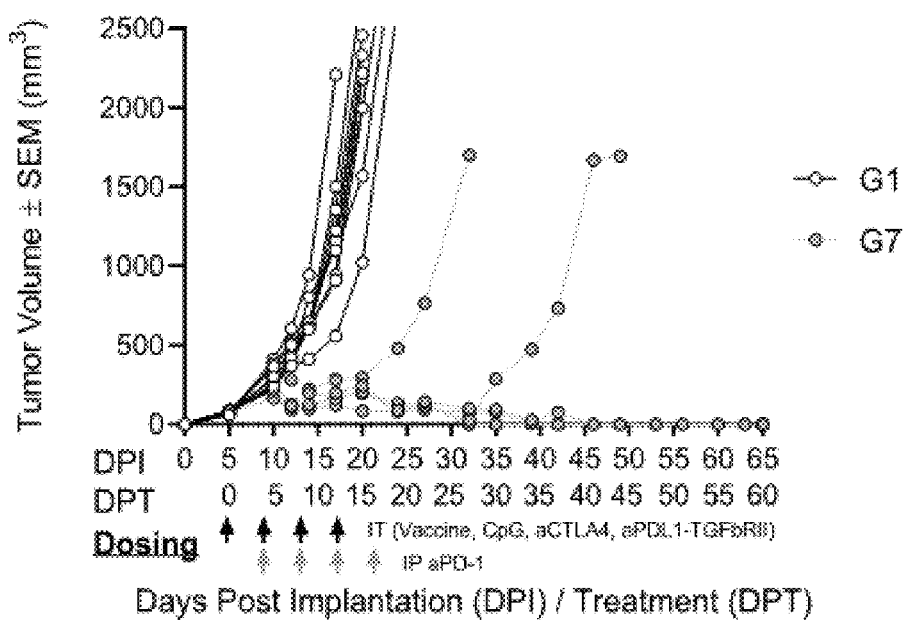
FIG. 7 is a graph showing the effect of intratumoral injection of an mRNA vaccine (similar to that used in FIG. 6) on survival in a lymphoma animal model (compared to a negative control). The subcutaneous injection of the mRNA vaccine (G7, including mRNA encoding a tumor-specific antigen, and two immunomodulatory agents, anti-CTLA-4 and TGF-β-PLD1) with an amino-lipidated peptoid delivery vehicle showed a large reduction (greater than approximately 80%) in tumor volume as compared to control animals.

FIG. 4 shows the results of another example in which a syngeneic mouse model was examined for dosing using intratumoral injection alone. In FIG. 7 the mRNA vaccine with a tumor-specific antigen and amino-lipidated peptoid alone ("1") is compared with an mRNA vaccine including an mRNA of a tumor-specific antigen and amino-lipidated peptoid combined with anti-CTLA-4 and amino-lipidated peptoid ("6"). As shown, the use of a single immunomodulatory agent (in this case, anti-CTLA-4) dramatically increased the survival (e.g., by slowing or reducing the growth of the tumors).

Figure 5:
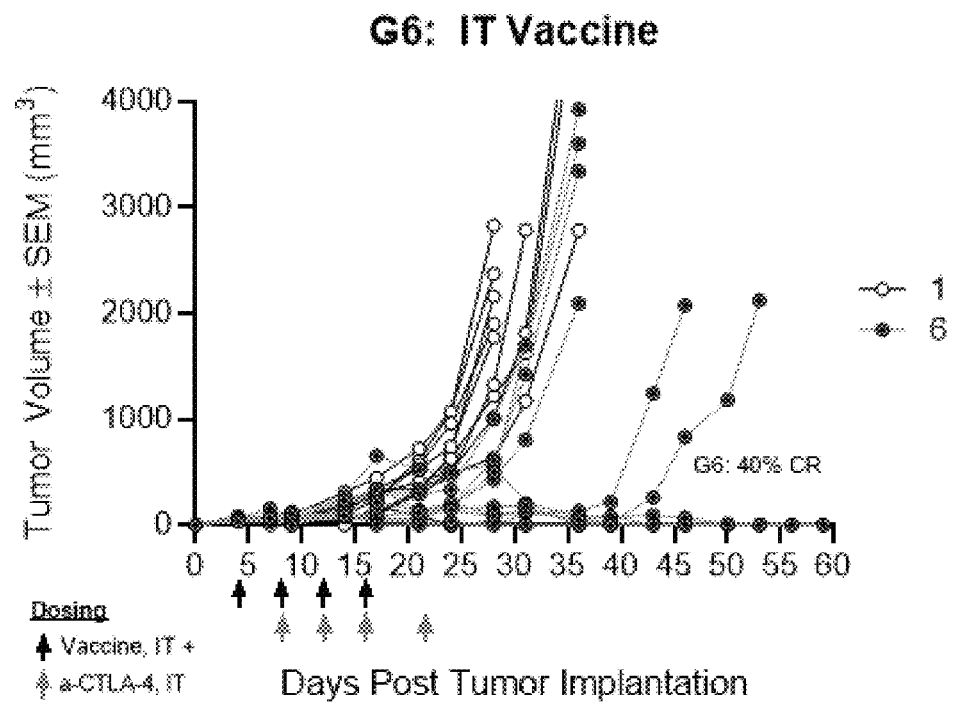
FIG. 5 shows the improved efficacy of mRNA vaccination as described herein, showing the efficacy in improved survival in a lymphoma animal model (compared to negative control, n=6) of intratumoral injection of an mRNA vaccine (n=6) including mRNA of the tumor specific antigen and an mRNA encoding an immunomodulatory agent (anti-CTLA-4) in an amino-lipidated peptoid delivery vehicle.

FIG. 5 graphically illustrates the effect on tumor volume over time for the animal subjects summarized in FIG. 4, following intratumoral injection (IT) of an mRNA of a tumor-specific antigen and amino-lipidated peptoid alone ("1") as compared with an mRNA vaccine including an mRNA of a tumor-specific antigen and amino-lipidated peptoid combined with anti-CTLA-4 and amino-lipidated peptoid ("6"). Animals were typically sacrificed when their tumor volume exceeded 3000 mm$^3$. In virtually all of the animals treated with the tumor-specific antigen and the anti-CTLA-4 mRNA with an amino-lipidated peptoid showed a delay in the tumor growth, while some showed a reduction or block in tumor volume.

Figure 6:
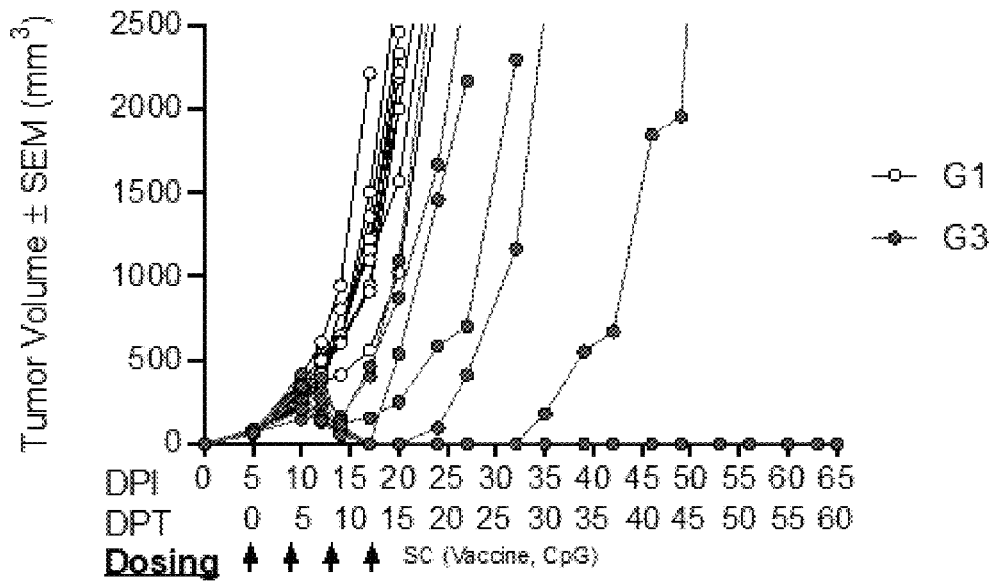
FIG. 6 is a graph showing the effect of subcutaneous injection of an mRNA vaccine on survival in a lymphoma animal model (compared to a negative control). The subcutaneous injection of an mRNA vaccine (G3, including mRNA encoding an immunomodulatory agent) with an amino-lipidated peptoid delivery vehicle showed a reduction (approximately 50%) in tumor volume as compared to control animals.

FIG. 6 shows that similar results were seen in syngeneic mice treated by subcutaneous injection, showing an approximately 50% control of the tumor (e.g., preventing growth of the tumor over time, as compared to control "G1") animals. In contrast in FIG. 7, the treatment mice were injected with 2 μg of the mRNA vaccine including the tumor-specific antigen, as well as anti-CTLA-4 mRNA and TGF-B-PDL1 mRNA with an amino-lipidated peptoid), showing approximately 80% tumor control. All of the mice showed a slowing in tumor growth and the majority showed a reduction in tumor volume over time.

The results described above all included multiple dosing of the subject animals with the mRNA vaccine. In general it may be beneficial, but not necessary, to provide multiple doses of the intratumoral injection of the mRNA vaccine. For example, injections may be spaced by about 4 days or more (e.g., biweekly). In some variations only two or at most three injections are used.

Figure 8A:
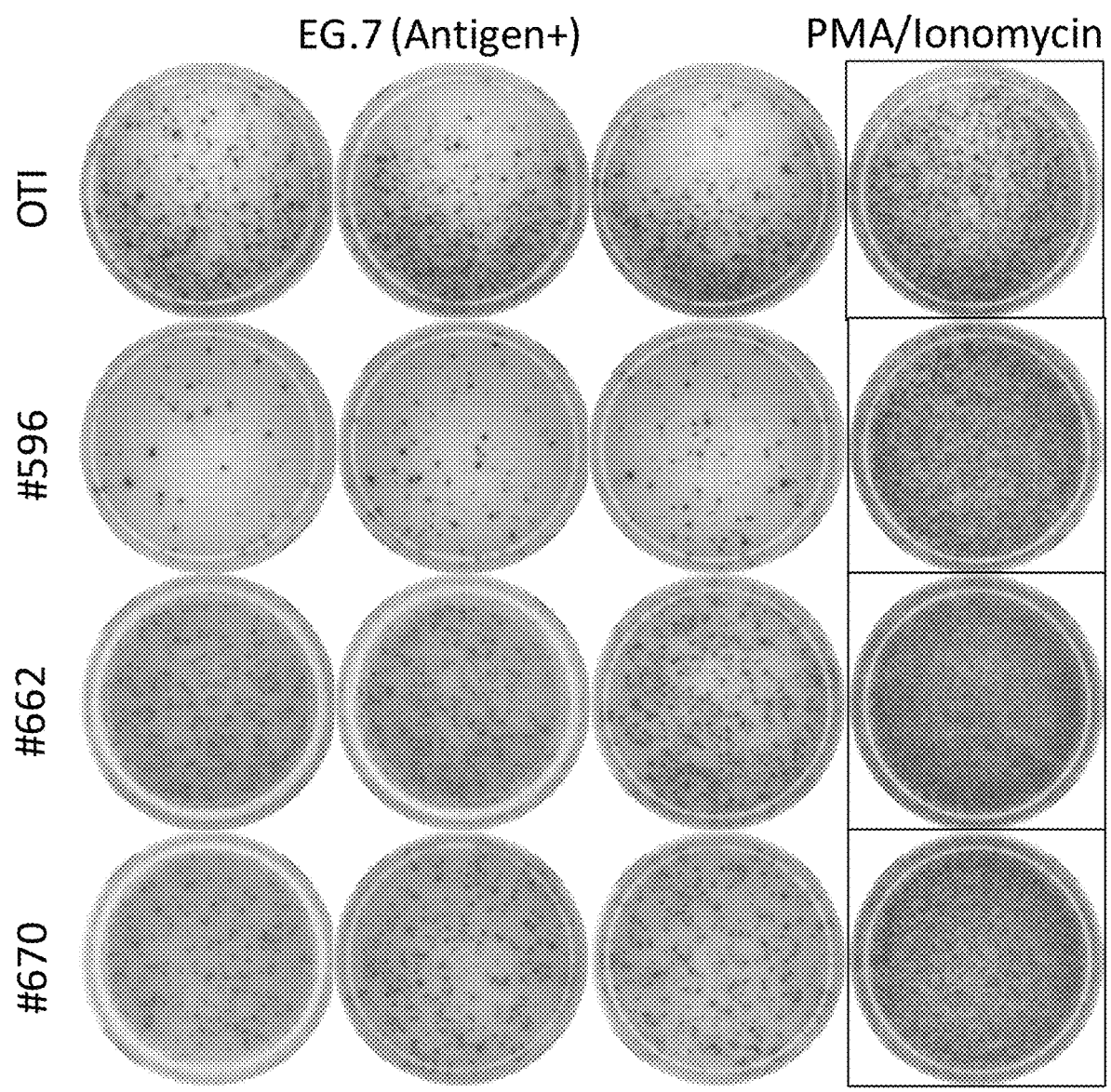
FIGS. 8A and 8B illustrate that subjects (from the mouse animal model) that are long-term survivors following the mRNA vaccination described herein develop strong and persistent CD8+ effector T-cell cancer immunity and are resistant to further tumor challenges.
Figures 8B, 9:
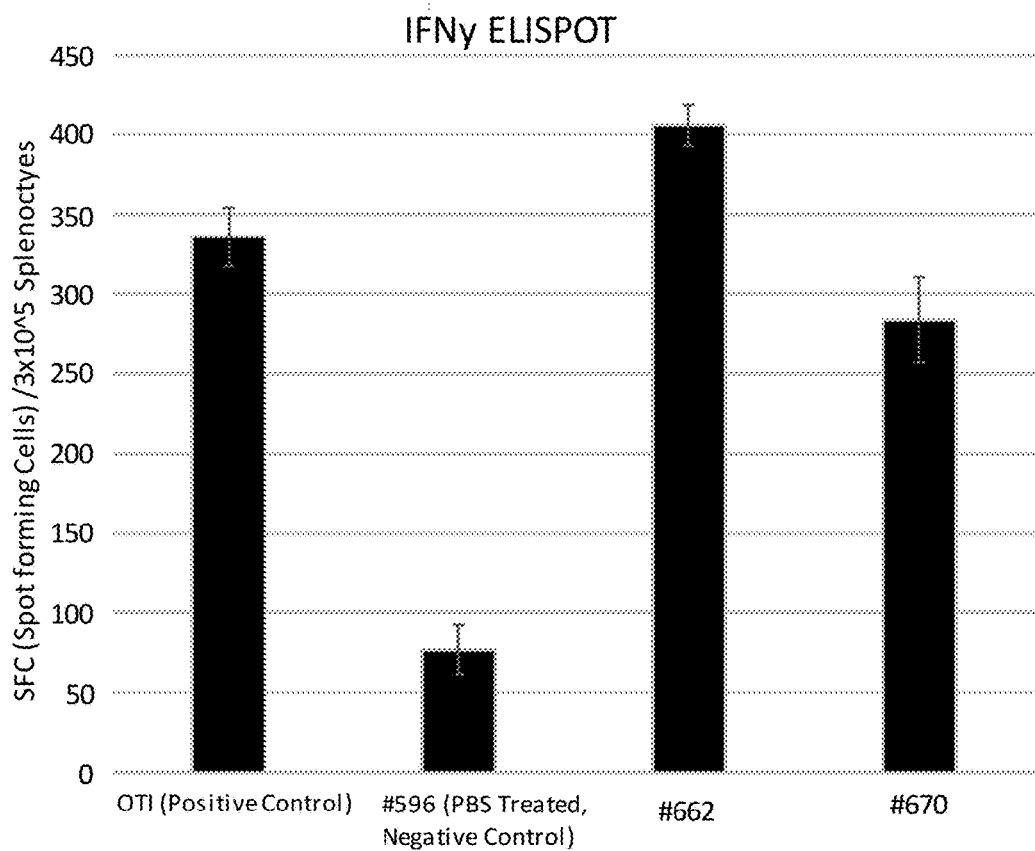
FIG. 9 is a table (Table 1) showing the test groups tested in a lymphoma tumor model, as described herein.

Surprisingly, from the experiments described above it was observed that mice that were long-term survivors developed strong and persistent CD8+ effector T-cell cancer immunity and were resistant to further tumor challenges. For example, FIGS. 8A and 8B illustrate the efficient T-cell response resulting from the mRNA vaccination methods described herein. An Elispot assay was run with 3×10$^5$ splenocytes per well and tumor cells (such as the EG7 cells at 1×10$^6$) were used as a stimulant. In FIG. 8A cells from positive control (OTI) and negative control (#596) were compared to two of the long-surviving mice (#662 and #670), showing counts of T-cells that secrete interferon gamma in response to tumor exposure. Cells were taken from circulating blood or spleens 2 months after the last treatment.

FIG. 8B quantifies this data, showing a significant response (comparable or superior to the positive control mice, OTI, which were engineered to respond to the ovalbumin tumor-specific marker used). Thus, it was observed that mice immunized as described herein continued to recognize the tumors, showing significant strong and persistent immunity, showing the effectiveness of the methods described herein in these mice, and suggesting a long-term effect from even a single treatment.

Example 2: EG7-OVA Lymphoma Model

In this example, mice were injected either intratumorally (IT) or intramuscularly (IM) into EG7 mice (an EG7-OVA lymphoma model). IT injection was bilateral and OVA-mRNA with or without effectors were injected. IT injection was a unilateral injection of the same OVA-mRNA with or without effectors. Table 1 (shown in FIG. 9) illustrates the various tested groups, which were injected with antigen mRNA ("OVA") (groups 1, 2, 5, 6, 7, and 10) or non-coding antigen mRNA ("non-coding mRNA") (groups 3, 4, 8 and 9) with CpG (groups 1, 3, 6 and 8), IL-12 (groups 2, 4, 7 and 9), or both antigen mRNA, non-coding antigen mRNA and CM-CSG. For each of groups 1-10, ten mice were injected, and a total of three injections were performed. The initial injection was done on day 4, when tumor sizes reached approximately 75 mm; the second and third injections (boosts) were done one and two weeks following the initial injection. Control animals (mice in group 11 and 12) did not receive delivery vehicle or mRNA. Mice were sacrifices after tumors were greater than 1500 mm$^3$, or after sixty days. Spleen and serum were examined and were graded on CD8+ T cells.

CD8 T-cell responses were measured using flow cytometry. The percent tetramer positive CD8 T cells provides a biomarker for the therapeutic intervention's ability to induce tumor-specific immunity. Individual mice were bled on day 11 and day 28 after challenge. A single-cell suspension of circulating Peripheral Blood Mononuclear Cells (PBMCs) were incubated for 30 min at 4° C. with 0.5 μg/mL tetramer (H-2db tetramers containing the OVA peptide, SIINFEKL), in a 1:100 diluted anti-CD3 antibody, and 1:100 diluted anti-CD8 antibody (Thermo Scientific). Cells were washed twice and fixed in 2% paraformaldehyde. At least 100,000 cells were acquired on the Beckman Coulter FC 500 flow-cytometer and analyzed using the CXP software. Gating was done on CD8+ cells, and percentage of CD3+/CD8+/tetramer+ cells was determined.

Figure 10A:
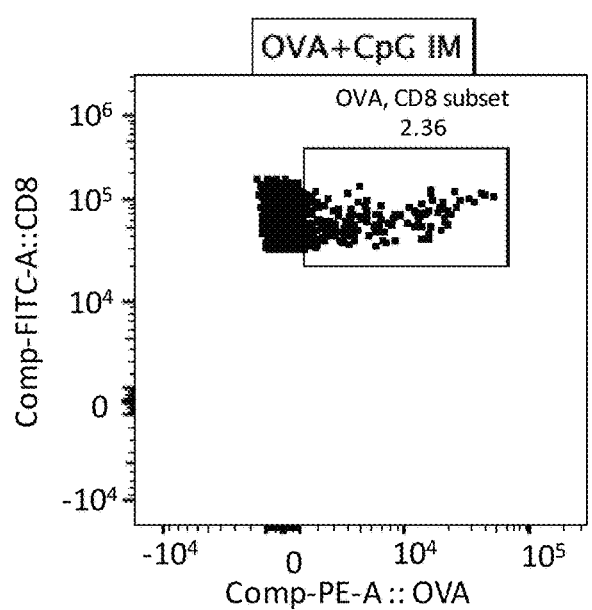
Figure 10B:
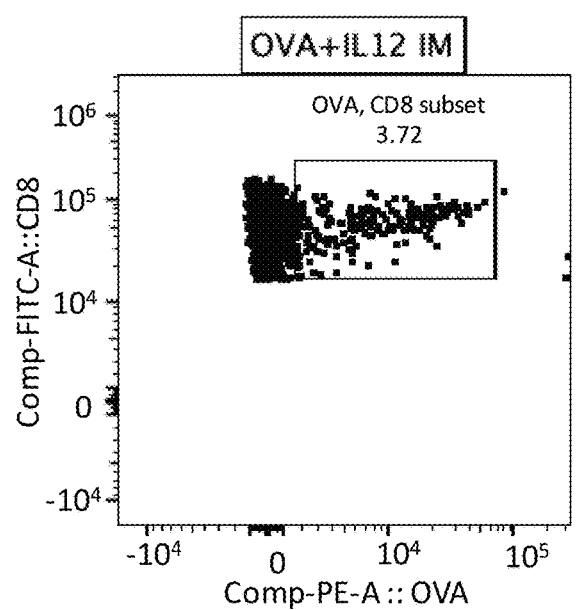
Figure 10C:
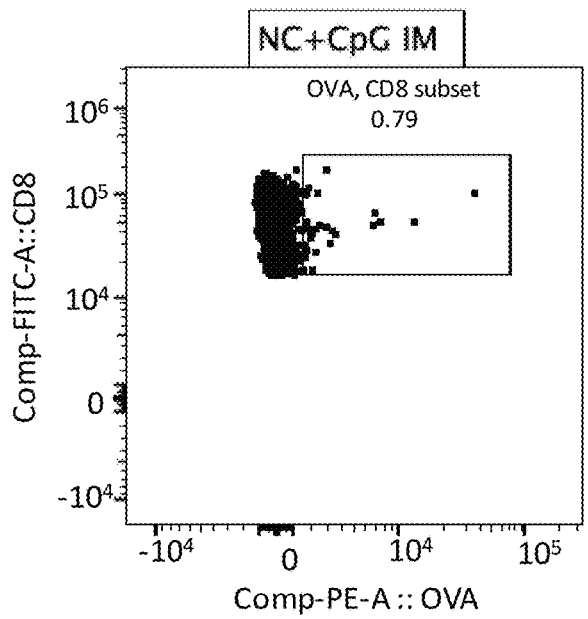
Figure 10D:
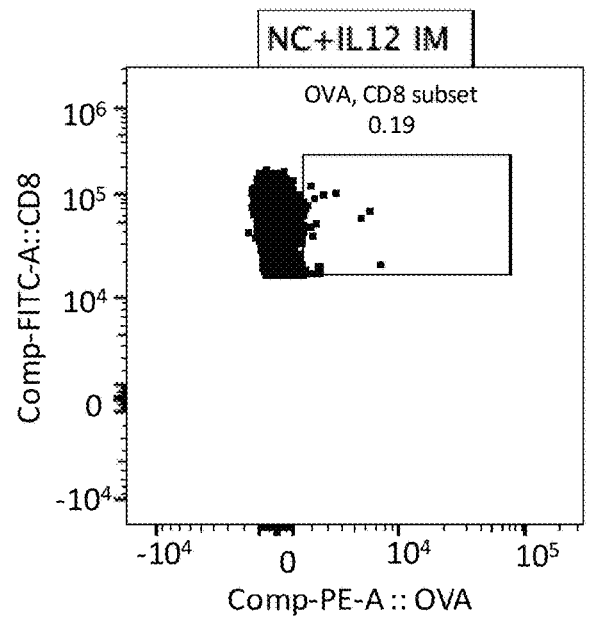

FIGS. 10A-10G and 11A-11F show the results of intramuscular injection. Flow cytometry was used to measure OVA-specific T-cells in circulation using the OVA peptide (SIINFEKL). Measurements were performed after one dose (on day 11) and after three doses (on day 28), from blood. FIGS. 10A-10G illustrate the results of intramuscular (IM) injection, as described above, at day 11, after the first dose. FIG. 10A corresponds to group 6 (OVA+CpG, intramuscular), FIG. 10B corresponds to group 7 (OVA+IL-12, intramuscular), FIG. 10C corresponds to group 8 (non-coding mRNA+CpG, intramuscular), FIG. 10D corresponds to group 9 (non-coding mRNA+IL-12, intramuscular) and FIG. 10E corresponds to group 10 (OVA+IL-12+GM-CSF, intramuscular). FIGS. 10F and 10G show controls.

Figure 11A:
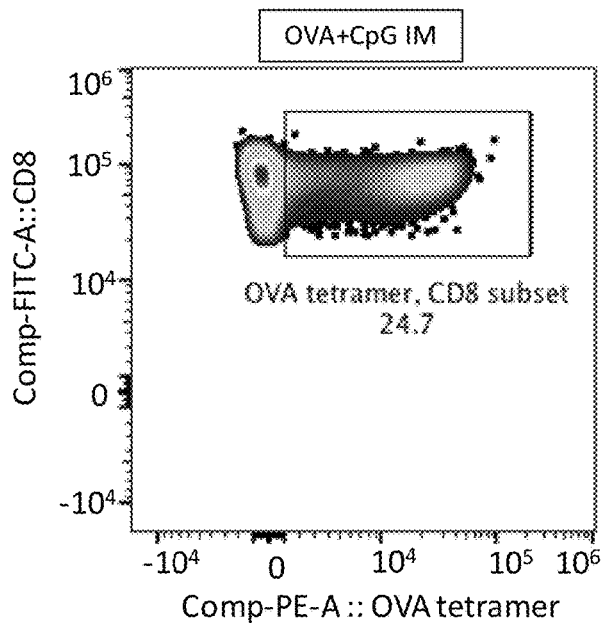
FIGS. 11A-11F illustrate the results of different nanoparticle compositions (as described in FIG. 9) intramuscularly injected in a mouse lymphoma tumor model at day 28.
Figure 11B:
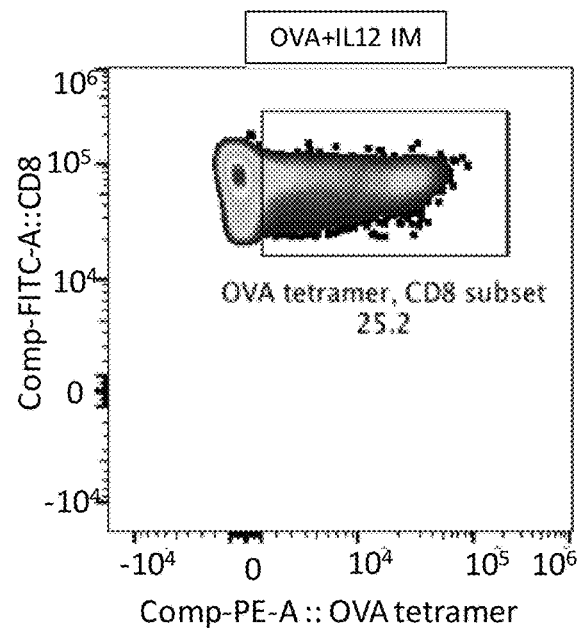
Figure 11C:
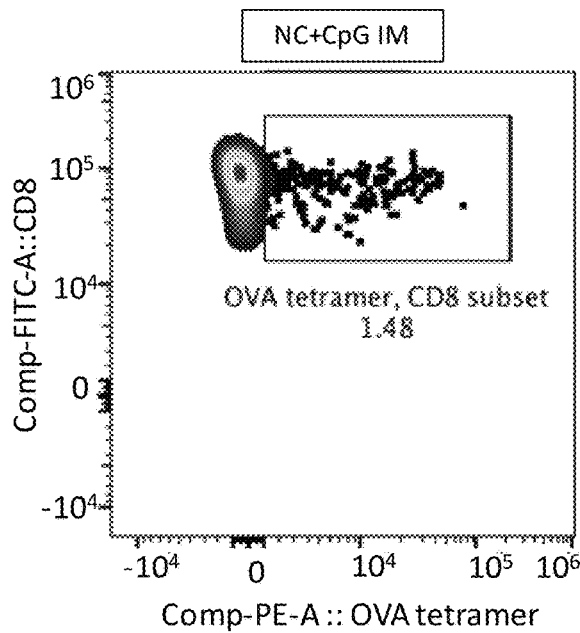
Figure 11D:
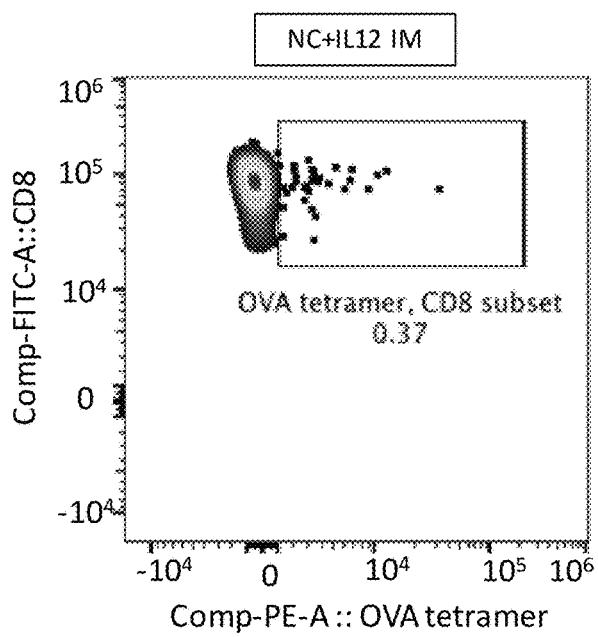
Figure 11E:
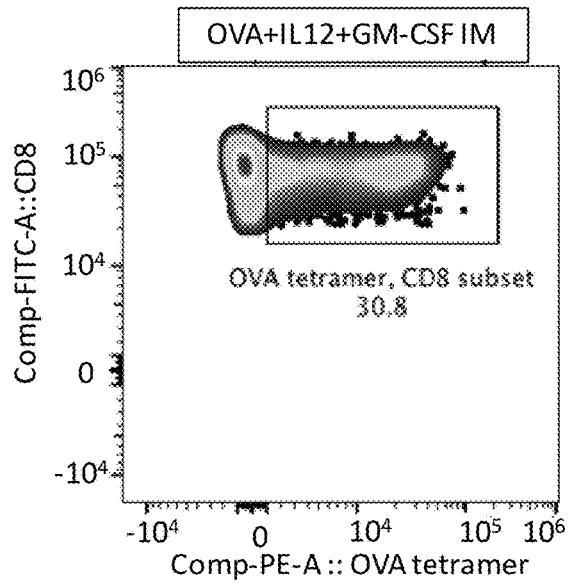
Figure 11F:
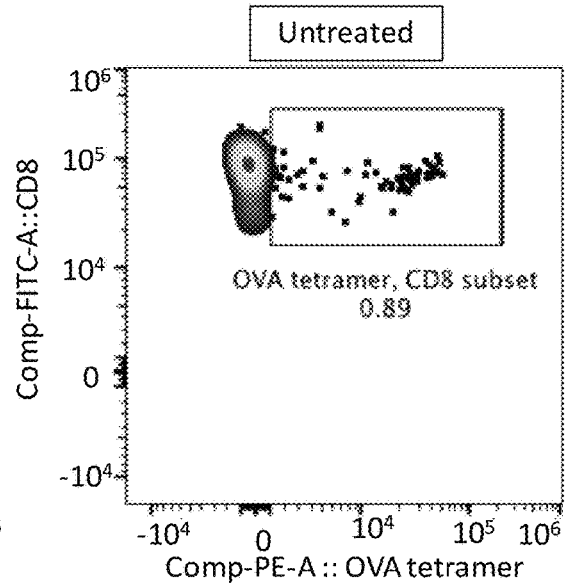

Similarly, FIGS. 11A-11G show flow cytometry results for OVA-specific T-cells in circulation using the SIINFEKL tetramer after the third IM dose (on day 28). FIG. 11A corresponds to group 6 (OVA+CpG, intramuscular), FIG. 11B corresponds to group 7 (OVA+IL-12, intramuscular), FIG. 11C corresponds to group 8 (non-coding mRNA+CpG, intramuscular), FIG. 11D corresponds to group 9 (non-coding mRNA+IL-12, intramuscular) and FIG. 11E corresponds to group 10 (OVA+IL-12+GM-CSF, intramuscular). FIG. 11F shows a control group.

As shown in FIGS. 10A-10G and 11A-11F, effectors alone did not drive robust expansion of the tumor-specific CD8+ T-cell population (see, e.g., FIGS. 10C-10D and 11C-11D). However, the when the antigen was combined with an immunomodulatory agent (e.g., a pro-inflammatory cytokine, such as IL-12) and/or an immunostimulator such as CpG, for example by combining, in the same delivery vehicle the mRNA for the antigen and the immunomodulator, about 25% of the circulating CD8+ T-cells were tumor specific by day 28. In this example, both IL-12 and CpG showed a similar expansion of tumor-specific CD8 T cells.

Figure 12A:
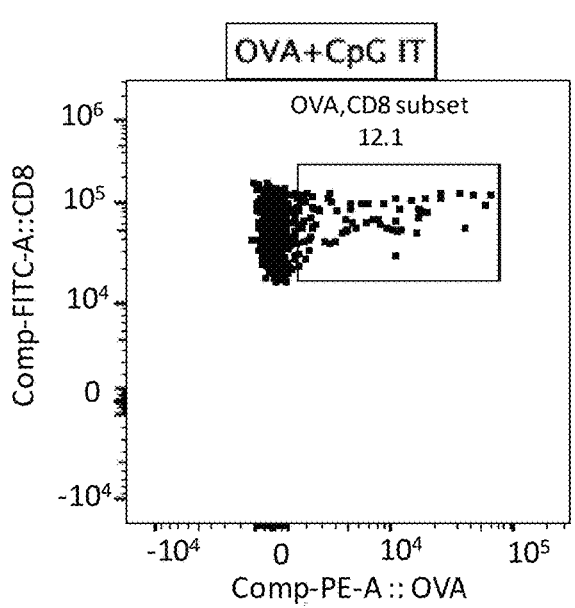
FIGS. 12A-12G illustrate the results of different nanoparticle compositions (as described in FIG. 9) intratumorally injected in a mouse lymphoma tumor model at day 11.
Figure 12B:
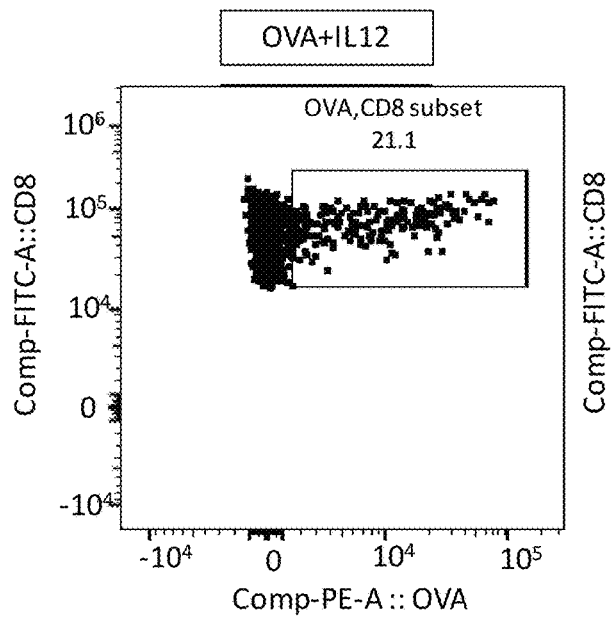
Figure 12C:
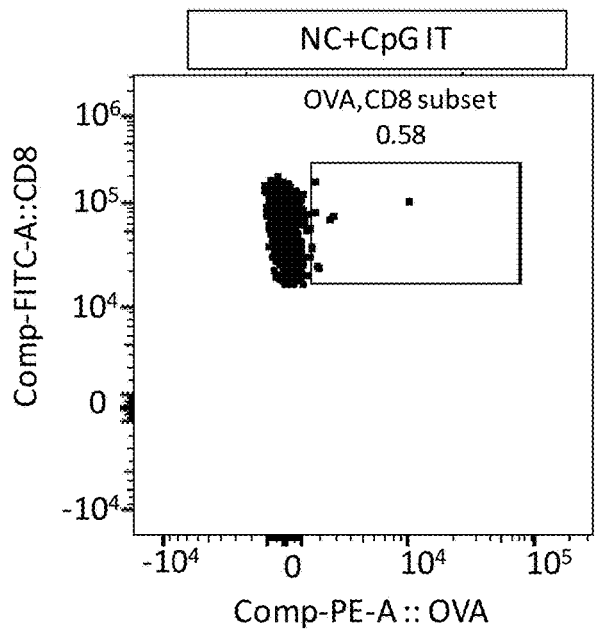
Figure 12D:
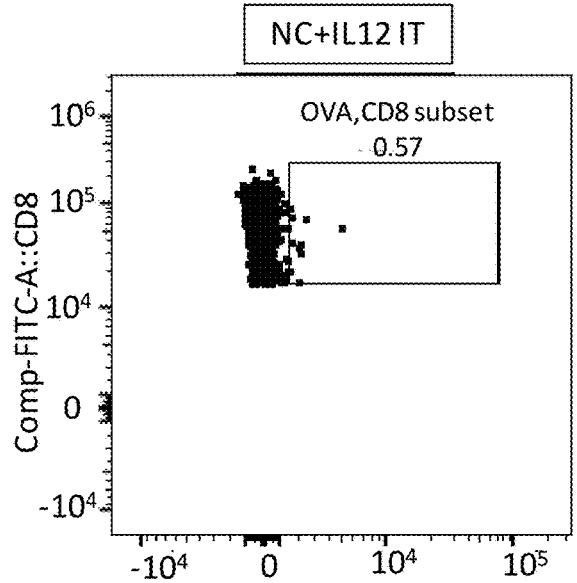
Figure 12E:
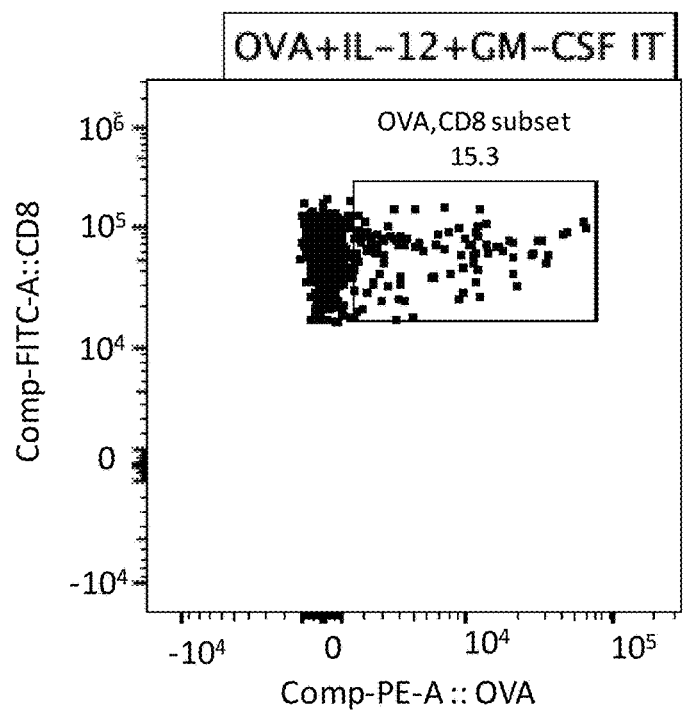
Figure 12F:
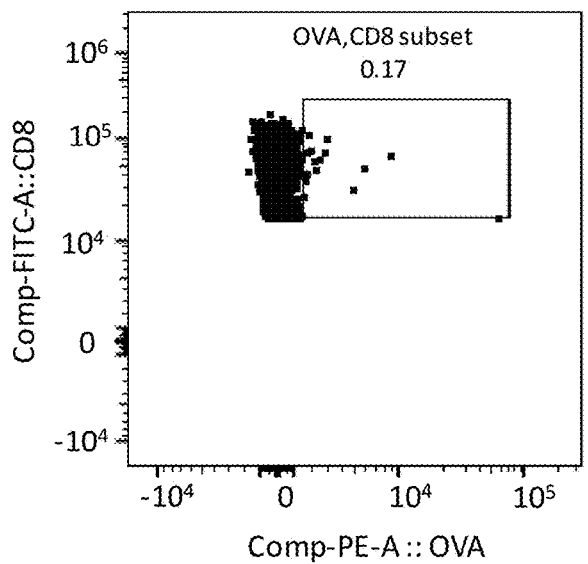
Figure 12G:
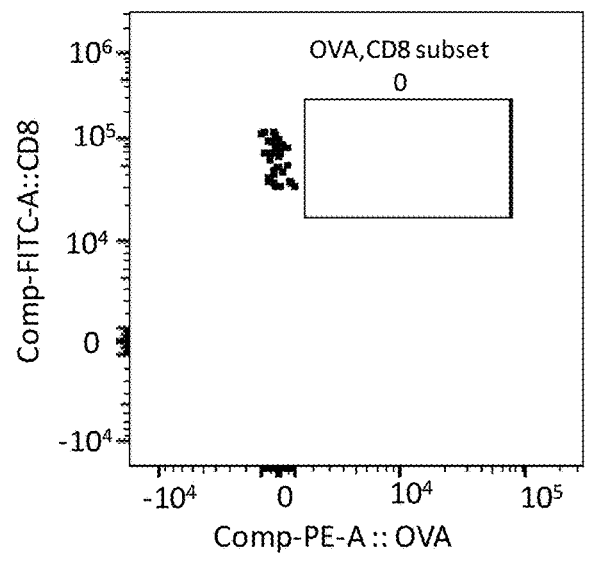

FIGS. 12A-12G and 13A-13F show the results of intratumoral (IT) injection. Flow cytometry was used to measure OVA-specific T-cells in circulation using the OVA peptide (SIINFEKL). Measurements were performed after one dose (on day 11) and after three doses (on day 28), from blood. FIGS. 12A-12G illustrate the results of intratumoral injection, as described above, at day 11, after the first dose. FIG. 12A corresponds to group 1 (OVA+CpG, intramuscular), FIG. 12B corresponds to group 2 (OVA+IL-12, intramuscular), FIG. 12C corresponds to group 3 (non-coding mRNA+CpG, intramuscular), FIG. 12D corresponds to group 4 (non-coding mRNA+IL-12, intramuscular) and FIG. 12E corresponds to group 5 (OVA+IL-12+GM-CSF, intramuscular). FIGS. 12F and 12G show controls.

Figure 13A:
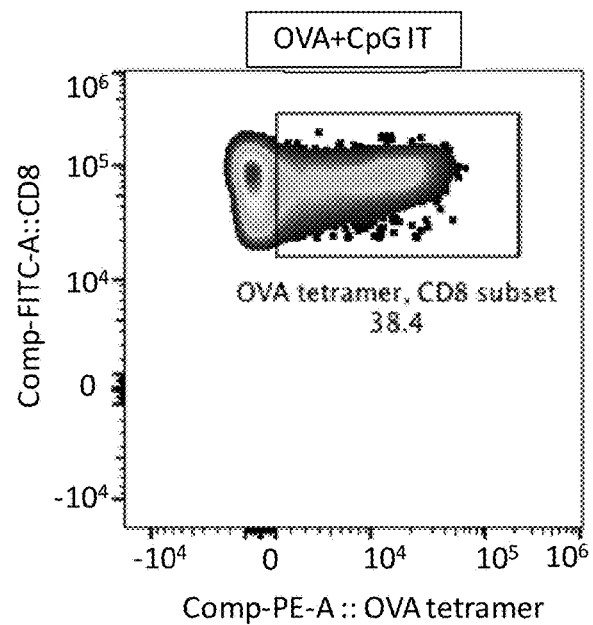
FIGS. 13A-13F illustrate the results of different nanoparticle compositions (as described in FIG. 9) intratumorally injected in a mouse lymphoma tumor model at day 28.

FIGS. 13A-13G show flow cytometry results for OVA-specific T-cells in circulation using the SIINFEKL tetramer after the third IT dose (on day 28). FIG. 13A corresponds to group 1 (OVA+CpG, intramuscular), FIG. 13B corresponds to group 2 (OVA+IL-12, intramuscular), FIG. 13C corresponds to group 3 (non-coding mRNA+CpG, intramuscular), FIG. 13D corresponds to group 4 (non-coding mRNA+

Figure 13B:
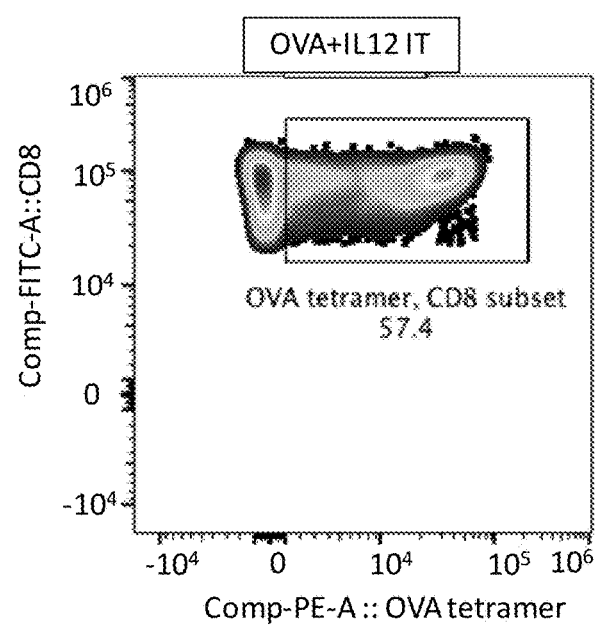
Figure 13C:
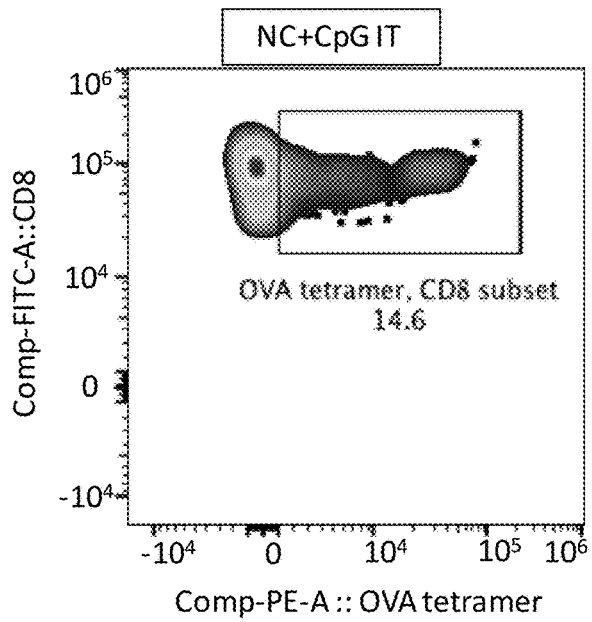
Figure 13D:
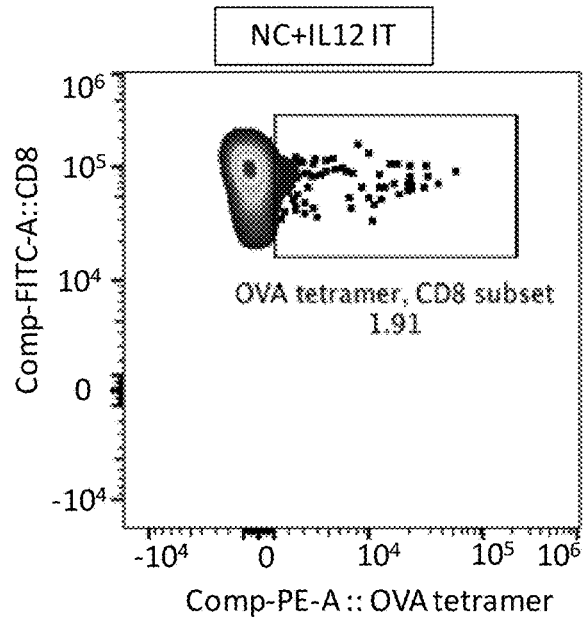
Figure 13E:
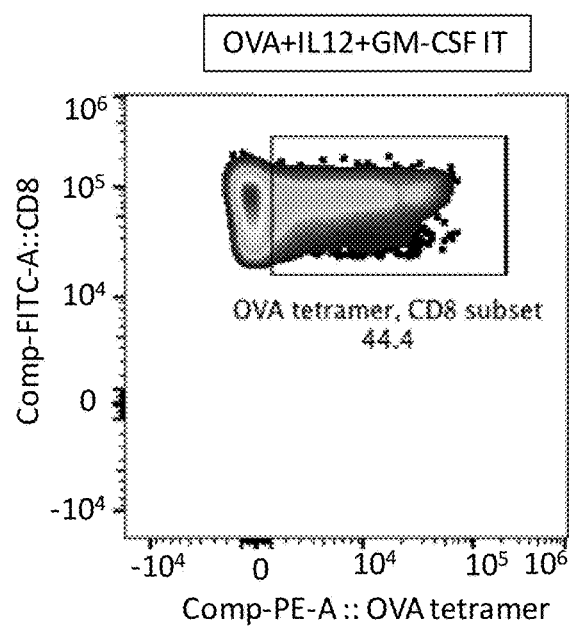
Figure 13F:
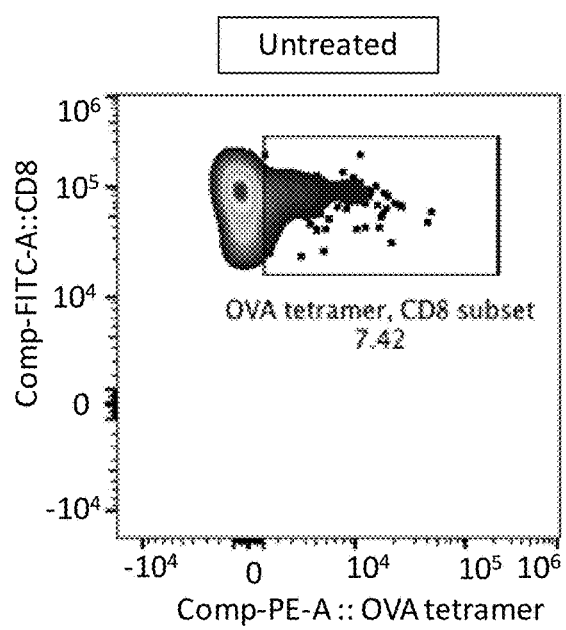

IL-12, intramuscular) and FIG. 13E corresponds to group 5 (OVA+IL-12+GM-CSF, intramuscular). FIG. 13F shows a control (untreated) group.

As shown in FIGS. 13A-13B and 13E, intratumoral (IT) injection of the antigen and an immunomodulator, such as a pro-inflammatory cytokine (e.g., IL-12) or an immunostimulator, such as CpG, in combination with the antigen-specific mRNA resulted in a stronger tumor-specific CD8 response as compared to intramuscular (IM) injections. For example, the intratumoral injection of a tumor-specific antigen combined with the pro-inflammatory cytokine (e.g., IL-12) on the same delivery vehicle resulted in a more robust response than the same composition injected intramuscularly. The use of a tumor antigen mRNA and an immunomodulator or immunostimulatory (combined together with the same delivery vehicle) resulted in about 25% of the circulating CD8+ T cells being tumor-specific at day 28. In this example, both the immunostimulatory (CpG) and the immunomodulator (pro-inflammatory immunomodulator, IL12) resulted in a similar expansion of tumor-specific CD8 T cells. For both intramuscular injection and intratumoral injection effectors (e.g., immunomodulators, immunostimulators, etc.) alone did not drive a robust expansion of the tumor-specific CD8+ T cell population, as shown for IT injection in FIGS. 13C and 13D.

Example 3: Tumor Implantation, Treatment and Surveillance

The therapeutic use of intratumoral injection using a tumor-specific antigen mRNA combined with the same immunomodulator mRNA (e.g., a pro-inflammatory immunomodulator such as IL-12) or an immunosuppressor (e.g., CpG) was also examined in an animal model.

Groups of ten 8-week-old female C57BL/6 mice were challenged subcutaneously (s.c.) in the right flank with $1 \times 10^5$ EG. 7 tumor cells in PBS. Throughout the duration of the experiments, tumor growth was monitored two to three times per week with a caliper in two dimensions. Mice were euthanized when tumor volume exceeded 1,500 mm$^3$ or when ulcerated. Both intratumoral and intramuscular injections were performed. For example, intratumor therapeutic vaccination with 2 µg of nanoparticle formulated with mRNA in 20 ul was injected on days 7, 14, and 28 after tumor challenge. Six variations were used: (1) tumor-specific antigen (OVA) mRNA plus immunomodulator (IL-12) mRNA; (2) tumor-specific antigen (OVA) mRNA, immunomodulator (IL-12) mRNA, and a second immunomodulatory agent (GM-CSF) mRNA; (3) tumor specific antigen (OVA) mRNA and an immunosimulator (CpG); (4) immunomodulator (IL-12) mRNA alone (without a tumor antigen mRNA); (5) immunosimulator (CpG) alone (without a tumor antigen mRNA); and (6) PBS. The same six variants were examined with both intratumoral and intramuscular experiments. For intramuscular injection, the therapeutic vaccination was also performed with 2 ug nanoparticle formulated RNA in 20 ul on days 7, 14, and 28 after tumor challenge. No treatment-related toxicities were noted in these experiments, and tumor growth was monitored for 60 days.

Figure 14:
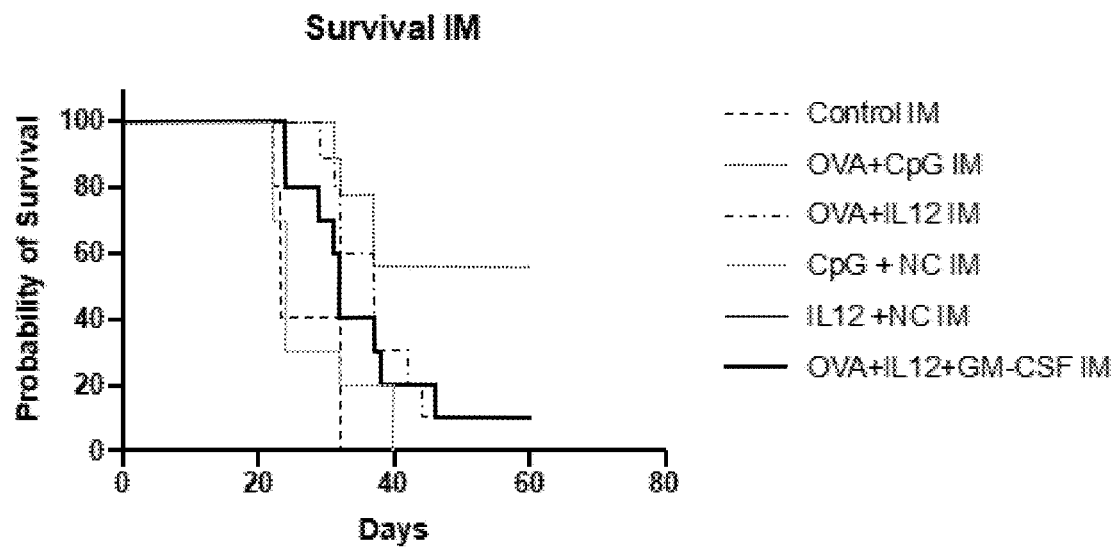
FIG. 14 is a graph showing probability of survival in a mouse lymphoma tumor model intramuscularly injected with different nanoparticle compositions.

FIG. 14 summarizes the results for probability of survival following tumor injection when treated by intramuscular (IM) injection with one of the six variations described above. As shown, the control animals were all dead before day 40, as were animals treated with just immunostimulatory injection (CpG). The probability of survival by day 60 (end point) was highest for animals immunized with the tumor specific antigen (OVA) mRNA and an immunosimulator (CpG), followed by immunomodulator (IL-12) mRNA alone (without a tumor antigen mRNA), and then tumor-specific antigen (OVA) mRNA, immunomodulator (IL-12) mRNA, and a second immunomodulatory agent (GM-CSF) mRNA, and tumor-specific antigen (OVA) mRNA plus immunomodulator (IL-12) mRNA.

Figure 15:
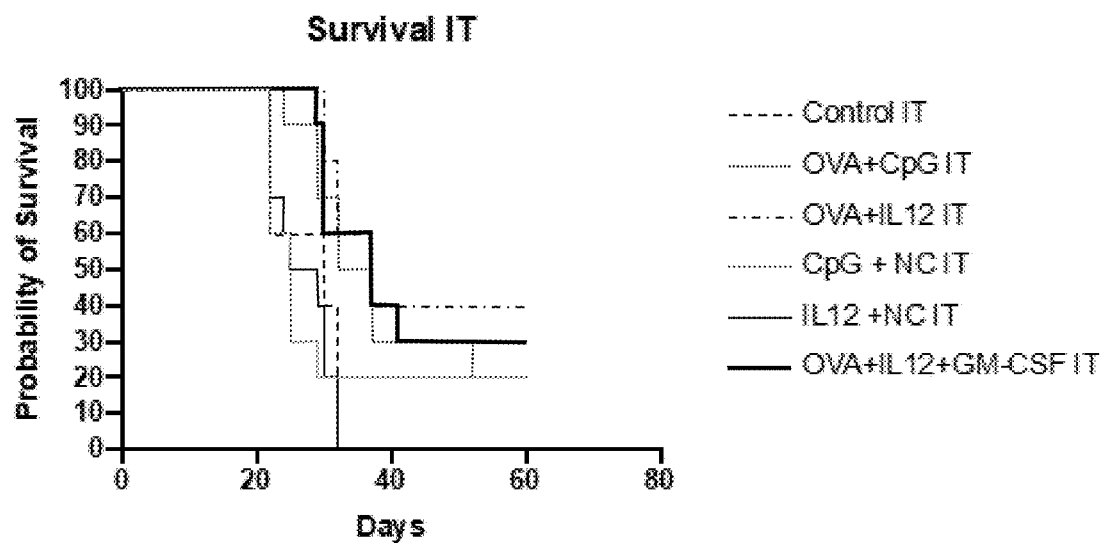
FIG. 15 is a graph showing probability of survival in a mouse lymphoma tumor model intratumorally injected with different nanoparticle compositions.

FIG. 15 shows the results for intratumoral injection of these same variations described above. In this example, the animals having tumors that were immunized with either control (PBS) or with the immunomodulator (IL-12) mRNA alone (without tumor antigen) did not survive to 40 days. The overall survivability of animals immunized with the tumor-specific antigen (OVA) mRNA plus immunomodulator (IL-12) mRNA was highest (40%), followed by animals immunized with tumor-specific antigen (OVA) mRNA, immunomodulator (IL-12) mRNA, and a second immunomodulatory agent (GM-CSF) mRNA (30%), then animals immunized with tumor specific antigen (OVA) mRNA and an immunosimulator (CpG) or immunosimulator (CpG) alone (without a tumor antigen mRNA) (both 20%).

Figure 16:
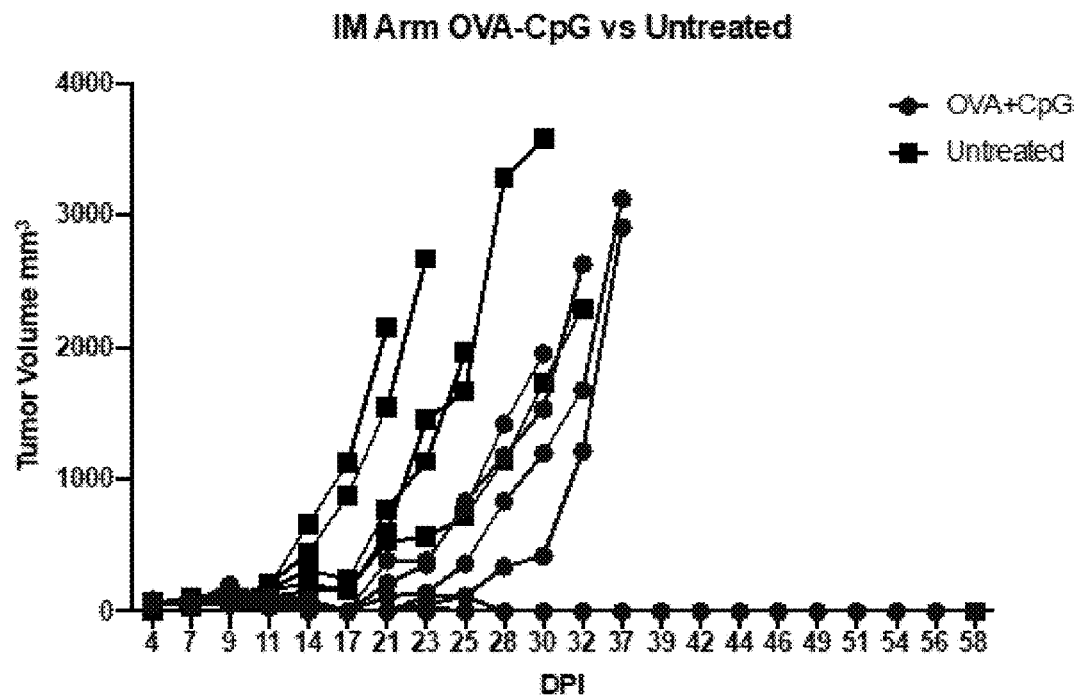
FIG. 16 illustrates the change in tumor volume over time for lymphoma tumors in mice injected intramuscularly with either control (untreated) PBS solution, or with tumor specific antigen (OVA) mRNA and an immunosimulator (CpG).

FIGS. 16-20 are graphs showing the tumor volume change over time for each of the intramuscular treatment groups examined above. For example, FIG. 16 is a graph showing the change in tumor volume over time for the tumors of mice injected with either control (untreated) PBS solution, or with a nanoparticle composition including tumor specific antigen (OVA) mRNA and an immunosimulator (CpG). There mice injected with tumor specific antigen (OVA) mRNA combined with an immunosimulator (CpG) either showed no significant tumor volume (e.g., tumors did not grow) or the grew more slowly.

Figure 17:
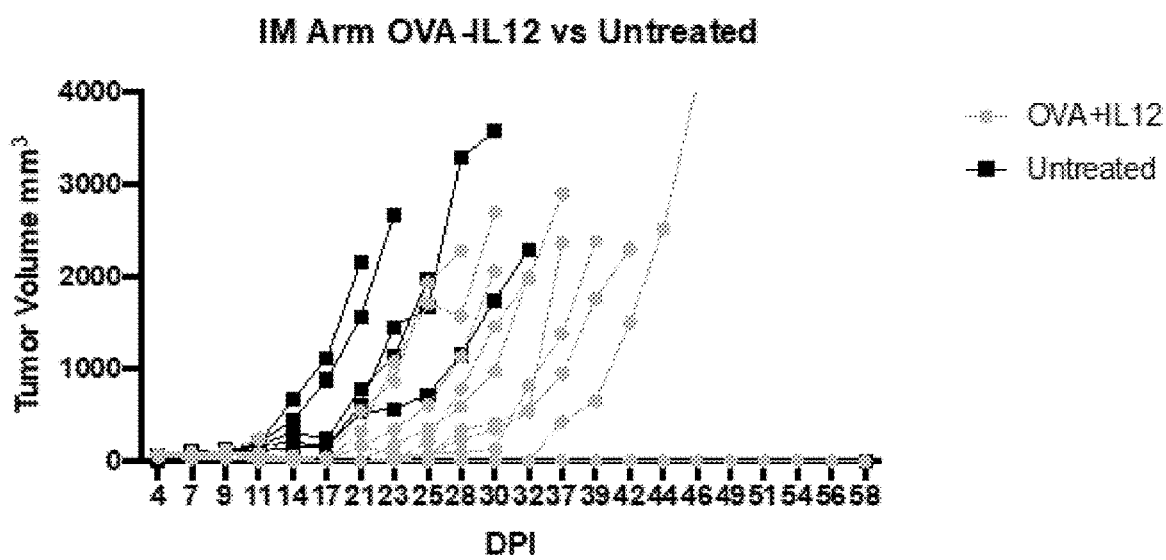
FIG. 17 illustrates the change in tumor volume over time for lymphoma tumors in mice injected intramuscularly with either control solution (PBS), or with a nanoparticle composition containing both tumor-specific antigen (OVA) mRNA plus immunomodulator (IL-12) mRNA.

FIG. 17 shows the change in tumor volume over time for tumors of mice injected intramuscularly (IM) with either control solution (PBS), or with delivery vehicles containing both tumor-specific antigen (OVA) mRNA plus immunomodulator (IL-12) mRNA. As shown in FIG. 17, some tumors did not grow, while the majority of the tumors in the mice treated with tumor-specific antigen (OVA) mRNA plus immunomodulator (IL-12) mRNA grew more slowly.

Figure 18:
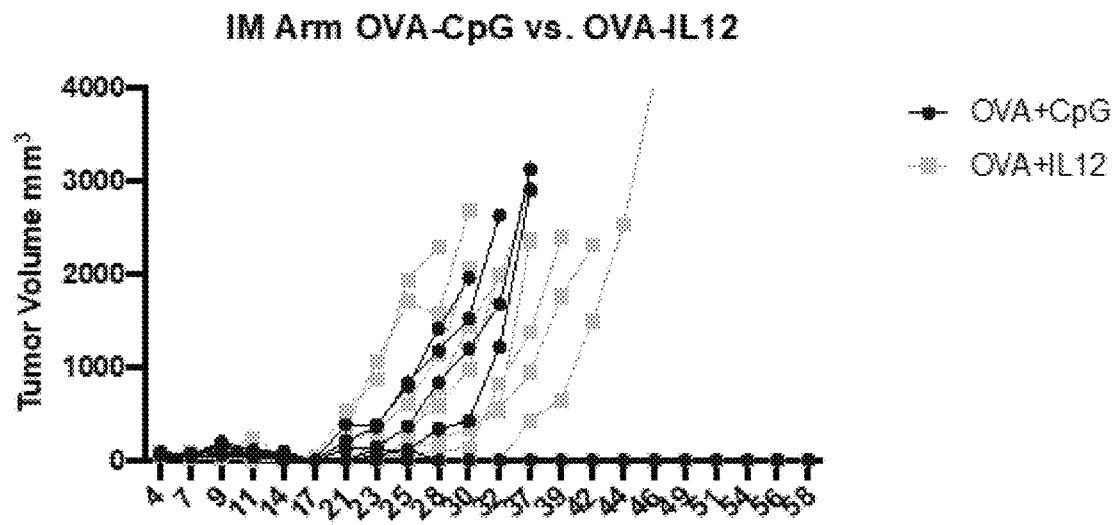
FIG. 18 illustrates the change in tumor volume over time for lymphoma tumors in mice injected intramuscularly with tumor specific antigen (OVA) mRNA and an immunosimulator (CpG), or with immunosimulator (CpG) alone (without a tumor antigen mRNA).

FIG. 18 shows the change in tumor volume for mice receiving intramuscularly (IM) injection with tumor specific antigen (OVA) mRNA and an immunosimulator (CpG), and tumors from mice injected with immunosimulator (CpG) alone (without a tumor antigen mRNA). There is substantial overlap in the tumor volume over time between these two groups.

Figure 19:
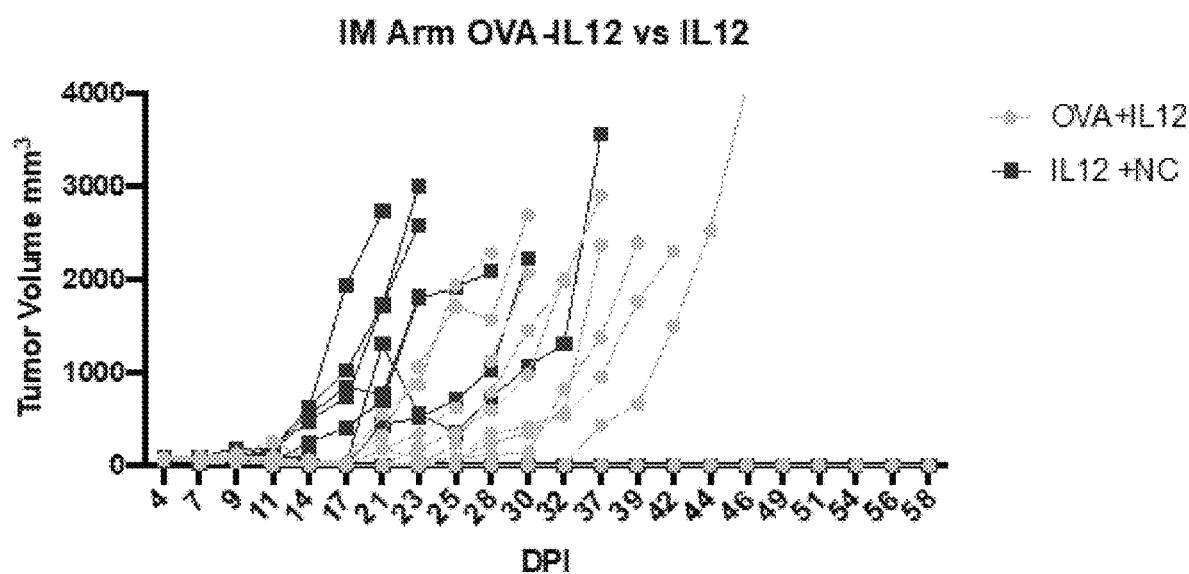
FIG. 19 illustrates the change in tumor volume over time for lymphoma tumors in mice injected intramuscularly with a nanoparticle composition of a tumor-specific antigen (OVA) mRNA plus immunomodulator (IL-12) mRNA in the same delivery vehicle, or immunomodulator (IL-12) mRNA alone (without a tumor antigen mRNA).

FIG. 19 shows the change in tumor volume over time between mice treated by intramuscular injection with a nanoparticle composition including tumor-specific antigen (OVA) mRNA plus immunomodulator (IL-12) mRNA in a delivery vehicle and a nanoparticle composition including immunomodulator (IL-12) mRNA alone (without a tumor antigen mRNA).

Figure 20:
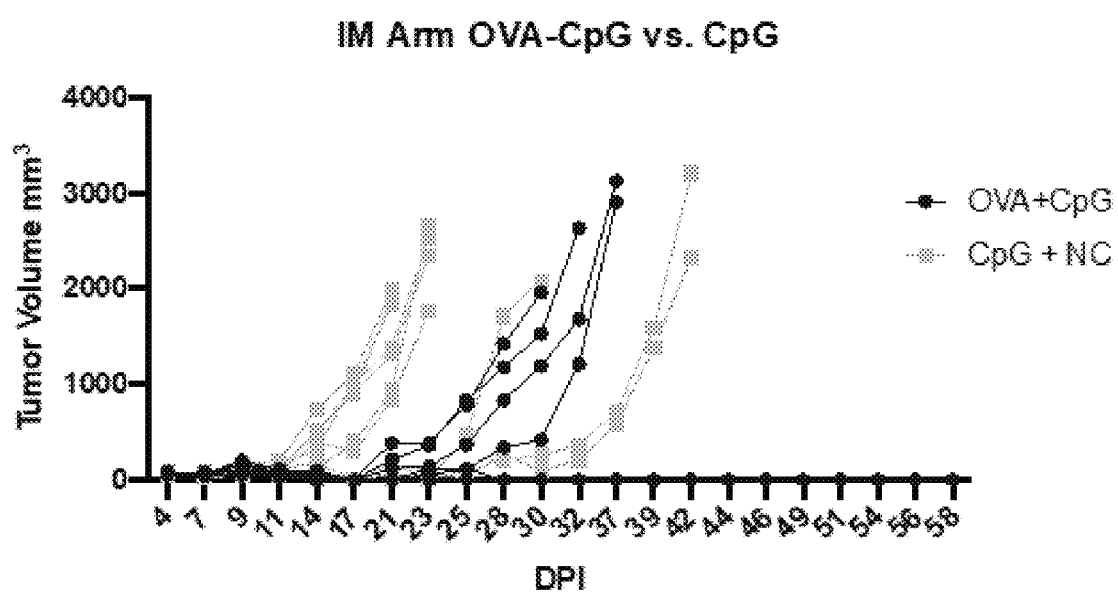
FIG. 20 illustrates the change in tumor volume over time for lymphoma tumors in mice injected intramuscularly with a nanoparticle composition of a tumor specific antigen (OVA) mRNA and an immunosimulator (CpG) or with immunosimulator (CpG) alone (without a tumor antigen mRNA).

FIG. 20 is a comparison between tumor volume of mice injected intramuscularly (IM) by either tumor specific antigen (OVA) mRNA and an immunosimulator (CpG) or by immunosimulator (CpG) alone (without a tumor antigen mRNA).

Figure 21:
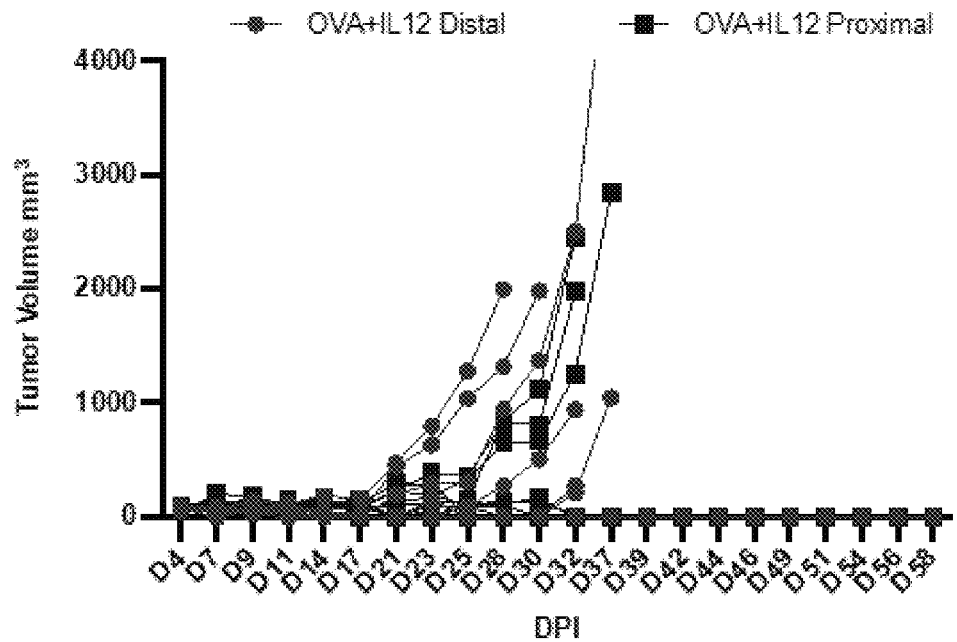
FIG. 21 is a graph comparing the change in tumor volume over time between tumors treated by intratumoral injection ("proximal" tumors) of a nanoparticle composition of tumor antigen and immunomodulator (e.g., IL-12) with tumors from the same animal that were not intratumorally injected with the nanoparticle composition ("distal" tumors).
Figure 22:
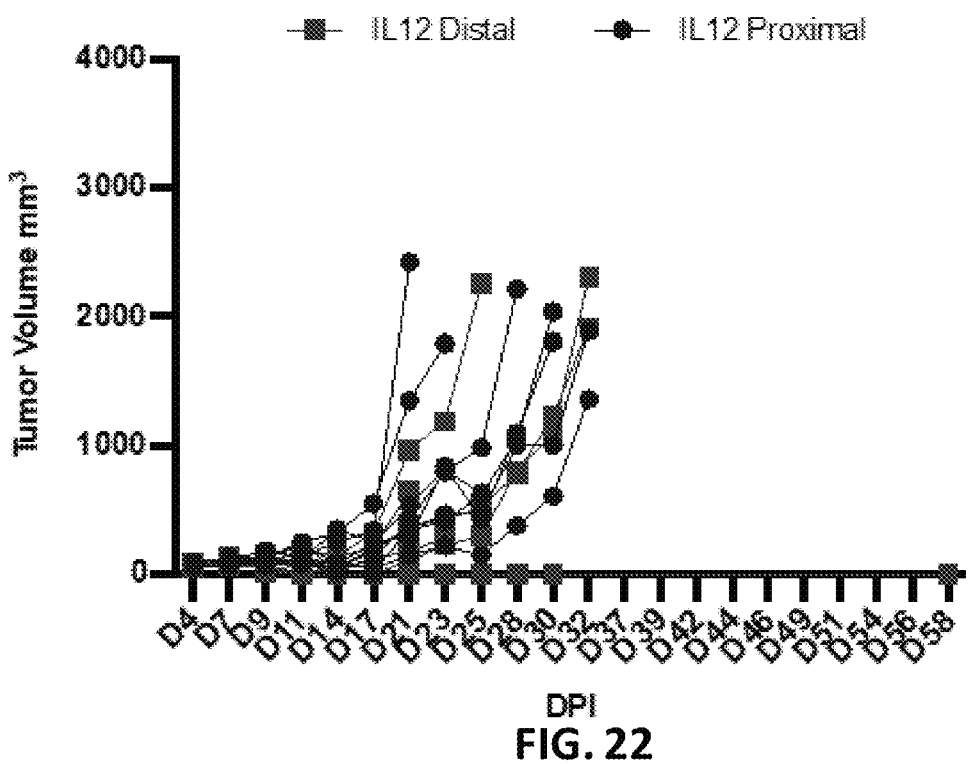
FIG. 22 is a graph comparing the change in tumor volume over time between tumors treated by intratumoral injection ("proximal" tumors) of a nanoparticle composition of just immunomodulator (e.g., IL-12) with tumors from the same animal that were not intratumorally injected with the nanoparticle composition ("distal" tumors).

In some experiments the same animal may include multiple induced tumors some of which may be treated by intratumoral injection ("proximal" tumors) or may be untreated ("distal") in the same animal. FIG. 21 shows the change in tumor volume for tumors that either received intratumoral injections of tumor-specific antigen (OVA) mRNA plus immunomodulator (IL-12) mRNA, as compared to tumors in the same animal that did not receive intratumoral injections into the tumor. FIG. 22 shows a change in tumor volume between proximal and distal tumors when proximal tumors from the same animals, were injected with immunomodulator (IL-12) mRNA alone (without a tumor antigen mRNA).

Figure 23:
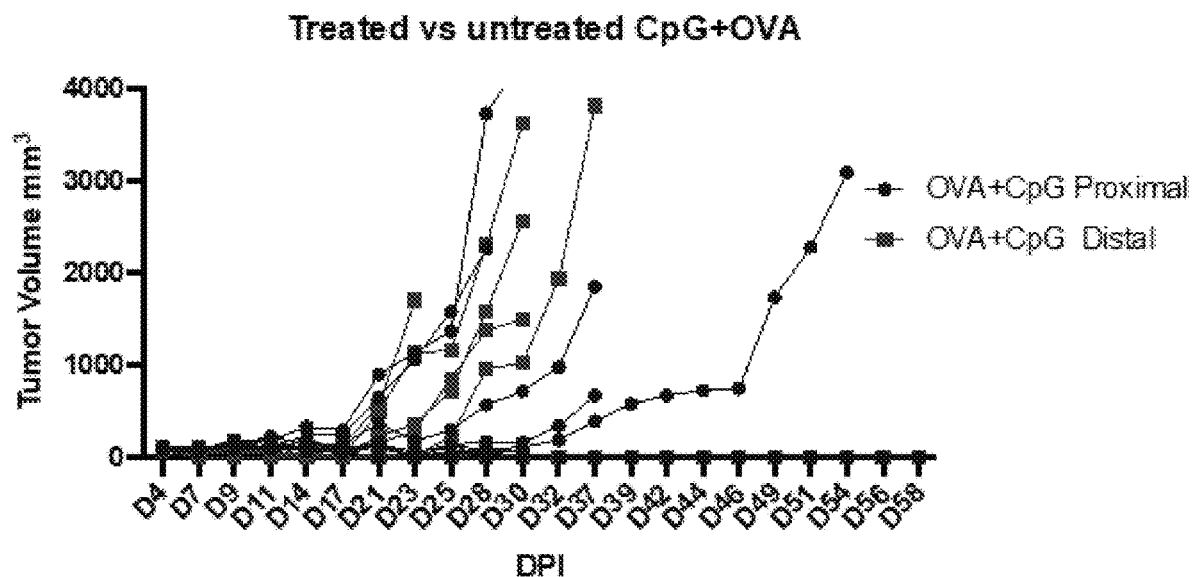
FIG. 23 is a graph comparing the change in tumor volume over time between tumors treated by intratumoral injection ("proximal" tumors) of a nanoparticle composition of tumor antigen and immunostimulator (e.g., CpG) with tumors from the same animal that were not intratumorally injected with the nanoparticle composition ("distal" tumors).

FIG. 23 also shows changes in tumor volume for treated (proximal) and untreated (distal) mice in the same animals injected with tumor specific antigen (OVA) mRNA and an immunosimulator (CpG). The proximal tumors received the injection into the tumor, while the distal tumors were in the same animal but did not receive intratumoral injections of the delivery vehicle and OVA mRNA with CpG. A portion of the tumors treated with tumor specific antigen (OVA) mRNA and an immunosimulator (CpG) grew more slowly or did not grow, as compared with the distal (un-injected) tumors.

Figure 24:
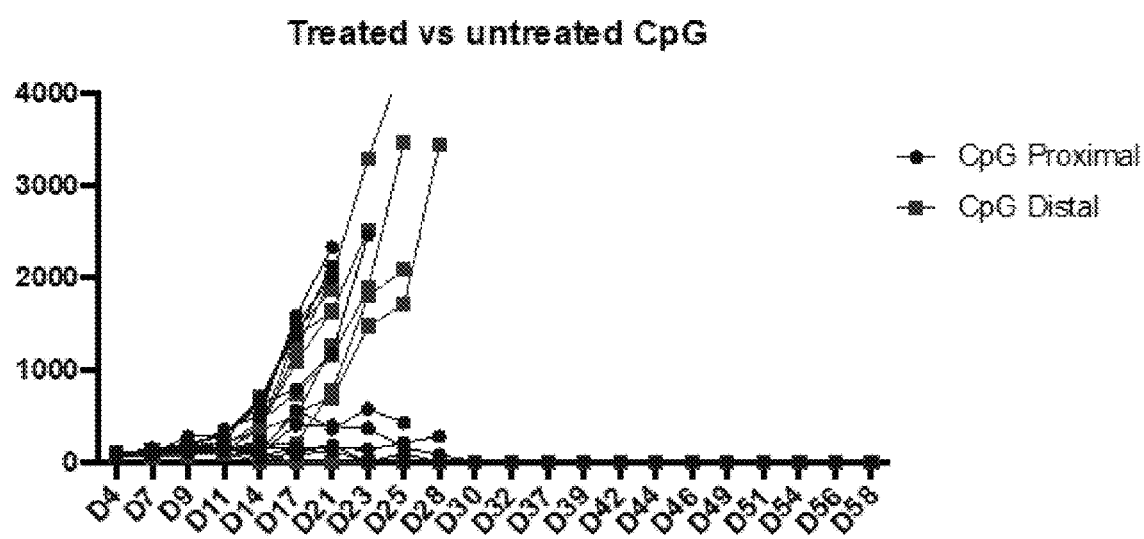
FIG. 24 is a graph comparing the change in tumor volume over time between tumors treated by intratumoral injection ("proximal" tumors) of a nanoparticle composition of just immunostimulator (e.g., CpG) with tumors from the same animal that were not intratumorally injected with the nanoparticle composition ("distal" tumors).
Figures 25, 26:
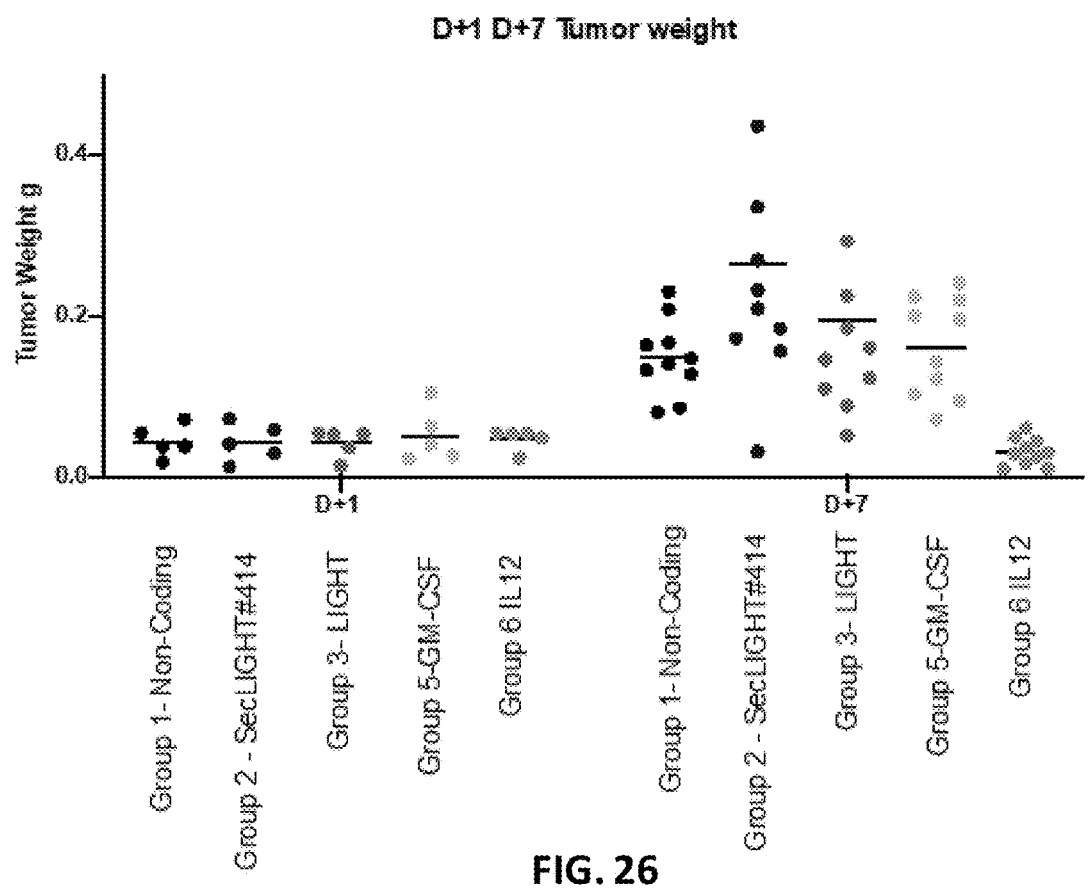
FIG. 25 is a table (table 2) summarizing the response rate of EG. 7 tumors.
FIG. 26 is a graph illustrating the effect of various immunomodulatory agents (e.g., effectors) on tumor volume of MC38 tumor cells.

In FIG. 24, the majority of the proximal tumors that received the intratumoral injection (in this example: an immunosimulator (CpG) alone) had slowed, or reversed growth, while distal tumors mostly continued to grow in the same mice. FIG. 25 is a table (Table 2) summarizing the results of the data related to FIGS. 16-24. As shown, the intratumoral injection of the delivery vehicles containing both tumor-specific antigen (OVA) mRNA and immunomodulator (IL-12) mRNA had the most robust response rate for injected tumors (e.g., 70%), while maintaining a distal tumor effect (of 50%). The overall response of both proximal (injected) and distal (non-injected, same animal as proximal) in these animals was about 40%. The same assays found no significant effect in the response rate for just the immunomodulator (e.g., the inflammatory cytokine, IL-12). An effect was also seen with tumor-specific antigen (OVA) mRNA with an immunostimulatory, CpG (e.g., 50% response rate of the proximal tumor, and 50% for distal tumor). The overall response of both proximal and distal tumors to tumor-specific antigen (OVA) mRNA plus immunostimulatory agent (CpG) was about 20%. Intratumoral injection of CpG alone has a smaller effect (e.g., 30% proximal, 20% distal and 20% overall).

As used herein, a response is an end-point tumor volume of <5% compared to the tumor volume of the contralateral tumor upon that tumor reaching end-point volume. For example, when one of two tumors in the same mouse reaches the end-point volume (e.g., tumor 1 is 1500 mm$^3$), and the contralateral tumor (tumor 2) is only 75 mm$^3$, that is considered a response in Tumor 2.

Experiment 4: MC38 Colon Carcinoma Sub Cutaneous Tumors

MC38 colon cancer tumors were established in test animals (mice) and treated with nanoparticles to determine the effect of effectors (e.g., immunomodulators and immunostimulators) including in the absence of a tumor-specific antigen.

Figure 27:
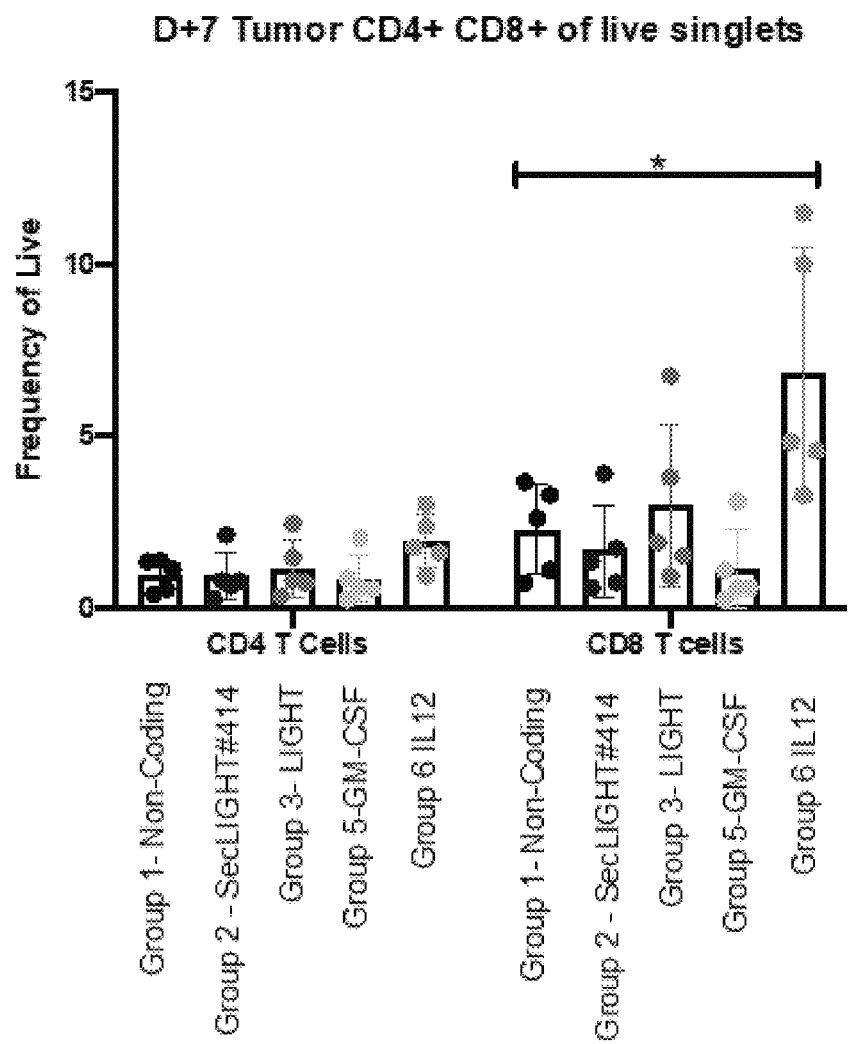
FIG. 27 is a graph summarizing the frequency of CD8 T cells in tumors treated with various immunomodulatory agents as described herein.
Figure 28:
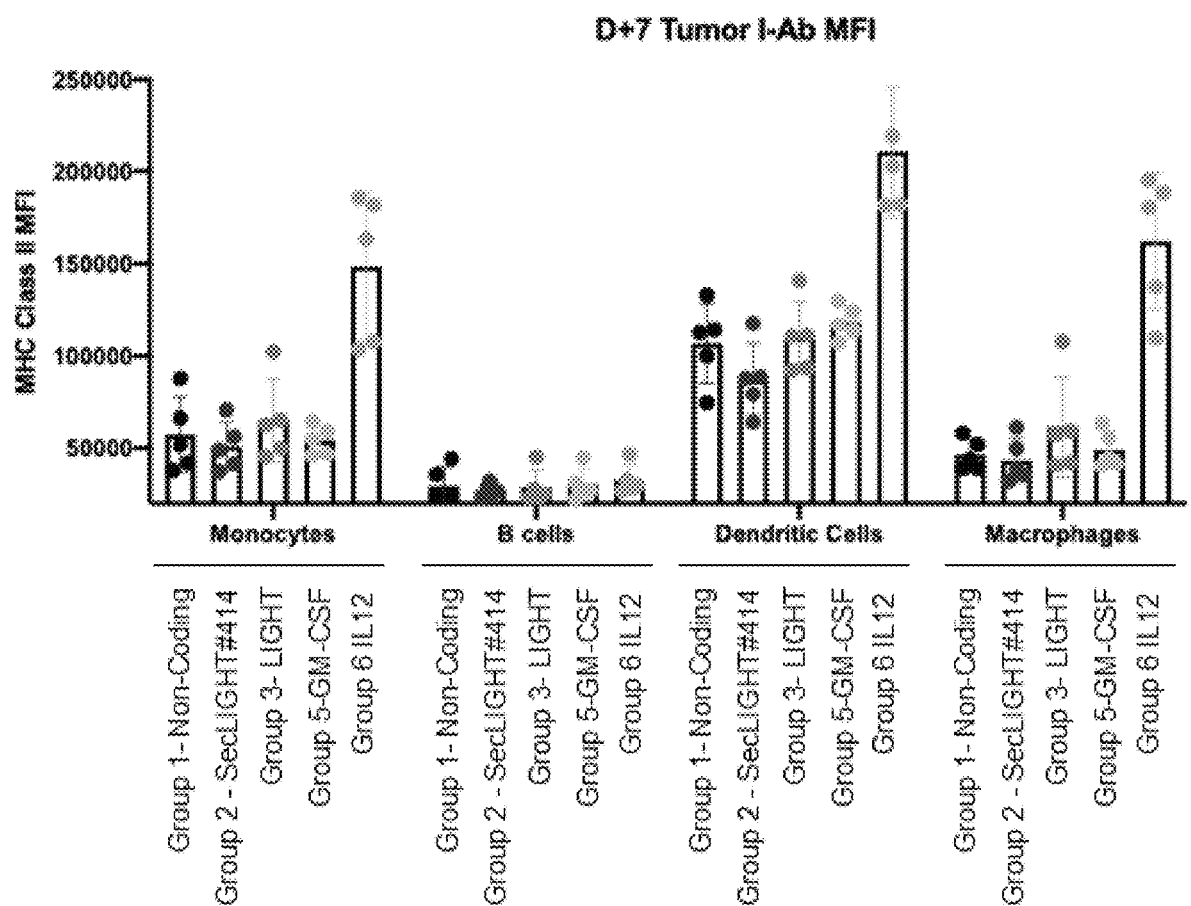
FIG. 28 is a graph of the number of antigen-presenting cells following treatment with various immunomodulator agents as described herein.

Tumors were treated with a nanoparticle formulated with an immunomodulator and an immunostimulatory mRNA on Days 6 and 10 after implantation of a tumor. Nanoparticles are delivery vehicle including one or more immunomodulator, immunostimluator and/or tumor-specific antigen. For example FIGS. 26-28 illustrate the effect of nanoparticles including non-coding RNA controls, secreted LIGTH (e.g., TNFRSF14), native LIGHT, immunomodulator GM-CSF, and/or immunomodulator (e.g., pro-inflammatory cytokine IL-12 on induced MC38 tumors and mice having such tumors. Injected animals had tumors and tumor-draining lymph nodes analyzed for changes in Tumor Microenvironment induced by the immunomodulator and/or immunostimulator. LIGHT refers to tumor necrosis factor superfamily member 14 (TNFSF14), also called CD258, which is another example of an immunomodulator as described herein.

As part of the protocol, groups of 5-10 8-week-old female C57BL/6 mice were challenged subcutaneously (s.c.) in the right flank with 1×10$^5$ MC38 tumor cells in PBS. Intratumor therapeutic vaccination with 2 µg nanoparticle formulated RNA in 20 ul was given on day 7 and day 11 after tumor challenge. Tested compositions included nanoparticles of immunomodulator (e.g., pro-inflammatory cytokine, IL-12) mRNA, GM-CSF immunomodulatory mRNA, immunomodulatory secreted LIGHT mRNA, immunomodulatory native LIGHT mRNA, and control PBS. Tumors were harvested following scheduled euthanization of the mice, as were the tumor draining lymph nodes. Flow cytometric analysis of Tumor immune cell infiltrate and immune activation was assessed by flow cytometry. No treatment-related toxicities were noted. Tumor growth was monitored for 60 days.

FIG. 26 shows the effect of various immunomodulatory agents (e.g., effectors) on tumor volume of MC38 tumor cells. In FIG. 26, the effect of intratumoral injection of delivery vehicle including either control (non-coding mRNA), or an immunomodulatory agent (secreted LIGHT, LIGTH, GM-CSF, or IL-12) is shown at D1 and at day 7 following challenge. The IL-12 group (group 6) showed a difference as compared to control.

There was an increase in CD8 T cell frequency in tumors from animals treated by intratumoral injection with IL-12, as shown in FIG. 27. In this example, the frequency of live T cells positive for both CD4 and CD8 on day 7 following the tumor challenge was significantly larger in tumors intratumorally injected with a delivery vehicle including IL-12. In general, there was a significant increase in antigen-presenting cells following intratumoral injection with IL-12, as compared with other immunomodulators and control by day 7, as shown in FIG. 28, in monocytes, B-cells, dendritic cells and macrophages. Thus, a pro-inflammatory cytokine such as IL-12, when injected intratumorally (and as shown above, particularly when combined in the same delivery vehicle as a tumor-specific antigen) was found to enhance the anti-tumor response even as compared to other immunomodulators.

Example 5: C3.43 Tumor Cells

C3.43 is an HPV16-transformed tumor model. A tumor-specific antigen (HPV 16 oncoproteins E6 and E7) may be used with C3.43 tumors. This model was also used to show the effectiveness of tumor-specific antigen mRNA combined in the same delivery vehicle with one or more immunomodulator mRNA, such as (but not limited to) a pro-inflammatory cytokine (e.g., IL-12).

Groups of ten 8-week-old female C57BL/6 mice were challenged s.c. in the right flank with 5×10$^5$ C3.43 tumor cells in PBS. Throughout the duration of the experiments, tumor growth was monitored two to three times per week with a caliper in three dimensions. Mice were euthanized when tumor volume exceeded 1,500 mm$^3$ or when ulcerated. Intratumor therapeutic vaccination with 2 µg nanoparticle formulated RNA in 20 µl on days 18, 25, and 32 after tumor challenge. Six different nanoparticle formulations were examined: (1) tumor-specific antigen (HPV16 E6E7) mRNA with an immunomodulator (pro-inflammatory cytokine IL-12) mRNA; (2) tumor-specific antigen (HPV16)

mRNA, a first immunomodulator (LIGHT) mRNA and a second immunomodulator (pro-inflammatory cytokine IL-12) mRNA; (3) tumor-specific antigen (HPV16) mRNA and an immunostimulator (CpG); (4) immunomodulator (pro-inflammatory cytokine IL-12) mRNA; (5) a first immunomodulator (LIGHT) mRNA and a second immunomodulator (pro-inflammatory cytokine IL-12) mRNA; (6) immunostimulator (CpG); (7) control (PBS). The first nanoparticle solution, tumor-specific antigen (HPV16 E6E7) mRNA with an immunomodulator (pro-inflammatory cytokine IL-12) mRNA, was also injected intramuscularly. No treatment-related toxicities were noted. Tumor growth was monitored for 60 days.

Figure 29:
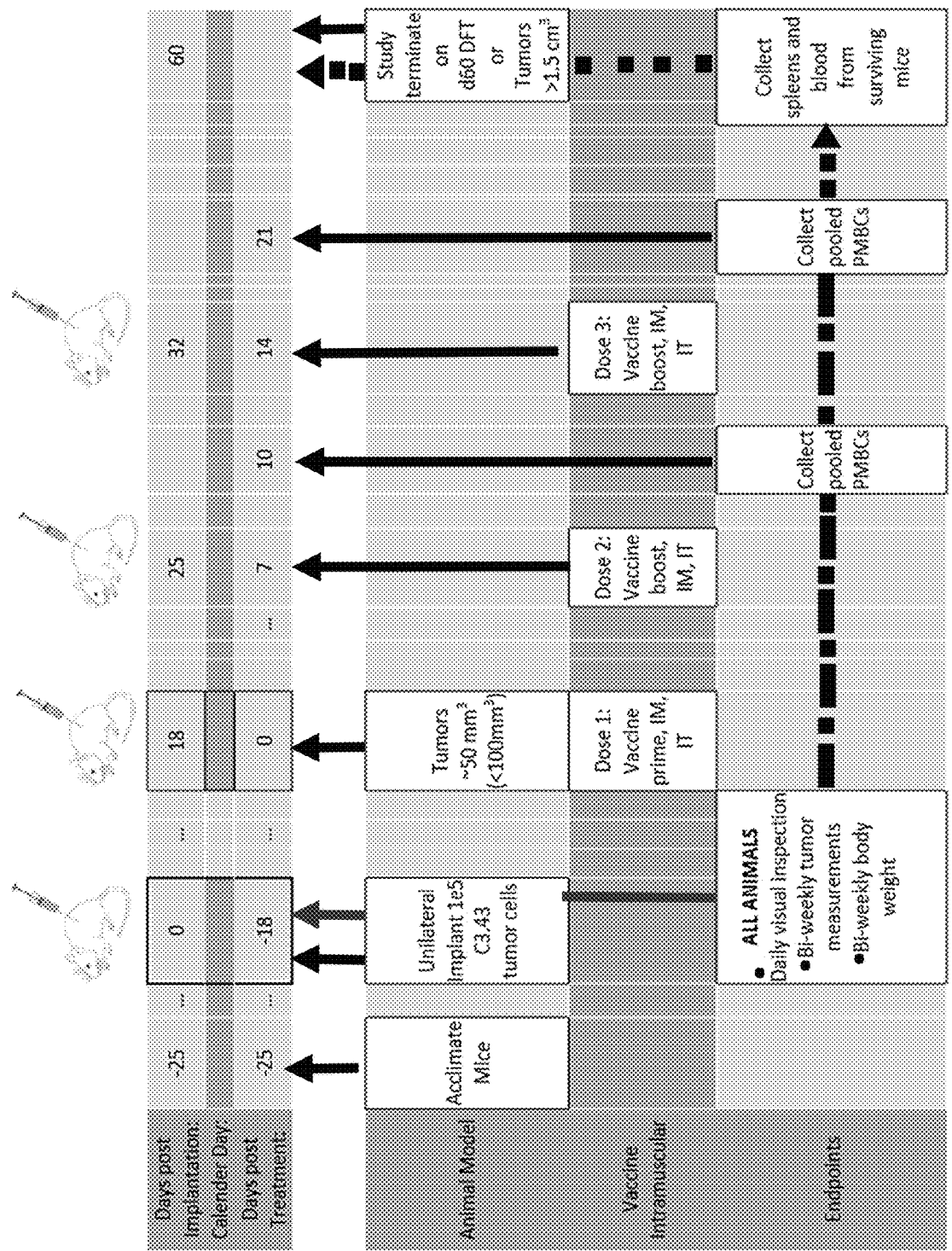
FIG. 29 illustrates one example of a study timeline that may be used to examine the effects of nanoparticle compositions as described herein.

FIG. 29 illustrates one example of a study timeline that may be used to examine the effects of nanoparticle compositions as described herein. This timeline is similar to that used for the experiments described in examples 2-4, above. Mice (e.g., C57BL6 female mice, 6-8 weeks old) are unilateral challenged by s.c. in right hind limb with $1 \times 10^5$ tumor cells (such as, in this example, C3.43 tumor cells) in 100 µL HBSS on day 0. Dosing injections were done by unilateral i.m. in right hind limb or IT. For ten groups, n=10 mice/group. Mice were monitored for tumor growth, significant body weight reduction (measured weekly), and exterior signs of distress (humane endpoints).

Figures 30A, 30B, 30C, 30D, 30E, 30F:
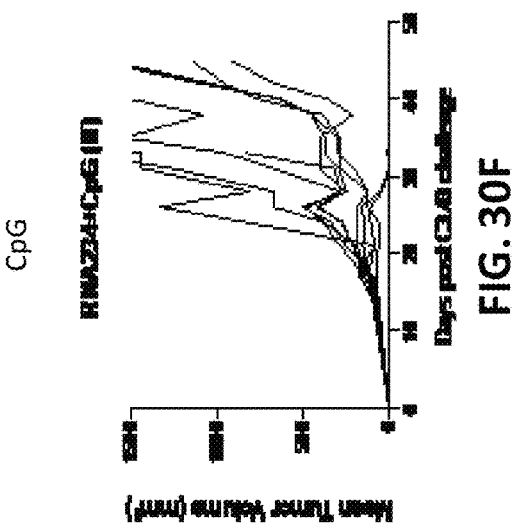
FIGS. 30A-30F each illustrate the time course of tumor growth following intratumoral injection with one of the nanoparticle compositions described herein on C3.43 tumors.

FIGS. 30A-30F each show the results for individual tumors intratumorally injected with one of the nanoparticle solutions described above using a protocol such as that shown in FIG. 29. For example, FIG. 30A shows the effect of intratumoral injection in C3.43 tumors of the first nanoparticle solution, including tumor-specific antigen (HPV16 E6E7) mRNA with an immunomodulator (pro-inflammatory cytokine IL-12) mRNA, showing a reduction in mean tumor volume for nearly all of the tumors examined. FIG. 30B shows the effect of intratumoral injection of the second nanoparticle solution, including tumor-specific antigen (HPV16) mRNA, a first immunomodulator (LIGHT) mRNA and a second immunomodulator (pro-inflammatory cytokine IL-12) mRNA, showing an almost complete reduction in mean tumor volume. FIG. 30C shows smaller effect of the third nanoparticle solution, the tumor-specific antigen (HPV16) mRNA and an immunostimulator (CpG).

FIG. 30D shows the effect of intratumoral injection of a nanoparticle solution including an immunomodulator (pro-inflammatory cytokine IL-12) mRNA without a tumor-specific antigen on mean tumor volume. FIG. 30E shows the effect of intratumoral injection on mean tumor volume of a nanoparticle solution including a first immunomodulator (LIGHT) mRNA and a second immunomodulator (pro-inflammatory cytokine IL-12) mRNA (again, without a tumor antigen). FIG. 30F shows the effect of intratumoral injection on mean tumor volume for just the immunostimulator (CpG).

FIGS. 31A and 31B show the results of intramuscular injection of the first nanoparticle solution, including tumor-specific antigen (HPV16 E6E7) mRNA with an immunomodulator (pro-inflammatory cytokine IL-12) mRNA. In contrast to intratumoral injection of the same composition, intramuscular injection did not result in a reduction in mean tumor volume. FIG. 31B shows the result of control treatment (e.g., PBS), showing a time-dependent increase in mean tumor volume.

FIG. 32 is a comparison of the probability of survival for the various nanoparticle compositions described above. Nanoparticles including both the tumor antigen (e.g., HPV16 E6E7 in this model) and at least one immunomodulator, and particularly a pro-inflammatory cytokine immunomodulator such as IL-12, or IL-12 with a second immunomodulator such as LIGHT, when injected intratumorally, showed complete, or nearly complete survival. Intramuscular injection of the same combination of tumor antigen and IL-12 did not result in survival beyond 60 days.

CD8 T-cell responses to the various nanoparticle compositions described herein were examined. H-2db tetramers containing the HPV16 E7 (49-57) peptide were used. Individual mice were bled on day 39 after challenge. Single-cell suspensions of circulating Peripheral Blood Mononuclear Cells (PBMCs) were incubated for 30 min at 4° C. with 0.5 µg/mL tetramer, 1:100 diluted anti-CD3 antibody, and 1:100 diluted anti-CD8 antibody. Cells were washed twice and fixed in 2% paraformaldehyde. At least 100,000 cells were acquired on a Beckman Coulter FC 500 flow-cytometer and analyzed using the CXP software. Gating was done on CD8+ cells, and percentage of CD3+/CD8+/tetramer+ cells was determined. Percent tetramer positive CD8 T cells provides a biomarker for the therapeutic intervention's ability to induce tumor-specific immunity.

Figure 33:
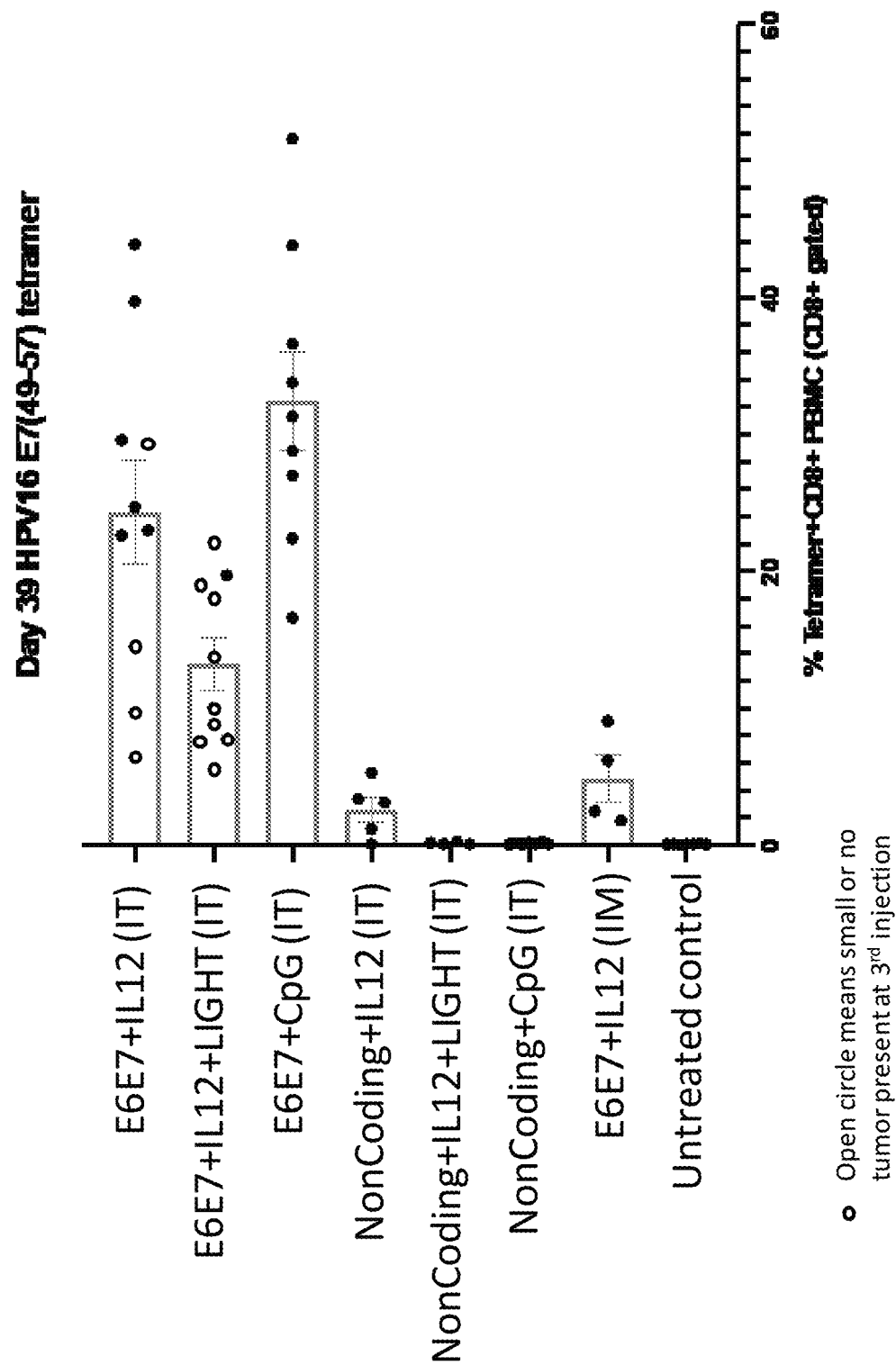
FIG. 33 is a graph showing that intratumoral injection of certain nanoparticle compositions as described herein result in an increase in the percentage of CD3+/CD8+/tetramer+ cells in circulation of the treated animal.

FIG. 33 graphically illustrates the results, showing that intratumorally injected nanoparticles in which a tumor antigen (in this example, HPV16 E6E7) was combined in nanoparticles with an immunomodulator or an immunostimulator, a significant percentage of CD3+/CD8+/tetramer+ cells were identified from the mice. The percentage of tetramer positive CD8 T cells provides a biomarker for the ability of the therapeutic intervention to induce tumor-specific immunity.

In FIG. 33, the open circles represent tumors in which small or no tumor was present at the third injection, which occurred in both the first and second nanoparticle solutions. As shown in FIG. 37, the nanoparticles with both tumor antigen mRNA and an immunomodulator (e.g., IL-12 or IL-12 with LIGHT) or an immunostimluator (e.g., CpG) resulted in a robust activation of tumor-specific T-cells in circulation.

Method of Making (e.g., Fabricating, Synthesizing) mRNA Treatment Nanoparticles

Any of the mRNA therapies described herein (including any of the mRNA treatment nanoparticles) may be fabricated using a closed-path system; the closed-path system may include a biochip (e.g., a microfluidic path device), that may be operated in a sealed, sterile, and closed environment to rapidly and accurately synthesize the mRNA treatment nanoparticle (e.g., mRNA vaccine). For example, described herein are methods and apparatuses (e.g., systems, devices, etc.) for making mRNA therapies. In one, non-limiting example, the methods and apparatuses described herein may be used to produce a therapeutic mRNA treatment nanoparticle against a cancer-specific antigen active in Cutaneous T-Cell Lymphoma.

Thus, in general, described herein are automated, high-yield manufacturing methods for mRNA therapies, optionally deployed at point-of-care.

For example, a method of manufacturing an mRNA treatment nanoparticle composition using a closed-path system comprising a plurality of storage depots configured to be secured in sealed fluid communication with one or more microfluidic path devices, the method comprising: transporting reagents between one or more storage depots of the plurality of storage depots and a plurality of reactors on the one or more microfluidic devices in a closed fluidic path that is protected from atmospheric contact to perform, in the one or more microfluidic path devices, each of the processes of: forming a DNA template, performing in vitro transcription of therapeutic mRNA from the template, purifying the therapeutic mRNA, and combining the mRNA with a delivery vehicle.

A method of manufacturing an mRNA treatment nanoparticle composition using a closed-path system comprising a plurality of storage depots configured to be secured in sealed fluid communication with one or more microfluidic path devices (wherein the one or more microfluidic path devices comprise a plurality of reactors) may include: delivering a template precursor material from one or more storage depots to a first reactor region of the plurality of reactors and processing the template precursor material to prepare a template from the template precursor material; transferring the template to a second reactor region of the plurality of reactors and processing the template by in vitro transcription to form a therapeutic mRNA; and transferring the therapeutic mRNA to a third reactor region of the plurality of reactors and processing the therapeutic mRNA to combine it with a delivery vehicle to form the mRNA treatment nanoparticle composition, wherein materials including the template precursor material and delivery vehicle are delivered from the storage depots into the plurality of reactors without atmospheric contact.

A method of manufacturing an mRNA treatment nanoparticle (referred to herein generally as an mRNA treatment nanoparticle composition) using a closed-path system comprising a plurality of storage depots in sealed fluid communication with one or more microfluidic path devices (e.g., wherein the one or more microfluidic path devices comprise a plurality of reactors), may include: inducing fluidic flow to deliver a template precursor material from one or more storage depots to a first reactor region of the plurality of reactors and processing the template precursor material to prepare a template from the template precursor material; transferring the template to a second reactor region of the plurality of reactors and processing the template by in vitro transcription to form mRNA; transferring the mRNA to a third reactor region of the plurality of reactors and processing the mRNA to combine it with delivery vehicle to form the mRNA treatment nanoparticle composition; and transferring the mRNA product depot of the one or more storage depots, wherein the materials are delivered from the storage depots into the reactors of the microfluidic path device with sub-microliter precision and without atmospheric contact. In any of the methods described herein, any of the processes may be performed pneumatically, e.g., the fluidic flow may be induced pneumatically, the fluid may be transferred pneumatically, etc. Alternatively or additionally, fluid may be driven by mechanically, hydraulically, etc.

In any of these methods (and apparatuses for performing them) the closed-path system may automatically and continuously perform the components for the processes of forming a template, performing in vitro transcription of therapeutic mRNA from the template, purifying the therapeutic mRNA, and combining the mRNA with a delivery vehicle. The closed-path system may pneumatically control the performance of forming a template, performing in vitro transcription of therapeutic mRNA from the template, purifying the therapeutic mRNA, and combining the mRNA with a delivery vehicle. In some variations, the closed-path system pneumatically controls the performance of the process of forming a template, performing in vitro transcription of therapeutic mRNA from the template, purifying the therapeutic mRNA, and combining the mRNA with a delivery vehicle by deflecting one or more membranes within the one or more microfluidic path devices.

Any of the methods and apparatuses described herein may be configured to be set up and operate at a site of care, such as a hospital, clinic, etc. This may allow immediate/on-demand, patient-specific therapeutics to be custom manufactured to a particular patient. Alternatively or additionally, therapeutic molecules that are not specific to a particular patient may be formulated with delivery vehicles in a "patient-individualized" way. Because of the methods and apparatuses described herein, any of these methods may be performed very quickly. For example, the closed-path system may automatically and continuously perform the process of forming a template, performing in vitro transcription of therapeutic mRNA from the template, purifying the therapeutic mRNA, and combining the mRNA with a delivery vehicle in less than 5 days. Alternatively, the system may use a pre-made template as an input and perform the remaining processes in shorter time.

Combining the mRNA with a delivery vehicle (formulating the therapeutic) may further comprise dialyzing the mRNA treatment nanoparticle composition in the one or more microfluidic path devices to purify the mRNA treatment nanoparticle composition.

Any of these methods may further comprise concentrating the mRNA treatment nanoparticle composition on the one or more microfluidic path devices, and/or dialyzing the therapeutic.

Any appropriate delivery vehicle may be used, including, e.g., an amphipathic delivery vehicle molecule. For example, the amphipathic delivery vehicle molecule may comprise an amino-lipidated peptoid.

Alternatively or additionally in any of the methods and apparatuses described herein, mRNAs may be pre-made and stored (e.g., at about 10 degrees C., 4 degrees C., 0 degrees C., −10 degrees C., etc.) for some time. For example any of these methods and apparatuses for performing them may include a library of therapeutic mRNAs that may be individually or collectively (e.g., about 2, 3, 4, 5, 6, etc. or more individual therapeutic mRNAs may be combined and) encapsulated together to form an mRNA treatment nanoparticle composition. As described herein, an mRNA treatment nanoparticle composition may therefore be manufactured on demand and may be formulated just-in-time in a single or multiple mRNA treatment nanoparticle composition "cocktails".

Also described herein are methods for forming the template (e.g., the DNA template). For example, a method of making a synthetic double stranded DNA template for in vitro transcription using a closed-path system comprising a plurality of storage depots in sealed fluid communication with a microfluidic path device, may include: joining a synthetic gene of interest with a synthetic in vitro transcription facilitator cassette to create a synthetic circular ligated product; removing unreacted synthetic gene of interest and unreacted synthetic in vitro transcription facilitator cassette away from the synthetic circular ligated product; amplifying the circular ligated product to generate branched or circular amplified DNA; and linearizing the branched amplified DNA ligated product to generate double stranded DNA template, wherein each of the joining, removing, amplifying and linearizing processes are performed in the microfluidic path device by the closed-path system.

For example, a high-efficiency, automated method of making a synthetic double stranded DNA template for in vitro transcription, may include: pneumatically delivering each of: a synthetic gene of interest and a synthetic in vitro transcription facilitator cassette from one or more storage depots of a plurality of storage depots in fluid communication with a microfluidic path device into a ligation reactor of the microfluidic path device to create a synthetic circular ligated product by joining the synthetic gene of interest with the synthetic in vitro transcription facilitator cassette; pneumatically introducing one or more exonuclease agents from one or more storage depots of the plurality of storage depots into the ligation reactor to remove unreacted material by removing unreacted synthetic gene of interest and unreacted synthetic in vitro transcription facilitator cassette away from the synthetic circular ligated product; pneumatically delivering the synthetic circular ligated product into a multiple displacement amplification (MDA) reactor of the microfluidic path device to combine with one or more amplification agents for amplifying the circular ligated product to generate branched or circular amplified DNA; and pneumatically transferring the branched amplified DNA ligated product to a digestion reactor of the microfluidic path device to generate double stranded DNA template by linearizing the branched amplified DNA ligated product, wherein the ligation reactor, MDA reactor and digestion reactor and plurality of storage depots form a closed-path and sealed environment.

A method of making a synthetic double stranded DNA template for an mRNA treatment nanoparticle composition (using a closed-path system comprising a plurality of storage depots configured to be secured in sealed fluid communication with one or more microfluidic path devices) may include: transporting reagents between one or more storage depots of the plurality of storage depots and a plurality of reactors on the one or more microfluidic devices in a closed fluidic path that is protected from atmospheric contact to, in the one or more microfluidic path devices: form a template for in vitro transcription of a therapeutic mRNA.

In general, the methods and apparatuses described herein may produce double stranded DNA template that may be free of bacterial DNA and/or free of endotoxin. The template generation methods and apparatuses described herein may not involve bacterial culture. In addition, the therapeutic mRNA manufactured as described herein may be synthesized from the template without the use of bacterial polynucleotides. Thus, any of the methods described herein may be methods for producing therapeutic mRNA without the use of bacterial DNA, and/or isolated from endotoxin. In particular, described herein are methods of manufacturing double stranded DNA template that is free of bacterial DNA and/or endotoxin. Any of the methods described herein may be aseptic manufacturing methods.

Any of these methods may include digesting the synthetic in vitro transcription facilitator cassette with a type IIS restriction enzyme. Joining may include ligating with a DNA ligase. Removing may comprise digesting linear DNA with an exonuclease. The exonuclease may comprise exonuclease V. Amplifying may comprise multiple displacement amplification (MDA). Amplifying may comprise amplifying with Φ29 DNA polymerase. Amplifying may comprise generating branched amplified DNA.

Linearizing may comprise digesting with a type IIs restriction enzyme. Linearizing may comprise digesting with a BsaI restriction enzyme. The synthetic gene of interest may be linear. In some variations, the synthetic in vitro transcription facilitator cassette comprises double stranded DNA template comprising a promoter; a 5' UTR; a cleavable linker; a 3' UTR; and a portion encoding a polyA region comprising at least about 200 adenine residues or about 200 thymidine residues in a row. The portion encoding the polyA region may be at least about 300 bps long. In some variations, the portion encoding polyA region may be at least about 350 bps long.

The synthetic gene of interest may comprise at least part of a T-cell receptor. The synthetic gene of interest may comprise a Complementary Determining Region (CDR).

The in vitro transcription facilitator cassette may be less than 2 kb in length. The in vitro transcription facilitator cassette maybe less than 1 kb in length. The in vitro transcription facilitator cassette may be less than about 700 base pairs in length. The synthetic in vitro transcription facilitator cassette may not encode an antibiotic resistance gene.

The synthetic circular ligated product may not have an origin of replication (ORI). The in vitro transcription facilitator cassette may not have an origin of replication (ORI).

As mentioned, the processes of any of the methods described herein may be performed in a closed-path microfluidic path device and/or within a closed system. The processes may be performed in a closed-path microfluidic path device and the joining step may be performed in a different module (e.g., a different microfluidic path device) from the amplifying step and the amplifying step is performed in a different module from the linearizing step.

Any of these methods may include purifying, in the closed path of the one or more microfluidic path devices, the template.

Also described herein are methods of performing in vitro transcription using the closed-path method and apparatuses described herein. For example, a method of performing an in vitro transcription (IVT) reaction using a closed-path system (e.g., comprising a plurality of storage depots configured to be secured in sealed fluid communication with one or more microfluidic path devices) may include: transporting reagents between one or more storage depots of the plurality of storage depots and a plurality of reactors on the one or more microfluidic devices in a closed fluidic path that is protected from atmospheric contact to perform in vitro transcription of a therapeutic mRNA from a template in the one or more microfluidic path devices.

A method of performing an in vitro transcription (IVT) reaction may include: automatically delivering a DNA template through directed fluid flow, a polymerase, and nucleotides into a first reactor of a microfluidic path device from a plurality of storage depots in amounts metered with sub-microliter precision; processing the template material and nucleotides in the first reactor to form a therapeutic mRNA; and pneumatically transferring the therapeutic mRNA through the microfluidic path device away from the first reactor, wherein the first microfluidic path device and the plurality of storage depots form a closed-path and sealed environment to prevent atmospheric exposure.

The closed-path system may operate automatically and continuously. The closed-path system may pneumatically control the performance of the in vitro transcription of the therapeutic mRNA from the template.

Any of these methods may also include purifying the therapeutic mRNA in the one or more microfluidic devices. Transporting reagents may comprise transporting the reagents to a first reactor of the microfluidic path device from the plurality of storage depots.

Also described herein are methods of formulating (e.g., combining with delivery vehicle) a therapeutic mRNA. For example, a method of manufacturing an mRNA treatment nanoparticle composition (e.g., using a closed-path system comprising a plurality of storage depots configured to be secured in sealed fluid communication with one or more microfluidic path devices) may include: transporting reagents between one or more storage depots of the plurality of storage depots and a plurality of reactors on the one or more microfluidic devices in a closed fluidic path that is protected from atmospheric contact to formulate the mRNA treatment nanoparticle composition by combining a therapeutic mRNA with a delivery vehicle in the one or more microfluidic path devices. The closed-path system may automatically and continuously combine the mRNA with a delivery vehicle. The closed-path system may pneumatically control combining the mRNA with a delivery vehicle. For example, the closed-path system may pneumatically control combining the mRNA with a delivery vehicle by deflecting one or more membranes within the one or more microfluidic path devices.

Combining the mRNA with a delivery vehicle may further comprise dialyzing the mRNA treatment nanoparticle composition in the one or more microfluidic path devices to purify the mRNA treatment nanoparticle composition, and/or concentrating the mRNA treatment nanoparticle composition on the one or more microfluidic path devices.

For example, described herein are methods of manufacturing an mRNA using a system comprising a plurality of storage depots configured to be secured in sealed fluid communication with one or more microfluidic path devices. Any of these methods may include: transporting reagents between one or more storage depots of the plurality of storage depots and a plurality of reactors on the one or more microfluidic devices in a closed fluidic path that is protected from atmospheric contact to perform, in the one or more microfluidic path devices, one or more of the processes of: forming a template, performing in vitro transcription of mRNA from the template, and purifying the mRNA.

A method of manufacturing an therapeutic mRNA composition using a system comprising a plurality of storage depots configured to be secured in sealed fluid communication with one or more microfluidic path devices may include: transporting reagents between one or more storage depots of the plurality of storage depots and a plurality of reactors on the one or more microfluidic devices in a closed fluidic path that is protected from atmospheric contact to perform, in the one or more microfluidic path devices, one or more of the processes of: forming a template, performing in vitro transcription of therapeutic mRNA from the template, purifying the therapeutic mRNA, and formulating the mRNA with a delivery vehicle.

A method of manufacturing an therapeutic mRNA composition using a system comprising a plurality of storage depots configured to be secured in sealed fluid communication with one or more microfluidic path devices may include: transporting reagents between one or more storage depots of the plurality of storage depots and a plurality of reactors on the one or more microfluidic devices in a closed fluidic path that is protected from atmospheric contact to perform, in the one or more microfluidic path devices, one or more of the processes of: forming a template, performing in vitro transcription of therapeutic mRNA from the template, purifying the therapeutic mRNA, formulating the mRNA with a delivery vehicle, and performing dialysis and concentration of the formulated therapeutic mRNA.

A method of manufacturing an therapeutic mRNA composition using a system comprising a plurality of storage depots configured to be secured in sealed fluid communication with one or more microfluidic path devices may include: following a sequence of processes for forming the therapeutic mRNA composition that are encoded in a non-transitory, computer-readable medium, wherein the processes include: transporting reagents between one or more storage depots of the plurality of storage depots and a plurality of reactors on the one or more microfluidic devices in a closed fluidic path that is protected from atmospheric contact to perform, in the one or more microfluidic path devices, one or more of the processes of: forming a template, performing in vitro transcription of therapeutic mRNA from the template, purifying the therapeutic mRNA, and combining the mRNA with a delivery vehicle.

Also described herein are methods of manufacturing an therapeutic mRNA composition using a system comprising a plurality of storage depots configured to be secured in sealed fluid communication with a microfluidic path device, the method comprising performing in vitro transcription of therapeutic mRNA from a template on the microfluidic path device, and purifying the therapeutic mRNA in one or more fluidically connected reactors on the microfluidic path device.

Also described herein are therapeutics made by any of these methods, including in particular, mRNA therapies. For example, described herein are therapeutic mRNAs made using a system comprising a plurality of storage depots configured to be secured in sealed fluid communication with one or more microfluidic path devices, the mRNA made by: transporting reagents between one or more storage depots of the plurality of storage depots and a plurality of reactors on the one or more microfluidic devices in a closed fluidic path that is protected from atmospheric contact to perform, in the one or more microfluidic path devices, one or more of the processes of: forming a template, performing in vitro transcription of mRNA from the template, and purifying the mRNA.

For example, described herein are therapeutic mRNAs made using a system comprising a plurality of storage depots configured to be secured in sealed fluid communication with one or more microfluidic path devices, the mRNA made by: transporting reagents between one or more storage depots of the plurality of storage depots and a plurality of reactors on the one or more microfluidic devices in a closed fluidic path that is protected from atmospheric contact to perform, in the one or more microfluidic path devices, one or more of the processes of: forming a template, performing in vitro transcription of therapeutic mRNA from the template, purifying the therapeutic mRNA, and formulating the mRNA with a delivery vehicle.

For example, described herein are therapeutic mRNAs made using a system comprising a plurality of storage depots configured to be secured in sealed fluid communication with one or more microfluidic path devices, the mRNA made by::transporting reagents between one or more storage depots of the plurality of storage depots and a plurality of reactors on the one or more microfluidic devices in a closed fluidic path that is protected from atmospheric contact to perform, in the one or more microfluidic path devices, one or more of the processes of: forming a template, performing in vitro transcription of therapeutic mRNA from the template, purifying the therapeutic mRNA, formulating the mRNA with a delivery vehicle, and performing dialysis and concentration of the formulated therapeutic mRNA.

Described herein are therapeutic mRNA compositions formed using a system comprising a plurality of storage depots configured to be secured in sealed fluid communication with one or more microfluidic path devices, by: following a sequence of processes for forming the therapeutic mRNA composition that are encoded in a non-transitory, computer-readable medium, wherein the processes include: transporting reagents between one or more storage depots of the plurality of storage depots and a plurality of reactors on the one or more microfluidic devices in a closed fluidic path that is protected from atmospheric contact to perform, in the one or more microfluidic path devices, one or more of the processes of: forming a template, performing in vitro transcription of therapeutic mRNA from the template, purifying the therapeutic mRNA, and combining the mRNA with a delivery vehicle. For example, a therapeutic mRNA may be a therapeutic mRNA composition formed using a system comprising a plurality of storage depots configured to be secured in sealed fluid communication with a microfluidic path device, the method comprising performing in vitro transcription of therapeutic mRNA from a template on the microfluidic path device, and purifying the therapeutic mRNA in one or more fluidically connected reactors on the microfluidic path device.

Any of the systems described herein may include controller configured to perform any of these methods. Thus, also described herein is software, firmware or hardware configured to perform any of the methods described herein. For example, described herein are non-transitory computer readable medium embodying instructions for manufacturing an mRNA, that when executed by a controller of a system comprising a plurality of storage depots configured to be secured in sealed fluid communication with one or more microfluidic path devices, cause the controller to perform the method of: transporting reagents between one or more storage depots of the plurality of storage depots and a plurality of reactors on the one or more microfluidic devices in a closed fluidic path that is protected from atmospheric contact to perform, in the one or more microfluidic path devices, one or more of the processes of: forming a template, performing in vitro transcription of mRNA from the template, and purifying the mRNA.

For example, described herein are non-transitory computer readable medium embodying instructions for manufacturing an mRNA, including a therapeutic mRNA composition, that when executed by a controller of a system comprising a plurality of storage depots configured to be secured in sealed fluid communication with one or more microfluidic path devices, cause the controller to perform any of the methods described herein.

Also described herein are methods of making a synthetic double stranded DNA template for an mRNA using a closed-path system comprising a plurality of storage depots configured to be secured in sealed fluid communication with one or more microfluidic path devices, that may include: transporting reagents between one or more storage depots of the plurality of storage depots and a plurality of reactors on the one or more microfluidic devices in a closed fluidic path that is protected from atmospheric contact to combine the reagents; and forming a template for in vitro transcription of a therapeutic mRNA.

For example, a method of making a synthetic double stranded DNA template for use as the input into an mRNA in vitro transcription reaction using a closed-path system may include a plurality of storage depots configured to be secured in sealed fluid communication with one or more microfluidic path devices, the method comprising: transporting reagents between one or more storage depots of the plurality of storage depots and a plurality of reactors on the one or more microfluidic devices in a closed fluidic path that is protected from atmospheric contact; and forming a template for in vitro transcription of a therapeutic mRNA.

A method of manufacturing an mRNA composition using a system comprising a plurality of storage depots configured to be secured in sealed fluid communication with one or more microfluidic path devices, wherein the one or more microfluidic path devices comprise a plurality of reactors, may include: delivering a template precursor material from one or more storage depots to a first reactor region of the plurality of reactors and processing the template precursor material to prepare a template from the template precursor material; transferring the template to a second reactor region of the plurality of reactors and processing the template by in vitro transcription to form an mRNA; and transferring the mRNA to a third reactor region of the plurality of reactors and processing the mRNA to combine it with a delivery vehicle to form the mRNA composition, wherein materials including the template material and delivery vehicle are delivered from the storage depots into the plurality of reactors without atmospheric contact.

A method of manufacturing an mRNA composition using a system comprising a plurality of storage depots in sealed fluid communication with one or more microfluidic path devices, wherein the one or more microfluidic path devices comprise a plurality of reactors, may include: pneumatically delivering a template precursor material from one or more storage depots to a first reactor region of the plurality of reactors and processing the template precursor material to prepare a template from the template precursor material; pneumatically transferring the template to a second reactor region of the plurality of reactors and processing the template by in vitro transcription to form mRNA; pneumatically transferring the mRNA to a third reactor region of the plurality of reactors and processing the mRNA to combine it with delivery vehicle to form the therapeutic mRNA composition; and transferring the mRNA product to one or more storage depots, wherein the materials are delivered from the storage depots into the reactors of the microfluidic path device with sub-microliter precision and without atmospheric contact.

A method of making a synthetic double stranded DNA template for in vitro transcription using a closed-path system comprising a plurality of storage depots in sealed fluid communication with a microfluidic path device, may include: joining a synthetic gene of interest with a synthetic in vitro transcription facilitator cassette to create a synthetic circular ligated product; removing unreacted synthetic gene of interest and unreacted synthetic in vitro transcription facilitator cassette away from the synthetic circular ligated product; amplifying the circular ligated product to generate branched or circular amplified DNA; and linearizing the branched amplified DNA ligated product to generate double stranded DNA template, wherein each of the joining, removing, amplifying and linearizing processes are performed in the microfluidic path device by the closed-path system.

Any of these methods may be high-efficiency, automated methods, including high-efficiency, automated methods of making a synthetic double stranded DNA template for in vitro transcription. For example, a method may include: pneumatically delivering each of: a synthetic gene of interest and a synthetic in vitro transcription facilitator cassette from one or more storage depots of a plurality of storage depots in fluid communication with a microfluidic path device into a ligation reactor of the microfluidic path device to create a synthetic circular ligated product by joining the synthetic gene of interest with the synthetic in vitro transcription facilitator cassette; pneumatically introducing one or more exonuclease agents from one or more storage depots of the plurality of storage depots into the ligation reactor to remove unreacted material by removing unreacted synthetic gene of interest and unreacted synthetic in vitro transcription facilitator cassette away from the synthetic circular ligated product; pneumatically delivering the synthetic circular ligated product into a multiple displacement amplification (MDA) reactor of the microfluidic path device to combine with one or more amplification agents for amplifying the circular ligated product to generate branched or circular amplified DNA; and pneumatically transferring the branched amplified DNA ligated product to a digestion reactor of the microfluidic path device to generate double stranded DNA template by linearizing the branched amplified DNA ligated product, wherein the ligation reactor, MDA reactor and digestion reactor and plurality of storage depots form a closed-path and sealed environment.

A method of making a synthetic double stranded DNA template for in vitro transcription, the method comprising following a sequence of processes that are encoded in a non-transitory, computer-readable medium, may include: delivering each of: a synthetic gene of interest and a synthetic in vitro transcription facilitator cassette from one or more storage depots of a plurality of storage depots in fluid communication with a microfluidic path device into a ligation reactor of the microfluidic path device to create a synthetic circular ligated product by joining the synthetic gene of interest with the synthetic in vitro transcription facilitator cassette; introducing one or more exonuclease agents from one or more storage depots of the plurality of storage depots into the ligation reactor to remove unreacted material by removing unreacted synthetic gene of interest and unreacted synthetic in vitro transcription facilitator cassette away from the synthetic circular ligated product; delivering the synthetic circular ligated product into a multiple displacement amplification (MDA) reactor of the microfluidic path device to combine with one or more amplification agents for amplifying the circular ligated product to generate branched or circular amplified DNA; and transferring the branched amplified DNA ligated product to a digestion reactor of the microfluidic path device to generate double stranded DNA template by linearizing the branched amplified DNA ligated product, wherein the ligation reactor, MDA reactor and digestion reactor and plurality of storage depots form a closed-path and sealed environment.

A method of performing an in vitro transcription (IVT) reaction using a system comprising a plurality of storage depots configured to be secured in sealed fluid communication with one or more microfluidic path devices, may include: transporting reagents between one or more storage depots of the plurality of storage depots and a plurality of reactors on the one or more microfluidic devices in a closed fluidic path that is protected from atmospheric contact to perform in vitro transcription of a therapeutic mRNA from a template in the one or more microfluidic path devices.

Also described herein are methods of performing an in vitro transcription (IVT) reaction, the method comprising following a sequence of processes that are encoded in a non-transitory, computer-readable medium, wherein the processes include: pneumatically delivering a template material, a polymerase, and nucleotides into a first reactor of a microfluidic path device from a plurality of storage depots in amounts metered with sub-microliter precision at any time during the reaction; processing the template material and nucleotides in the first reactor to form a therapeutic mRNA; and pneumatically transferring the therapeutic mRNA through the microfluidic path device away from the first reactor, wherein the first microfluidic path device and the plurality of storage depots form a closed-path and sealed environment to prevent atmospheric exposure.

Also described herein are methods of performing an in vitro transcription (IVT) reaction, the method comprising following a sequence of processes that are encoded in a non-transitory, computer-readable medium, wherein the processes include: delivering, by induced fluidic flow, a template material, a polymerase, and nucleotides into a microfluidic path device from a plurality of storage depots in amounts controlled by a controller following the sequence of processes; processing the template material and nucleotides in one or more reactors to form a therapeutic mRNA; and transferring the therapeutic mRNA through the microfluidic path device away from the one or more reactors, wherein the first microfluidic path device and the plurality of storage depots form a closed-path and sealed environment to prevent atmospheric exposure.

Also described herein are methods of performing an in vitro transcription (IVT) reaction, the method comprising: delivering, by induced fluidic flow, a template material, a polymerase, and nucleotides into a microfluidic path device from a plurality of storage depots in amounts controlled by pre-programmed software commands; processing the template material and nucleotides in a first one or more reactors in the microfluidic path device to form a therapeutic mRNA; and transferring the therapeutic mRNA through the microfluidic path device away from the first one or more reactor, into a second one or more reactors adapted for purification of mRNA, wherein the microfluidic path device and the plurality of storage depots form a closed-path and sealed environment to prevent atmospheric exposure.

Also described herein are methods of performing an in vitro transcription (IVT) reaction, the method comprising following a sequence of processes that are encoded in a non-transitory, computer-readable medium, wherein the processes include: delivering, by induced fluidic flow, a template material, a polymerase, and nucleotides into a first one or more reactors of a first microfluidic path device from a plurality of storage depots, in amounts controlled by the sequence of processes; processing the template material and nucleotides in the first one or more reactors to form a therapeutic mRNA; and transferring the therapeutic mRNA through the first microfluidic path device away from the first one or more reactors, into a second one or more reactor adapted for purification of mRNA; and transferring thus purified mRNA for completion of the formulation of the mRNA treatment nanoparticle, wherein the first microfluidic path device and the plurality of storage depots form a closed-path and sealed environment to prevent atmospheric exposure.

Also described herein are methods of performing an in vitro transcription (IVT) reaction, the method comprising following a sequence of processes that are encoded in a non-transitory, computer-readable medium, wherein the processes include: pneumatically delivering a template material, a polymerase, and nucleotides into a first one or more reactors of a first microfluidic path device from a plurality of storage depots; processing the template material and nucleotides in the first one or more reactors to form a therapeutic mRNA; and transferring the therapeutic mRNA through the first microfluidic path device away from the first one or more reactors, into a second one or more reactors adapted for purification of mRNA; and transferring purified mRNA to a third one or more reactors to combine the purified mRNA with one or more delivery vehicles to form an mRNA treatment nanoparticle, wherein the first microfluidic path device and the plurality of storage depots form a closed-path and sealed environment to prevent atmospheric exposure.

For example, also described herein are methods of performing an in vitro transcription (IVT) reaction, the method comprising following a sequence of processes that are encoded in a non-transitory, computer-readable medium, wherein the processes include: pneumatically delivering a template material, a polymerase, and nucleotides into a first one or more reactors of a first microfluidic path device from a plurality of storage depots; processing the template material and nucleotides in the first one or more reactors to form a therapeutic mRNA; and transferring the therapeutic mRNA through the first microfluidic path device away from the first one or more reactors, into a second one or more reactors comprising cellulose and adapted for purification of mRNA; and transferring purified mRNA to a third one or more reactors to combine the purified mRNA with one or more delivery vehicles to form an mRNA treatment nanoparticle, wherein the first microfluidic path device and the plurality of storage depots form a closed-path and sealed environment to prevent atmospheric exposure.

Also described herein are methods of manufacturing an therapeutic mRNA composition using a system comprising a plurality of storage depots configured to be secured in sealed fluid communication with one or more microfluidic path devices, the method comprising: transporting reagents between one or more storage depots of the plurality of storage depots and a plurality of reactors on the one or more microfluidic devices in a closed fluidic path that is protected from atmospheric contact to formulate the therapeutic mRNA composition by combining one or more therapeutic mRNAs with a delivery vehicle in the one or more microfluidic path devices.

A method of manufacturing an therapeutic mRNA composition on demand using a system comprising a plurality of storage depots configured to be secured in sealed fluid communication with one or more microfluidic path devices, may include: transporting reagents between one or more storage depots of the plurality of storage depots and a plurality of reactors on the one or more microfluidic devices in a closed fluidic path that is protected from atmospheric contact to perform, in the one or more microfluidic path devices, one or more of the processes of: forming a template, performing in vitro transcription of therapeutic mRNA from the template, purifying the therapeutic mRNA, and formulating the mRNA with a delivery vehicle.

Any of these methods and apparatuses may be operated (e.g., the therapeutic mRNA is manufactured) at the site of care. Any of these methods and apparatuses may be performed rapidly and continuously, e.g., the therapeutic is manufactured in less than 72 hours.

For example, described herein are methods and apparatuses for manufacturing mRNA therapies that may include the use of fully automated, software-controlled microfluidics. These methods and apparatuses may be used for personalized or individualized therapies. Also described herein are apparatuses (e.g., systems, devices, etc.) and methods that include software control of any of the manufacturing processes described herein, including forming the template, in vitro transcription, purification of the therapeutic mRNA, concentration of the mRNA, and compounding of the mRNA(s) with one or more delivery vehicle. The software control may allow these methods to be automated so that any, some or all of these processes for manufacturing one or more therapeutic mRNA may be performed rapidly with accuracy and precision. Software control and micro-fluidic precise delivery and transfer of reaction constituents offer the opportunity to increase process control, efficiency and reproducibility whilst substantially reducing or eliminating manual manipulations, reducing facility needs and shortening production cycle times, ultimately leading to lower cost therapies produced just-in-time, if appropriate.

In some of the apparatuses (e.g., systems, devices, etc.) described herein, each batch of therapeutic material may be produced in dedicated, single-use, disposable microfluidic path devices (also referred to herein as biochips), that may be housed inside a microfluidic path device control system (also referred to herein as a control system). The entire production may proceed as a sterile-by-design, closed-path process without contact with the atmosphere. All the production processes may be automated, controlled by the control system to achieve a copy-exact process, regardless of the attributes of the facility housing the system. The production parameters, raw materials and environment data (including a full visual record) may become a part of an extensive, encrypted electronic file secured in the cloud and associated with each production run. In addition, purification processes, as well as a number of QC assays may be performed in-line during the production process in a single fluid flow, allowing anomalies to be detected at an early stage, through process control concepts developed in the semi-conductor industry. By harnessing a fully automated, software-controlled approach to manufacturing, personalized and individualized mRNA therapies may be manufactured in a cost-effective manner for the benefit of the patients.

In particular these methods and apparatuses may produce mRNA therapies synthetically outside of the human body through a synthesis technology known as in vitro transcription (IVT). In some examples, naked mRNA molecules are large, polyanionic molecules that do not cross the cell membrane, and are rapidly degraded by extracellular nucleases in vivo. The methods and apparatuses described herein may produce formulations of mRNA molecules with one or more delivery vehicles, designed to transport the mRNA to a target (tissue, body, region of tissue, etc.). For example, in some variations the delivery vehicle may be a lipid-containing amphipathic delivery vehicle that provides packaging and protection of mRNA cargos during circulation, avoid immune recognition, and may facilitate cellular uptake and release.

In general, as will be described in greater detail herein, in some variations all or some of the production processes, including template synthesis, IVT, purification, and formulation with delivery vehicles, may be performed in the highly controlled environment of one or more microfluidic path devices, allowing for the optimization of a robust, high-quality and highly reproducible manufacturing process.

Therapies such as mRNA therapies may be used for mRNA vaccination. In addition to their high potency, mRNA therapies also have important advantages related to their rapid development cycle, standardized manufacturing, transient expression and low risk of genomic integration.

In some variations, the mRNA therapies described herein may include as an active ingredient in the final drug product an mRNA that encodes an antigen or protein of interest. Robust translation of mRNA requires a functional 5' cap structure. A 5' cap (or 7-methylguanosine cap) consists of a terminal 7-methylguanosine residue that is linked through a 5'-5'-triphosphate bond to the first transcribed nucleotide. Its presence is critical for recognition of the mRNA by the ribosome and protection from RNAses. The poly(A) tail regulates mRNA stability and translational initiation synergistically with the m7G cap by binding the poly(A) binding protein (PABP), which interacts with eukaryotic translation initiation factor eIF4G, and in turn forms a complex with eIF4E. The length of the poly(A) tail may influence the efficiency of the mRNA to protein translation process.

The methods and apparatuses described herein may formulate the mRNA treatment nanoparticle to provide packaging and protection of mRNA cargos during circulation, avoid immune recognition, localize drug product in desired tissues, and facilitate cellular uptake and release, while avoiding toxicity or immunogenicity concerns which could limit repeated dosing.

In general, a method of manufacturing an mRNA treatment nanoparticle (including, but not limited to a patient-specific T-cell lymphoma vaccine drug product) may include identification of a target protein and design of the mRNA sequence, preparation a double stranded DNA template as for the target sequence. This sequence may be used to generate the mRNA for the in vitro transcription (IVT) reaction, to synthesize mRNA. This therapeutic mRNA may then be purified to remove process impurities and filtration to generate the drug substance. The therapeutic mRNA may then be formulated with the delivery vehicle (including in some variation with adjuvant and delivery vehicle components to form amphipathic nanoparticle). The formulation may then be processed and purified to generate drug product that may be used for delivery to the patient.

As a specific example of one variation, an exemplary process for manufacturing a patient-specific T-cell lymphoma vaccine drug product may include identification of a clonally expanded TCR sequence (idiotype) expressed by the lymphoma cells. The process may also include designing the mRNA vaccine sequence, and preparing a double stranded DNA template for the IVT reaction. The template may be used for the IVT reaction to synthesize mRNA, and this therapeutic mRNA may be purified to remove process impurities and filtration prepare the therapeutic mRNA as the drug substance. The therapeutic mRNA may then be formulated with an immunomodulator and delivery vehicle components to form amphipathic nanoparticles. Post-formulation processing may then be performed to generate drug product, such as a therapeutic mRNA treatment nanoparticle.

Any of these manufacturing processes may be optimized to be performed using an automated microfluidic path device control system as described herein. For example, a DNA template production may take place in one or more microfluidic path devices; a template microfluidic path device (e.g., template biochip) may be used. In this example, the processes of in-vitro transcription of the mRNA and the purification of that material to generate the drug substance may be performed on an IVT microfluidic path device (e.g., an IVT biochip), and drug product formulation processes may be done on a formulation microfluidic path device (e.g., formulations biochip). These microfluidic path devices may contain the input ports, metering valves, reaction chambers, and purification structures required to perform each process in the manufacturing process.

Apparatus

Figure 34A:
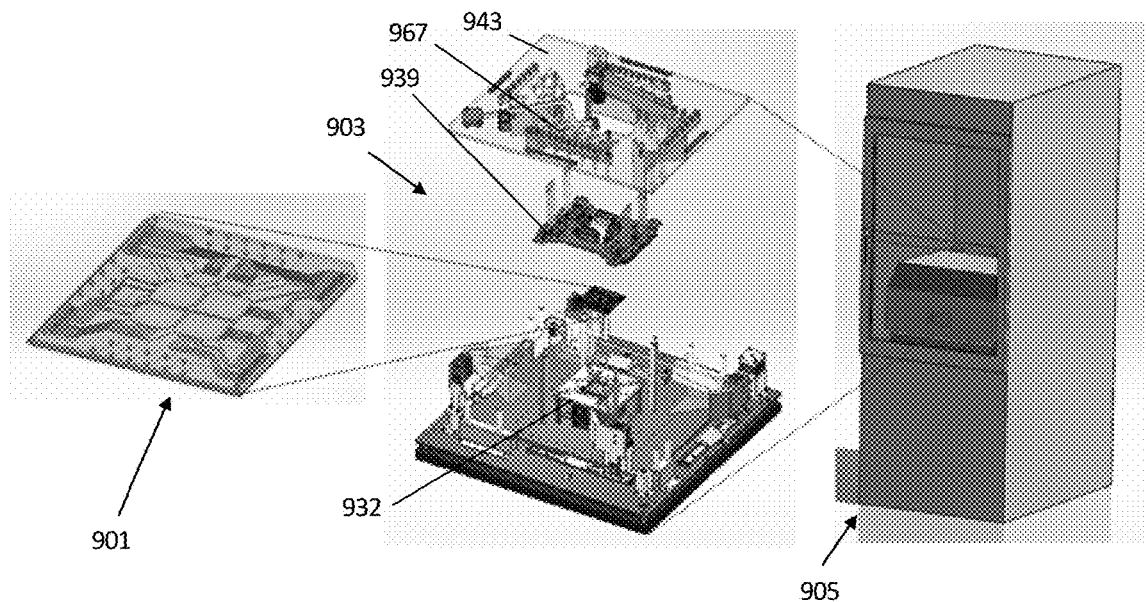
FIG. 34A illustrates one example of a microfluidic path device control system as described herein.

The methods described herein may generally be performed using an apparatus that may include one or more microfluidic path devices (e.g., biochips), and a microfluidic path device control system that is configured to control operations in the microfluidic path device. These microfluidic path devices may be placed and held within the microfluidic path device control system (which may be referred to herein as a manufacturing system), which may operate in a closed path manner that prevents exposure of the component parts of some, or more preferably nearly all or all of the manufacturing components to the atmosphere. FIG. 34A shows one example of a microfluidic path device control system 903, which may also be referred to as a microfluidic path device management system, and may include: hardware for holding the microfluidic path device, applying positive/negative pressure to operate microfluidic operations in the microfluidic path device, heating/cooling all or regions of the microfluidic path device, detecting one or more features from the microfluidic path device and/or recording operations performed on the one or more microfluidic path device. The microfluidic path device control system may also include one or more processors (e.g., a controller, not shown), and a temperature-controlled (e.g., refrigerated) container 905 (e.g., an ISO class 5 cabinet). This system may be used or may include one or more microfluidic path devices 901. The microfluidic path device control system may include a seating mount 932 to releasably hold one or more microfluidic path devices (e.g., cartridge) 901. The microfluidic path device control system may also include a thermal controller for cooling/heating the microfluidic path device when seated, which may be under or coupled with the seating mount. A fluid interface assembly 939 may be lifted off (up and/or to the side) of the seating mount to allow one or more cartridges to be loaded into the seating mount. The fluid interface assembly may include a plurality of fluid contacts that are configured to be applied onto a microfluidic path device held in the seating mount. The fluid contacts may be biased against the microfluidic path device, e.g., by a spring or the like, to improve the seal against a receiving port on the microfluidic path device. A reagent storage frame 943 may be positioned above or to the side of the seating mount and fluid interface assembly. The reagent storage frame may include a plurality of storage depots 967. The fluid interface assembly may be open in the middle, e.g., the region immediately above the microfluidic path device when seated in the seating mount. This opening may allow for visualization through the microfluidic path device for monitoring and tracking and may also allow for access. In FIG. 34A a plurality of sensors (e.g., cameras) are positioned around the perimeter of the microfluidic path device control system and over the center region, above seating mount, for viewing operation of the microfluidic path device control system when fluid is driven, e.g., using a pressure source (not shown).

Figure 34B:
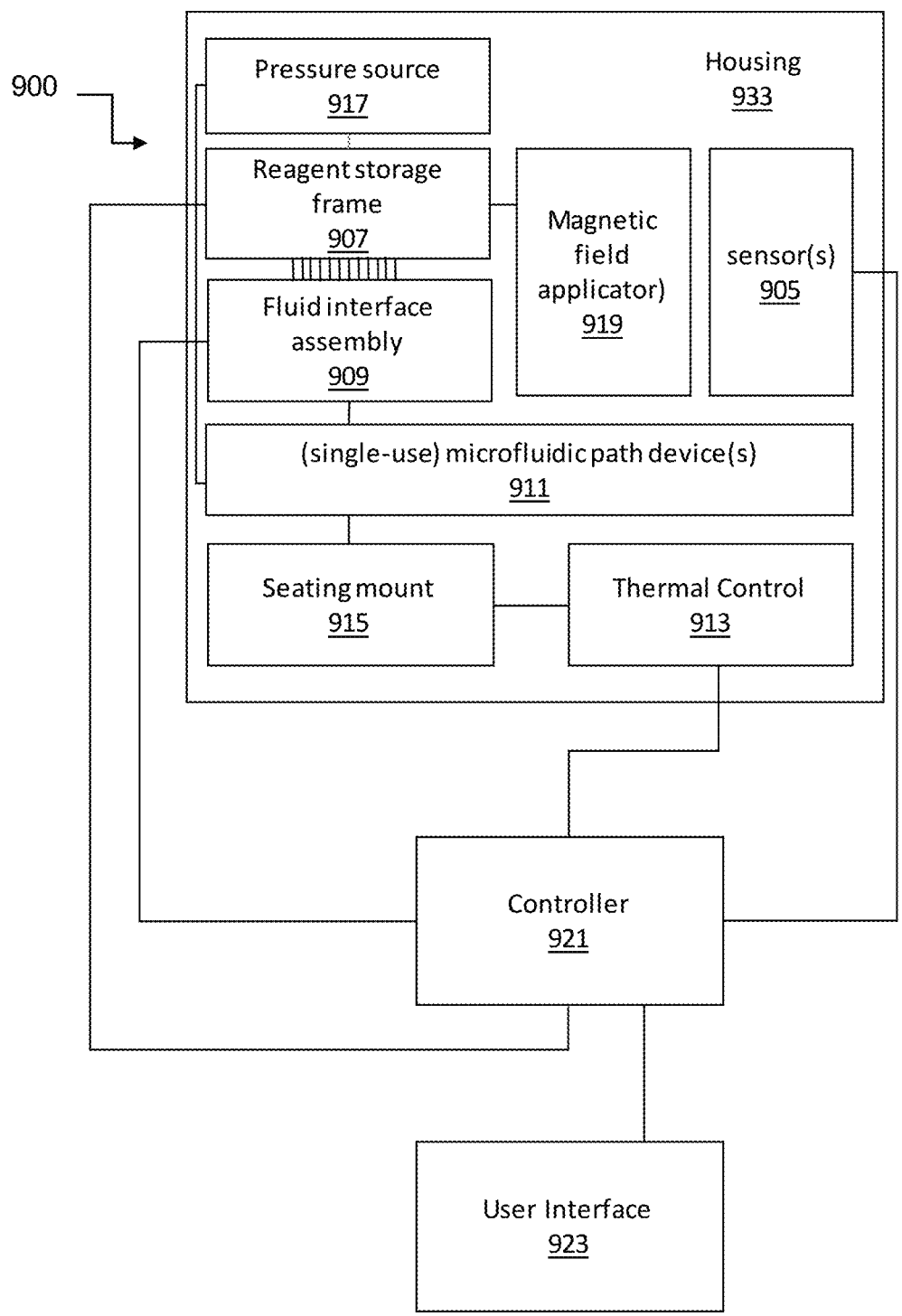
FIG. 34B schematically illustrates an example of a microfluidic path device control system that may be used as described herein.

FIG. 34B is a schematic illustration of one example of a microfluidic path device control system that may be used as described herein. In this example, the apparatus includes a housing 933 enclosing a seating mount 915 which can hold one or more microfluidic path devices 911, which may be single use devices. The housing may be a chamber, enclosure, or the like, which may include a lid or opening; when closed it may be sealed. The housing may enclose a thermal regulator and/or may be configured to be enclosed in a thermally-regulated environment (such as a refrigeration unit, etc.). The housing may form an aseptic barrier. In some variations the housing may form a humidified or humidity-controlled environment.

The seating mount 915 may be configured to secure the microfluidic path device using one or more pins or other components configured to hold the microfluidic path device in a fixed and predefined orientation.

In some variations, a thermal control 913 may be located adjacent to the seating mount 915, to modulate temperature to the one or more microfluidic path devices 911. The thermal control may include a thermoelectric component (e.g. Peltier device) and/or one or more heat sinks for controlling the temperature of all or a portion of the microfluidic path device. In some variations, more than one thermal control may be included, for separately regulating the temperature of one or more regions of the microfluidic path device. The thermal control may include one or more thermal sensors (e.g., thermocouples, etc.) that may be used for feedback control of the microfluidic path device and/or thermal control.

In FIG. 34B, a fluidic interface assembly 909 couples the liquid reagents and/or pressure (e.g., gas) with a microfluidic path device 911 held in the seating mount 915, and may assist in delivery of fluidic materials as well as positive/negative gaseous pressure, from the pressure source 917, to the interior of the microfluidic path device 911. The fluid interface assembly may optionally assist in securing the microfluidic path device(s), as described in greater detail below. The fluid interface assembly may be removable coupled to the apparatus (and may be removed or a portion may be removed) for sterilization between uses.

A reagent storage frame 907 may be configured to contain a plurality of fluid sample holders, each of which may hold a fluid vial configured to hold a reagent (e.g., nucleotides, solvent, water, etc.) for delivery to the microfluidic device 911 or, alternatively, a fluid vial may be configured to receive a product from the interior of the microfluidic path device 911. The reagent storage frame may be referred to as a reagent rack. In some variations, the reagent rack includes a plurality of pressure lines and/or a manifold configured to divide one or more pressure sources 917 into a plurality of pressure lines that may be applied to the microfluidic path device an may be independently or collectively (in sub-combinations) controlled. Alternatively, the fluid depots (vials, etc.) may be configured to directly secure and seal against the microfluidic path device(s).

The fluid interface assembly may include a plurality of fluid lines and/or pressure lines and may include a biased (e.g., spring-loaded) holder or tip that individually and independently drives each fluid and/or pressure line to the microfluidic path device when it is held in the seating mount 915 (or, as mentioned, alternatively the device may directly be spring-mounted). The microfluidic path may be held and secured within the control system, so that the microfluidic path device makes a stable connected to the other components (e.g., tubing). The tubing, e.g., the fluid lines and/or the pressure lines, may be part of the fluid interface assembly and or may connect to the fluid interface assembly. In some variations the fluid lines comprise a flexible tubing that connects between the reagent storage frame, via a connector that couples the vial to the tubing in a locking engagement (e.g., ferrule) and the microfluidic path device. The ends of the fluid paths, in some variations the ends of the fluid lines/pressure lines, may be configured to seal against the microfluidic path device, e.g., at a sealing port formed in the microfluidic path device, as described herein. For example, the ends of the fluid lines may cut or formed to be flat (perpendicular in side view). The vials may be pressurized (e.g., >1 atm pressure, such as 2 atm, 3 atm, 5 atm, etc.) to via the connector which may also connect to the pressure source. For example, the fluid vials may be pressurized to between about 6.9 kPa to 138 kPa (e.g., about 34.5 kPa-138 kPa, about 69 kPa, etc.). Negative or positive pressure may be applied; for example, a vacuum (e.g., about −48.2 kPa or 48.2 kPa) may be applied to draw fluids back into the vials (e.g., the depots) at the end of the process. In general, the fluid vials may be driven at lower pressure than the pneumatic valves, which may prevent or reduce leakage. In some variations the difference in pressure between the fluid and pneumatic valves may be about 34.5 kPa (e.g., about 48.3 kPa, 68.9 kPa, 82.7 kPa, 103.4 kPa, 137.9 kPa, etc.), e.g., between about 34.5 kPa-275.7 kPa (e.g., about 34.5 kPa-206.8 kPa, about 34.5 kPa-137.9 kPa, about 48.2 kPa-275.8 kPa, about 48.2 kPa-137.9 kPa, etc.).

Each vial may be coded (e.g., by an identifier that may be read by one or more sensors, as described below). The controller may monitor the fluid level and therefore the amount of each material in the fluid interface assembly.

The apparatus may also include a magnetic field applicator 919, which may be configured to create a magnetic field at a region of the microfluidic path device 911. One or more sensors 905, which may be optical sensors, may be part of the apparatus, and may sense one or more of a barcode, a fluid level within a fluid vial held within the reagent storage frame, and fluidic movement within the microfluidic path device 911 when the device is mounted within the mounting seat 915.

The sensors may make measurements of the process on the device, e.g., by measuring an optical indicator. In some variations visual/optical markers may be used to estimate yield. For example, fluorescence may be used to detect process yield or residual material by tagging with fluorophores. Alternatively or in addition, dynamic light scattering may be used to measure particle size distributions within a portion of the microfluidic path device (e.g., such as a mixing portion). In some variations, the sensor measurements may be done using one or two optical fibers to convey light (e.g., laser light) in and detect an optical signal coming out. An instrument package may be mounted remotely from the device. Such non-contact sensing may be beneficial.

In any of the methods and apparatuses described herein, the sensors (e.g., video sensors) may record all activity on the microfluidic path device (e.g., chip or cartridge). For example, an entire run for synthesizing and/or processing a material (such as a therapeutic RNA) may be recorded by one or more video sensors, including a video sensor that may visualize the microfluidic path device, e.g., from above. Processing on the microfluidics path device may be visually tracked and this record may be retained for later quality control and/or processing. Thus, the video record of the processing may be saved, stored and/or transmitted for subsequent review and/or analysis.

The internal portion of the apparatus, e.g., within the housing 933, may be further configured to be sterilizable. In particular, portions of the apparatus may be removed and individually sterilized. Sterilization may be performed, e.g., by UV irradiation, or any other method of sterilization that may be required to limit contamination or to meet regulatory requirements. The apparatus including the housing may be housed within a High Efficiency Particulate Air (HEPA) filtered environment. The apparatus including the housing may be housed within a temperature controlled enclosure. In addition, the apparatus itself may include one or more regions that are temperature controlled. In any of the apparatuses described herein, the apparatus may include (e.g., within the housing) a temperature controlled region for storing reagents and/or for storing mRNAs (e.g., therapeutic mRNAs), e.g., at a storage temperature (e.g., a temperature between about −10 degrees C. and about 20 degrees C., such as about 10 degrees C., about 4 degrees C., about −10 degrees C., etc.). Any of these apparatuses may include a library of manufactured mRNAs that may be used individually or in combination with one or more additional mRNAs and a delivery vehicle.

As mentioned above, the microfluidic path device controller system may be controlled by controller 921, including to apply pressure through the microfluidic path device 911 to at least drive fluidic movement. The controller may be at least partially, in some instances completely, outside of the housing. The controller may be configured to include user inputs/outputs. For example, the user interface 923 of the system may permit easy operation and direction of the apparatus and microfluidic path device(s).

Any of the apparatuses described herein may include all or some of the components shown in FIG. 34B; not all components may be necessary. In FIG. 34B, only some of the connections between components are shown; additional (or alternative) connections may be used.

A microfluidic path device control system may support all the production activities inside the microfluidic path device such as supply of reagents, fluid control, temperature control, mixing, purification and process monitoring. Manufacturing activities on the microfluidic path device control system may be accessed and controlled through application software.

The microfluidic path devices may be configured to include one or more reactors for the manufacturing processes which are performed to precisely prepare a therapeutic (e.g., a therapeutic mRNA) material. The same microfluidic path device may operate on one or more microfluidic path devices, either in series and/or in parallel, and without interrupting the continuous-path nature of the microfluidic path device control system. For example, when manufacturing a therapeutic material using multiple processing processes performed in multiple reactors using multiple microfluidic path devices, the fluid product(s), including partial products from one microfluidic path device may be transferred to one or more additional microfluidic path device in a closed-path manner by the apparatus, including by moving fluid containing the microfluidic path device product(s) into a storage depot portion of the microfluidic path device control device.

Figures 35A, 35B, 35C:
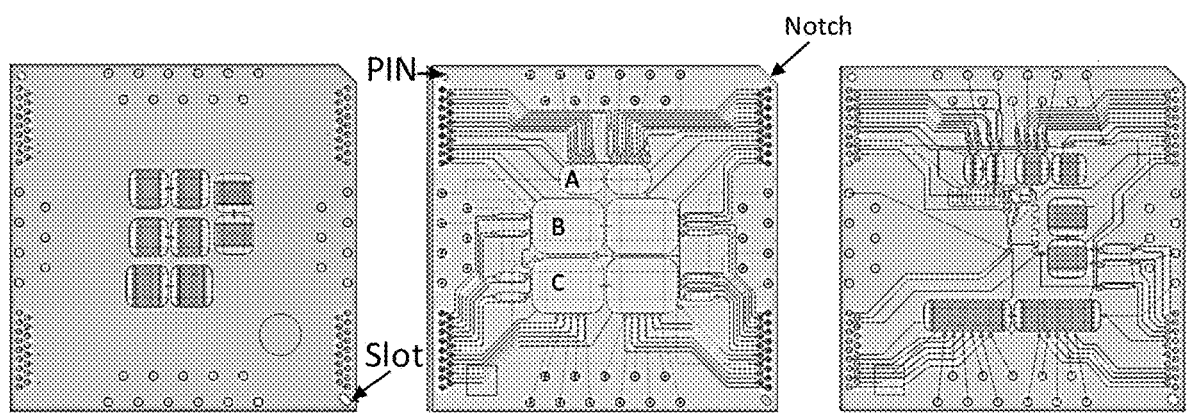
FIGS. 35A-35C illustrate examples of microfluidic path devices as described herein.

Each microfluidic path device may be configured to include one or more reactors for processing during the manufacturing processes. For example, FIGS. 35A-35C illustrate three examples of microfluidic path devices. These examples illustrate three distinct types of microfluidic path device: a template microfluidic path device (FIG. 35A), an in vitro transcription (IVT) microfluidic path device (FIG. 35B) and a formulation microfluidic path device (FIG. 35C). Each of these microfluidic path device examples may be configured to include features to perform a set of unit operations in a controlled and highly reproducible manner.

Figure 35:
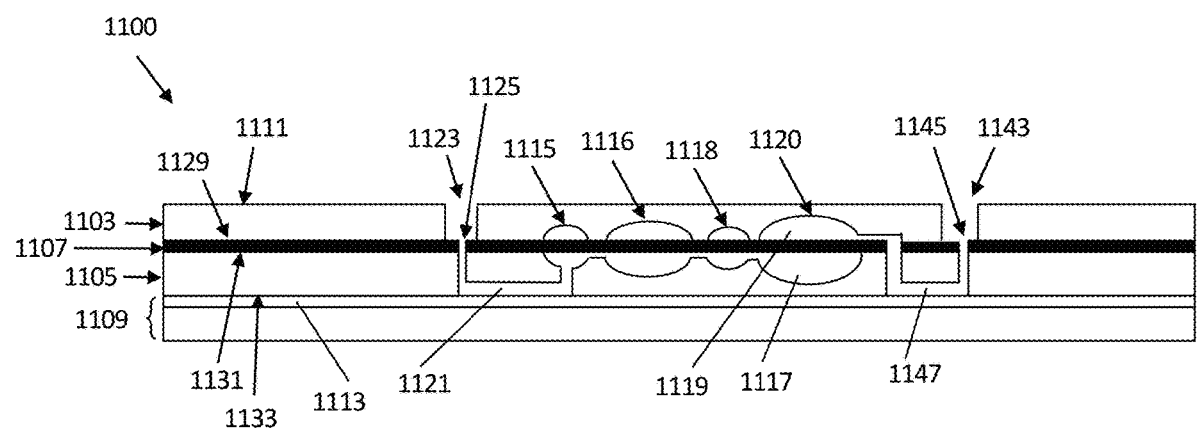
FIG. 35 is a section through a portion of one example of a microfluidic path device as described herein.

In some variations, a microfluidic path device may be configured as multilayered structure composed of two more rigid layers with a flexible membrane sandwiched between the two ridged layers. FIG. 35 illustrates a sectional view (transverse to the plane of the microfluidic path device) through one example of a microfluidic path device having multiple layers that form the reactors for processing the therapeutic as described herein. The reactors may include seals, channels, valves, and chambers, including pumping chambers formed from the multiple layers. For example, a microfluidic path device may be formed of two or more rigid or semi-rigid plates 1103, 1105 and at least one elastic layer 1107. The elastic layer 1107 may be a sheet of elastic material that is liquid-impermeable. The elastic layer maybe somewhat gas permeable, or may be treated to be more or less gas permeable, including in various regions. Although a single continuous sheet of elastic material may be used, in some variations multiple elastic materials sheets may be used, or the 'sheet' may be formed of sections of multiple sheets. The layers and the elastic sheet may be laminated together. In general, chambers for holding, valving and/or pumping fluid may be formed in the plates on either side of the elastic layer so that the elastic layer bisects the chambers into a liquid containing side and a pressure (e.g., gas) applying side. The overall volume of chamber(s) may be constant, and may be formed into both the first (e.g., upper) plate and the second (e.g., lower) plate, but this volume may be divided into the pressure side and the liquid side. By applying positive or negative pressure into the pressure side, the elastic sheet may be deformed to make reduce (down to zero, closing the chamber off) the volume of the liquid containing side or to increase the volume of the liquid containing side (to a predetermined maximum). The pressure applying side of the chamber may be connected, e.g., via a pressure port 1143 in the upper plate 1103 connecting to a pressure channel 1147, for applying negative or positive pressure to the pressure-receiving side 1119 of one or more chambers. The liquid containing side 1117 opposite the pressure-applying side of each chamber may be connected via a fluid channel 1121 to a fluid port 1123. Both the fluid port and the pressure port may be formed by an opening into the upper plate 1103 and the elastic layer 1107, allowing a sealed connection that is isolated from the atmosphere even when there are multiple different input lines as the pressure line is pushed into the elastic layer 1107 that is supported on the underside of the port by the opposite rigid or semi-rigid layer(s), 1105, 1109.

It should be appreciated that all combinations of the foregoing concepts are contemplated as being part of the inventive subject matter disclosed herein and may be employed to achieve the benefits described herein.

Terminology used herein is for the purpose of describing particular examples only and is not intended to be limiting. Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present disclosure.

Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if a value is disclosed, then "less than or equal to" the value, as well as "greater than or equal to" the value is also disclosed. It is also understood that the throughout the application, data are provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

SEQUENCE LISTING

```
Sequence total quantity: 13
SEQ ID NO: 1              moltype = DNA  length = 1401
FEATURE                   Location/Qualifiers
misc_feature              1..1401
                          note = aCTLA4_HC (Heavy chain)- NTX-PMD-059
source                    1..1401
                          mol_type = other DNA
                          organism = synthetic construct
SEQUENCE: 1
atggactgga cctggcggtt cctgtttgtg gtggctgctg ctacaggcgt gcagtctgag   60
gtccagctgc aacagtctgg ccctgtgctt gtgaagcctg gcgcctctgt gaagatgagc  120
tgtaaagcca gcggctacac cttcaccgac tactacatga actgggtcaa gcagagccac  180
ggcaagagcc tggaatggat cggcgtgatc aaccccctaca acggcgacac cagctacaac  240
cagaagttca agggcaaagc cacactgacc gtggacaaga gcagcagcac cgcctacatg  300
gaactgaaca gcctgaccag cgaggacagc gccgtgtact actgcgccag atattacgag  360
agttggttcg cctattgggg ccagggcaca ctggtcaccg tgtccagcgc caagacaaca  420
gcccctagcg tgtaccctct ggctcctgtg tgtggcgata acaggcag ctctgtgacc    480
ctgggctgtc tggtcaaggg ctactttccc gagcctgtga ctctgacctg gaacagcgga  540
tctctgtcta gcggcgtgca cacctttcca gccgttctgc agagcgacct gtacaccctg  600
tccagcagcg tgacagtgac cagcagcaca tggcccagcc agagcatcac ctgtaacgtg  660
gcccatcctg ccagctccac caaggtggac aaaaagatcg agcctagagg ccccaccatc  720
aagccctgtc ctccatgcaa atgccccgct cctaatctgc tcggcggacc cagcgtgttc  780
atcttcccac ctaagatcaa ggacgtgctg atgatctctc tgagccccat cgtgaccgtg  840
gtggtggtgg atgtgtccga ggacgatccc gatgtgcaga tctcttggtt tgtgaacaac  900
gtcgaggtgc acacagccca gacacagacc cacagagagg actacaacag caccctgaga  960
gtggtgtctg ccctgcctat ccagcaccag gattggatga gcggcaaaga attcaagtgt 1020
aaagtgaaca acaaggacct gccggctcct atcgagcgga ccatctctaa gcctaagggc 1080
tctgttagag cccctcaggt gtacgtgctg cctcctccaa aggaagagat gaccaagaca 1140
caagtgaccc tgacatgcat ggtcaccgac ttcatgcccg aggacatcta cgtggaatgg 1200
accaacaacg gcaagaccga gctgaactac aagaacaccg agccagtgct ggactccgac 1260
ggcagctact tcatgtacag caagctgcgc gtggaaaaga gaattgggt cgagcggaac 1320
agctacagct gcagcgtggt gcacgagggc ctgcacaatc accaccacca agagcttc  1380
agcagaaccc ctggcaagta a                                           1401

SEQ ID NO: 2              moltype = AA  length = 465
FEATURE                   Location/Qualifiers
REGION                    1..465
                          note = aCTLA4_HC (Heavy chain)
source                    1..465
                          mol_type = protein
                          organism = synthetic construct
SEQUENCE: 2
DWTWRFLFVV AAATGVQSEV QLQQSGPVLV KPGASVKMSC KASGYTFTDY YMNWVKQSHG   60
KSLEWIGVIN PYNGDTSYNQ KFKGKATLTV DKSSSTAYME LNSLTSEDSA VYYCARYYGS  120
WFAYWGQGTL VTVSSAKTTA PSVYPLAPVC GDTTGSSVTL GCLVKGYFPE PVTLTWNSGS  180
LSSGVHTFPA VLQSDLYTLS SSVTVTSSTW PSQSITCNVA HPASSTKVDK KIEPRGPTIK  240
PCPPCKCPAP NLLGGPSVFI FPPKIKDVLM ISLSPIVTCV VVDVSEDDPD VQISWFVNNV  300
EVHTAQTQTH REDYNSTLRV VSALPIQHQD WMSGKEFKCK VNNKDLPAPI ERTISKPKGS  360
VRAPQVYVLP PPEEEMTKKQ VTLTCMVTDF MPEDIYVEWT NNGKTELNYK NTEPVLDSDG  420
SYFMYSKLRV EKKNWVERNS YSCSVVHEGL HNHHTTKSFS RTPGK                  465

SEQ ID NO: 3              moltype = DNA  length = 741
FEATURE                   Location/Qualifiers
misc_feature              1..741
                          note = aCTLA4_LC (Light chain)- NTX-PMD-045
source                    1..741
                          mol_type = other DNA
                          organism = synthetic construct
SEQUENCE: 3
atggacatga gagtgcccgc tcaactgctg ggactgctgc tgctttggct gagcggagcc   60
agatgcgaca ttcggagagc cgacatcgtg atgacccaga ccacactgag cctgcctgtg  120
tctctgggag atcaggccag catcagctgc agatccagcc agagcatcgt gcacagcaac  180
ggcaacacct acctggaatg gtatctgcag aagcccggac agagcccaa gctgctgatc  240
tacaaggtgt ccaaccggtt cagcggcgtg cccgatagat tttctggcag cggctctggc  300
accgacttca ccctgaagat ctccagagtg gaagccgagg acctgggcgt gtactactgc  360
ttccaaggca gccacgtgcc atacaccttt ggcggcggaa caaagctgga aatcaagcgg  420
gctgatgccg ctcctaccgt gtccatcttt ccacctgca gcgagcagct gacaagcggc  480
ggagctagcg tcgtgtgctt cctgaacaac ttctacccca aggacatcaa cgtgaagtgg  540
aagatcgacg gcagcgagag acagaacggc gtgctgaata ctggaccga ccaggacagc  600
aaggactcca cctacagcat gtccagcaca ctgaccctga ccaaggacga gtacgagcgg  660
cacaacagct acacatgcga ggccacacac aagaccagca agcccatcgt gaagtcc    720
ttcaaccgga acgagtgcta a                                             741

SEQ ID NO: 4              moltype = AA  length = 245
FEATURE                   Location/Qualifiers
REGION                    1..245
                          note = aCTLA4_LC (Light chain)
```

```
source                        1..245
                              mol_type = protein
                              organism = synthetic construct
SEQUENCE: 4
DMRVPAQLLG LLLLWLSGAR CDIRRADIVM TQTTLSLPVS LGDQASISCR SSQSIVHSNG    60
NTYLEWYLQK PGQSPKLLIY KVSNRFSGVP DRFSGSGSGT DFTLKISRVE AEDLGVYYCF   120
QGSHVPYTFG GGTKLEIKRA DAAPTVSIFP PSSEQLTSGG ASVVCFLNNF YPKDINVKWK   180
IDGSERQNGV LNSWTDQDSK DSTYSMSSTL TLTKDEYERH NSYTCEATHK TSTSPIVKSF   240
NRNEC                                                               245

SEQ ID NO: 5                  moltype = DNA  length = 1656
FEATURE                       Location/Qualifiers
misc_feature                  1..1656
                              note = scIL-12 - NTX-PMD-063
source                        1..1656
                              mol_type = other DNA
                              organism = synthetic construct
SEQUENCE: 5
atgtgtcccc agaagctgac catcagttgg ttcgccatcg tgctgctggt gtccccactg     60
atggccatgt gggaactcga aaaggacgtg tacgtggtgg aagtggactg gacccctgat   120
gctcctggcg agacagtgaa cctgacctgc gatacccctg aagaggacga catcacctgg   180
accagcgatc agagacacgg cgtgatcggc tctggcaaga ccctgacaat taccgtgaaa   240
gagttcctgg acgccggcca gtacacctgt cacaaaggcg agagacacct gagccactct   300
catctgctgc tgcacaagaa agagaacggc atctggtcca ccgagatcct gaagaacttc   360
aagaacaaga ccttcctgaa gtgcgaggcc ctaactaca gcggcagatt cacctgtagc     420
tggctggtgc agcggaacat ggacctgaag ttcaacataa agtcctccag cagcagcccg   480
gacagcagag ctgtgacatg tggcatggct agcctgagcg ccgagaaagt gaccctggat   540
cagcgggact acgagaagta cagcgtgtcc tgccaagagg acgtgacctg tcctaccgcc   600
gaggaaaaca tgcctattga gctggccctg aagcccggc agcagaacaa atacgagaac   660
tactccacca gctttttcat ccgggacatc atcaagcccg atcctccaaa gaacctgcag   720
atgaagcctc tgaagaacag ccaggtcgag gtgtcctggg agtaccccga tagctggtct   780
accctcaca gctacttcag cctgaaattc ttcgtgcgga tccagcgcaa gaagaaaag   840
atgaaggaaa ccgaggaagg ctgcaaccag aaagggggcct tcctggtgga aaagaccagc   900
accgaggtgc agtgcaaagg cggcaatgtt tgtgtgcagg cccaggaccg gtactacaac   960
agcagctgta gcaagtgggc ctgcgtgcca tgcagagtca gatctggtgg cggaggatct  1020
ggcggaggtg aagcggcgg aggcggatct agagtgattc ctgtgtctgg ccctgccaga  1080
tgcctgagcc agagcagaaa cctgctgaaa accaccgacg acatggtcaa gaccgccaga  1140
gagaagctga agcactactc ctgcacagcc gaggacatcg accacgagga tatcaccagg  1200
gaccagacaa gcacctgaa aacctgcctg cctctgaaac tgcacaaaaa cgagagctgc  1260
ctggccacca gagagacaag cagcacaaca agaggcagct gtctgcctcc tcagaaaacc  1320
agcctgatga tgacccctgtg cctgggcagc atctacgagg atctgaagat gtaccagacc  1380
gagttccagg ccatcaacgc cgctctgcag aaccacaacc accagcagat catcctggac  1440
aagggcatgc tggtggctat cgacgagctg atgcagagcc tgaaccacaa tggcgaaacc  1500
ctgcggcaga agcctcctgt ggagaggcc gatccttaca gagtgaagat gaagctgtgc  1560
atcctgctgc acgccttcag caccagagtg gtcaccatca acagagtgat gggctacctg  1620
agcagcgcct gagttaatta agctgccttc tgcggg                             1656

SEQ ID NO: 6                  moltype = AA  length = 542
FEATURE                       Location/Qualifiers
REGION                        1..542
                              note = scIL-12 - NTX-PMD-063
source                        1..542
                              mol_type = protein
                              organism = synthetic construct
SEQUENCE: 6
CPQKLTISWF AIVLLVSPLM AMWELEKDVY VVEVDWTPDA PGETVNLTCD TPEEDDITWT    60
SDQRHGVIGS GKTLTITVKE FLDAGQYTCH KGGETLSHSH LLLHKKENGI WSTEILKNFK   120
NKTFLKCEAP NYSGRFTCSW LVQRNMDLKF NIKSSSSSPD SRAVTCGMAS LSAEKVTLDQ   180
RDYEKYSVSC QEDVTCPTAE ETLPIELALE ARQQNKYENY STSFFIRDII KPDPPKNLQM   240
KPLKNSQVEV SWEYPDSWST PHSYFSLKFF VRIQRKKEKM KETEEGCNQK GAFLVEKTST   300
EVQCKGGNVC VQAQDRYYNS SCSKWACVPC RVRSGGGGSG GGGSGGGGSR VIPVSGPARC   360
LSQSRNLLKT TDDMVKTARE KLKHYSCTAE DIDHEDITRD QTSTLKTCLP LELHKNESCL   420
ATRETSSTTR GSCLPPQKTS LMMTLCLGSI YEDLKMYQTE FQAINAALQN HNHQQIILDK   480
GMLVAIDELM QSLNHNGETL RQKPPVGEAD PYRVKMKLCI LLHAFSTRVV TINRVMGYLS   540
SA                                                                  542

SEQ ID NO: 7                  moltype = DNA  length = 1869
FEATURE                       Location/Qualifiers
misc_feature                  1..1869
                              note = TGF_beta_Trap_HC- NTX-PMD-069
source                        1..1869
                              mol_type = other DNA
                              organism = synthetic construct
SEQUENCE: 7
atgtaccgga tgcagctgct gagctgtatc gccctgtctc tggccctggt cacaaactct     60
gaggtccagc tgctggaatc tggcggagga cttgttcagc ctggcggctc tctgagactg   120
tcttgtgctg ccagcggctt caccttcagc agctatatca tgatgtgggt ccgacaggcc   180
cctggcaaag gactggaatg ggtgtccagc atctacccct ggcggcat acattctac   240
gccgacacag tgaagggcag attcaccatc tccagagaca acagcaagaa caccctgtac   300
```

```
ctgcagatga acagcctgag agccgaggac accgccgtgt actactgcgc cagaatcaag    360
ctgggcaccg tgaccacagt ggactactgg ggacagggaa cactggtcac agtgtccagc    420
gcctctacaa agggccctag cgttttccca ctggctccca gcagcaagtc tacaagcgga    480
ggaacagctg ccctgggctg tctggtcaag gactactttc ctgagcctgt gaccgtgtcc    540
tggaacagcg gagcactgac tagcggcgtg cacacatttc cagccgtgct gcaaagcagc    600
ggcctgtact ctctgagcag cgtcgtgaca gtgcctagca gctctctggg cacccagacc    660
tacatctgca atgtgaacca caagcctagc aacaccaagg tggacaagag agtggaaccc    720
aagagctgcg acaagaccca cacctgtcct ccatgtcctg ctccagaact gctcggcgga    780
ccttccgtgt tcctgtttcc tccaaagcct aaggacaccc tgatgatcag cagaacccct    840
gaagtgaccg cgtggtggtg ggatgtgtct cacgaggacc cggaagtgaa gttcaattgg    900
tacgtggacg gcgtggaagt gcacaacgcc aagaccaagc ctagagagga cagtacaaac    960
agcacctaca gagtggtgtc cgtgctgaca gtgctgcacc aggattggct gaacggcaaa   1020
gagtacaagt gcaaggtgtc caacaaggcc ctgcctgctc ctatcgaaaa gaccatcagc   1080
aaggccaagg gccagcctag ggaaccccag gtttacaacc tgcctccaag cagagaagag   1140
atgaccaaga accaggtgtc cctgacctgc ctcgtgaagg gcttctaccc ttccgatatc   1200
gccgtggaat gggagagcaa tggccagcca gagaacaact acaagacaac ccctcctgtg   1260
ctggacagcg acggctcatt cttcctgtac agcaagctga ccgtggacaa gtccagatgg   1320
cagcagggca acgtgttcag ctgcagcgtg atgcacgagg ccctgcacaa ccactacaca   1380
cagaagtctc tgtctctgtc ccctggaaaa ggcggcggag gaagcggagg cggaggatcc   1440
ggtggtggcg gatctacaat tcctccacac gtgcagaaaa gcgtgaacaa cgacatgatc   1500
gtgaccgaca acaacggggc cgtgaagttc cctcagctgt gcaagttctg cgacgtgcgg   1560
ttcagcacct gtgacaacca gaaaagctgc atgagcaact gcagcatcac cagcatctgc   1620
gagaagcccc aagaagtgtg cgtcgccgtt tggagaaaga acgacgagaa catcaccctg   1680
gaaaccgtgt gtcacgaccc caagctgccc taccacgact tcatcctgga agatgccgcc   1740
tctcctaagt gcatcatgaa ggaaaagaag aagcccggcg agacattctt catgtgcagc   1800
tgtagcagcg acgagtgcaa cgacaacatc atcttcagcg aagagtataa cacgagcaac   1860
cccgactga                                                           1869

SEQ ID NO: 8           moltype = AA  length = 620
FEATURE                Location/Qualifiers
REGION                 1..620
                       note = TGF_beta_Trap_HC- NTX-PMD-069
source                 1..620
                       mol_type = protein
                       organism = synthetic construct
SEQUENCE: 8
YRMQLLSCIA LSLALVTNSE VQLLESGGGL VQPGGSLRLS CAASGFTFSS YIMMWVRQAP     60
GKGLEWVSSI YPSGGITFYA DTVKGRFTIS RDNSKNTLYL QMNSLRAEDT AVYYCARKLG    120
TVTTVDYWGQ GTLVTVSSAS TKGPSVFPLA PSSKSTSGGT AALGCLVKDY FPEPVTVSWN    180
SGALTSGVHT FPAVLQSSGL YSLSSVVTVP SSSLGTQTYI CNVNHKPSNT KVDKRVEPKS    240
CDKTHTCPPC PAPELLGGPS VFLFPPKPKD TLMISRTPEV TCVVVDVSHE DPEVKFNWYV    300
DGVEVHNAKT KPREEQYNST YRVVSVLTVL HQDWLNGKEY KCKVSNKALP APIEKTISKA    360
KGQPREPQVY TLPPSREEMT KNQVSLTCLV KGFYPSDIAV EWESNGQPEN NYKTTPPVLD    420
SDGSFFLYSK LTVDKSRWQQ GNVFSCSVMH EALHNHYTQK SLSLSPGKGG GGSGGGGSGG    480
GGSTIPPHVQ KSVNNDMIVT DNNGAVKFPQ LCKFCDVRFS TCDNQKSCMS NCSITSICEK    540
PQEVCVAVWR KNDENITLET VCHDPKLPYH DFILEDAASP KCIMKEKKKP GETFFMCSCS    600
SDECNDNIIF SEEYNTSNPD                                                620

SEQ ID NO: 9           moltype = DNA  length = 711
FEATURE                Location/Qualifiers
misc_feature           1..711
                       note = TGF_beta_Trap_LC- NTX-PMD-070
source                 1..711
                       mol_type = other DNA
                       organism = synthetic construct
SEQUENCE: 9
atgtaccgga tgcagctgct gagctgtatc gccctgtctc tggccctggt cacaaacagc     60
cagtctgccc tgacacagcc tgcctctgtg tctggatctc ctggccagag catcaccatc    120
agctgtaccg gcacaagctc tgacgtcggc ggctacaatt acgtgtcctg gtatcagcag    180
caccccggca aggctcccaa gctgatgatc tacgacgtgt ccaacagacc cagcggcgtg    240
tccaatagat ctctccggca gcaagagcgg aacaccgcca gtctgacaat cagcggactg    300
caggctgagg acgaggccga ctactactgt agcagctaca ccagctccag caccagagtg    360
ttcggcaccg gcaccaaagt gacagtgctg ggacagccca aggctaaccc taccgtgaca    420
ctgttccctc caagcagcga agaactgcag gccaacactg gtgcctgcct ggtgtgcctg    480
agcgacttct atcctggcgc cgtgacagtg gcctgaagtg ctgatggatc tccagtgaag   540
gctggcgtgg aaaccaccaa gcctagcaag cagagcaaca caaatacgc cgccagcagc    600
tatctgagcc tgacacctga gcagtggaag tcccacagat cctacagctg ccaagtgacc    660
cacgagggca gcaccgtgga aaagacagtg gctcctacca gtgcagctg a              711

SEQ ID NO: 10          moltype = AA  length = 236
FEATURE                Location/Qualifiers
REGION                 1..236
                       note = TGF_beta_Trap_LC- NTX-PMD-070
source                 1..236
                       mol_type = protein
                       organism = synthetic construct
SEQUENCE: 10
MYRMQLLSCI ALSLALVTNS QSALTQPASV SGSPGQSITI SCTGTSSDVG GYNYVSWYQQ     60
HPGKAPKLMI YDVSNRPSGV SNRFSGSKSG NTASLTISGL QAEDEADYYC SSYTSSSTRV    120
```

```
FGTGTKVTVL GQPKANPTVT LFPPSSEELQ ANKATLVCLI SDFYPGAVTV AWKADGSPVK    180
AGVETTKPSK QSNNKYAASS YLSLTPEQWK SHRSYSCQVT HEGSTVEKTV APTECS       236

SEQ ID NO: 11          moltype = DNA  length = 846
FEATURE                Location/Qualifiers
misc_feature           1..846
                       note = TNFSF14/LIGHT
source                 1..846
                       mol_type = other DNA
                       organism = synthetic construct
SEQUENCE: 11
gagcctcctg gagactgggg gcctcctccc tggagatcca cccccaaaac cgacgtcttg    60
aggctggtgc tgtatctcac cttcctggga gcccctgct acgccccagc tctgccgtcc    120
tgcaaggagg acgagtaccc agtgggctcc gagtgctgcc ccaagtgcag tccaggttat   180
cgtgtgaagg aggcctgcgg ggagctgacg ggcacagtgt gtgaaccctg ccctccaggc   240
acctacattg cccacctcaa tggcctaagc aagtgtctgc agtgccaaat gtgtgaccca   300
gccatgggcc tgcgcgcgag ccggaactgc tccaggacag agaacgccgt gtgtggctgc   360
agcccaggcc acttctgcat cgtccaggac ggggaccact gcgccgcgtg ccgcgcttac   420
gccacctcca gcccgggcca gagggtgcag aagggaggca ccgagagtca ggacaccctg   480
tgtcagaact gcccccgggg gaccttctct cccaatggga ccctggagga atgtcagcac   540
cagaccaagt gcagctggct ggtgacgaag gccgagctg ggaccagcag ctcccactgg    600
gtatggtggt ttctctcagg gagcctcgtc atcgtcattg tttgctccac agttggccta   660
atcatatgtg tgaaaagaag aaagccaagg ggtgatgtag tcaaggtgat cgtctccgtc   720
cagcggaaaa gacaggaggc agaaggtgag gccacagtca ttgaggccct gcaggccct    780
ccggacgtca ccacggtggc cgtggaggag acaatacct cattcacggg gaggagccca    840
aaccac                                                              846

SEQ ID NO: 12          moltype = AA  length = 282
FEATURE                Location/Qualifiers
REGION                 1..282
                       note = TNFSF14/LIGHT
source                 1..282
                       mol_type = protein
                       organism = synthetic construct
SEQUENCE: 12
EPPGDWGPPP WRSTPKTDVL RLVLYLTFLG APCYAPALPS CKEDEYPVGS ECCPKCSPGY    60
RVKEACGELT GTVCEPCPPG TYIAHLNGLS KCLQCQMCDP AMGLRASRNC SRTENAVCGC   120
SPGHFCIVQD GDHCAACRAY ATSSPGQRVQ KGGTESQDTL CQNCPPGTFS PNGTLEECQH   180
QTKCSWLVTK AGAGTSSSHW VWWFLSGSLV IVIVCSTVGL IICVKRRKPR GDVVKVIVSV   240
QRKRQEAEGE ATVIEALQAP PDVTTVAVEE TIPSFTGRSP NH                      282

SEQ ID NO: 13          moltype = AA  length = 8
FEATURE                Location/Qualifiers
REGION                 1..8
                       note = OVA peptide
source                 1..8
                       mol_type = protein
                       organism = synthetic construct
SEQUENCE: 13
SIINFEKL                                                             8
```

What is claimed is:

1. A therapeutic mRNA composition comprising:
   a first mRNA scaffold comprising a first mRNA coding region encoding HPV16 E6 E7;
   a second mRNA scaffold comprising a second mRNA coding region encoding interleukin-12, wherein the second mRNA coding region has at least about 80% nucleic acid sequence identity to SEQ ID NO:5; and
   a third mRNA scaffold comprising a third mRNA coding region encoding tumor necrosis factor superfamily member 14 (TNFSF14) wherein the third mRNA coding region has at least about 80% nucleic acid sequence identity to SEQ ID NO:11, and
   wherein the first mRNA scaffold, the second mRNA scaffold and, the third mRNA scaffold are encapsulated in a delivery vehicle, wherein the delivery vehicle is selected from the group consisting of lipid nanoparticles, polymer-based nanoparticles, cationic lipids, ionizable lipids, amino-lipidated peptoids, amphipathic molecules/nanoparticles, and tertiary amino lipidated cationic peptides.

2. The therapeutic mRNA composition of claim 1, wherein the first mRNA scaffold and the second mRNA scaffold are encapsulated in a single delivery vehicle.

3. The therapeutic mRNA composition of claim 1, wherein the first mRNA scaffold, the second mRNA scaffold, and the third mRNA scaffold are encapsulated in a single delivery vehicle.

4. The therapeutic mRNA composition of claim 1, wherein the interleukin-12 has at least about 80% amino acid sequence identity to SEQ ID NO:6.

5. The therapeutic mRNA composition of claim 1, wherein the TNFSF14 has at least about 80% amino acid sequence identity to SEQ ID NO:12.

6. The therapeutic mRNA composition of claim 1, wherein the TNFSF14 is wild type TNFSF14.

7. The therapeutic mRNA composition of claim 1, wherein the therapeutic mRNA composition is an mRNA nanoparticle, an mRNA treatment nanoparticle, or a vaccine.

8. The therapeutic mRNA composition of claim 1, wherein the therapeutic mRNA composition is configured to be administered to a subject known to have cervical cancer.

9. The composition of claim 1, wherein the therapeutic mRNA composition is configured to be injected intratumorally.

10. A therapeutic mRNA composition comprising:
a single mRNA scaffold, wherein the single mRNA scaffold comprises:
a 5' UTR,
a first immunomodulatory mRNA open reading frame encoding interleukin-12, wherein the first immunomodulatory mRNA open reading frame has at least about 80% nucleic acid sequence identity to SEQ ID NO:5,
a tumor-specific antigen mRNA open reading frame encoding HPV16 E6 E7,
a second immunomodulatory mRNA open reading frame encoding TNFSF14, wherein the second immunomodulatory mRNA open reading frame has at least about 80% nucleic acid sequence identity to SEQ ID NO:11,
and a 3'UTR,
wherein the single mRNA scaffold is encapsulated in a delivery vehicle, wherein the delivery vehicle is selected from the group consisting of wherein the delivery vehicle is selected from the group consisting of lipid nanoparticles, polymer-based nanoparticles, cationic lipids, ionizable lipids, amino-lipidated peptoids, amphipathic molecules/nanoparticles, and tertiary amino lipidated cationic peptoids.

11. The therapeutic mRNA composition of claim 10, wherein the interleukin-12 has at least about 80% amino acid sequence identity to SEQ ID NO:6.

12. The therapeutic mRNA composition of claim 10, wherein the TNFSF14 has at least about 80% amino acid sequence identity to SEQ ID NO:12.

13. The therapeutic mRNA composition of claim 10, wherein the TNFSF14 is wild type TNFSF14.

14. The therapeutic mRNA composition of claim 10, wherein the therapeutic mRNA composition is an mRNA nanoparticle, an mRNA treatment nanoparticle, or a vaccine.

15. The therapeutic mRNA composition of claim 10, wherein the therapeutic mRNA composition is configured to be administered to a subject known to have cervical cancer.

16. The therapeutic mRNA composition of claim 10, wherein the therapeutic mRNA composition is configured to be injected intratumorally.

* * * * *